United States Patent
Yamaki et al.

(10) Patent No.: US 11,283,025 B2
(45) Date of Patent: Mar. 22, 2022

(54) COMPOUND, MATERIAL FOR ORGANIC ELECTROLUMINESCENCE ELEMENTS, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Taro Yamaki, Chiba (JP); Tomoki Kato, Ichihara (JP); Masahiro Kawamura, Chiba (JP); Hirokatsu Ito, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 1050 days.

(21) Appl. No.: 15/748,940

(22) PCT Filed: Aug. 1, 2016

(86) PCT No.: PCT/JP2016/072565
§ 371 (c)(1),
(2) Date: Jan. 30, 2018

(87) PCT Pub. No.: WO2017/022730
PCT Pub. Date: Feb. 9, 2017

(65) Prior Publication Data
US 2019/0006591 A1  Jan. 3, 2019

(30) Foreign Application Priority Data
Jul. 31, 2015  (JP) .............................. JP2015-152961

(51) Int. Cl.
| H01L 51/54 | (2006.01) |
| H01L 51/00 | (2006.01) |
| C07D 333/76 | (2006.01) |
| C07D 307/91 | (2006.01) |
| C07D 409/12 | (2006.01) |
| C09K 11/06 | (2006.01) |
| H01L 51/50 | (2006.01) |

(52) U.S. Cl.
CPC .......... *H01L 51/006* (2013.01); *C07D 307/91* (2013.01); *C07D 333/76* (2013.01); *C07D 409/12* (2013.01); *C09K 11/06* (2013.01); *H01L 51/0061* (2013.01); *H01L 51/0073* (2013.01); *H01L 51/0074* (2013.01); *C09K 2211/1018* (2013.01); *H01L 51/0052* (2013.01); *H01L 51/0058* (2013.01); *H01L 51/5012* (2013.01); *H01L 51/5016* (2013.01); *H01L 51/5056* (2013.01); *H01L 51/5064* (2013.01); *H01L 51/5096* (2013.01)

(58) Field of Classification Search
None
See application file for complete search history.

(56) References Cited

U.S. PATENT DOCUMENTS

| 9,087,997 B2 | 7/2015 | Yabunouchi |
| 2007/0278938 A1 | 12/2007 | Yabunouchi et al. |
| 2010/0001636 A1* | 1/2010 | Yabunouchi ........ H01L 51/0061 |
| | | 313/504 |
| 2012/0161119 A1 | 6/2012 | Yabunouchi |
| 2012/0181521 A1 | 7/2012 | Yabunouchi et al. |
| 2012/0248426 A1 | 10/2012 | Kato |
| 2014/0159006 A1 | 6/2014 | Yabunouchi et al. |
| 2015/0155491 A1 | 6/2015 | Mujica-Fernaud et al. |
| 2016/0043316 A1 | 2/2016 | Takada et al. |
| 2016/0009381 A1 | 3/2016 | Hideo et al. |
| 2016/0093810 A1* | 3/2016 | Miyake ................ C07D 405/14 |
| | | 548/440 |

(Continued)

FOREIGN PATENT DOCUMENTS

| CN | 101432272 A | 5/2009 |
| CN | 102046613 A | 5/2011 |

(Continued)

OTHER PUBLICATIONS

Office Action dated Apr. 21, 2020 in corresponding Japanese Patent Application No. 2017-533069 (with English Translation), 8 pages.

(Continued)

*Primary Examiner* — Andrew K Bohaty
(74) *Attorney, Agent, or Firm* — Oblon, McClelland, Maier & Neustadt, L.L.P.

(57) ABSTRACT

A compound represented by formula (1):

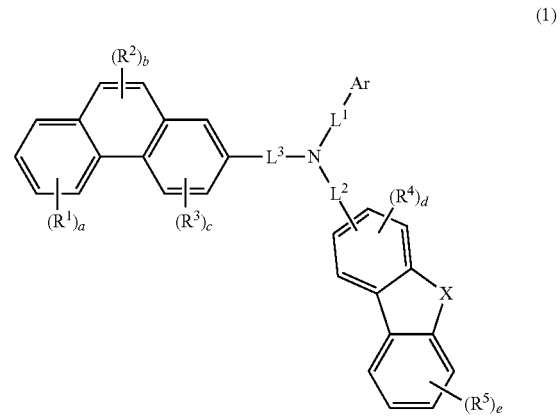

wherein $R^1$ to $R^5$, a to e, $L^1$ to $L^3$, Ar, and X are as defined in the description.

29 Claims, 1 Drawing Sheet

(56) References Cited

U.S. PATENT DOCUMENTS

| | | | |
|---|---|---|---|
| 2016/0118596 A1* | 4/2016 | Sakamoto | C09K 11/025 257/40 |
| 2016/0118597 A1 | 4/2016 | Itoi et al. | |
| 2016/0197283 A1 | 7/2016 | Itoi et al. | |
| 2017/0133591 A1 | 5/2017 | Takada et al. | |

FOREIGN PATENT DOCUMENTS

| | | |
|---|---|---|
| CN | 102596907 A | 7/2012 |
| CN | 104364245 A | 2/2015 |
| CN | 105541790 A | 5/2016 |
| JP | 2016-40824 A | 3/2016 |
| JP | 2016-66723 A | 4/2016 |
| JP | 2016-86127 A | 5/2016 |
| JP | 2016-86155 A | 5/2016 |
| KR | 10-1530049 B1 | 6/2015 |
| KR | 10-2016-0027940 A | 3/2016 |
| KR | 10-2016-0066308 A | 6/2016 |
| WO | 2007/125714 A1 | 11/2007 |
| WO | 2009/145016 A1 | 12/2009 |
| WO | 2011/059099 A1 | 5/2011 |
| WO | 2012/091471 A2 | 7/2012 |
| WO | 2015/194791 A2 | 12/2015 |
| WO | WO 2016/024792 A1 | 2/2016 |

OTHER PUBLICATIONS

Combined Chinese Office Action and Search Report dated Apr. 14, 2021 in Chinese Patent Application No. 201680045044.3, 8 pages.
International Search Report dated Aug. 30, 2016 in PCT/JP2016/072565 filed Aug. 1, 2016.
Office Action dated Dec. 1, 2020 in corresponding Japanese Patent Application No. 2017-533069 (with English Translation), 5 pages.
Chinese Office Action dated Sep. 33. 2021 in Chinese Patent Application No. 201680045044.3, 6 pages.

* cited by examiner

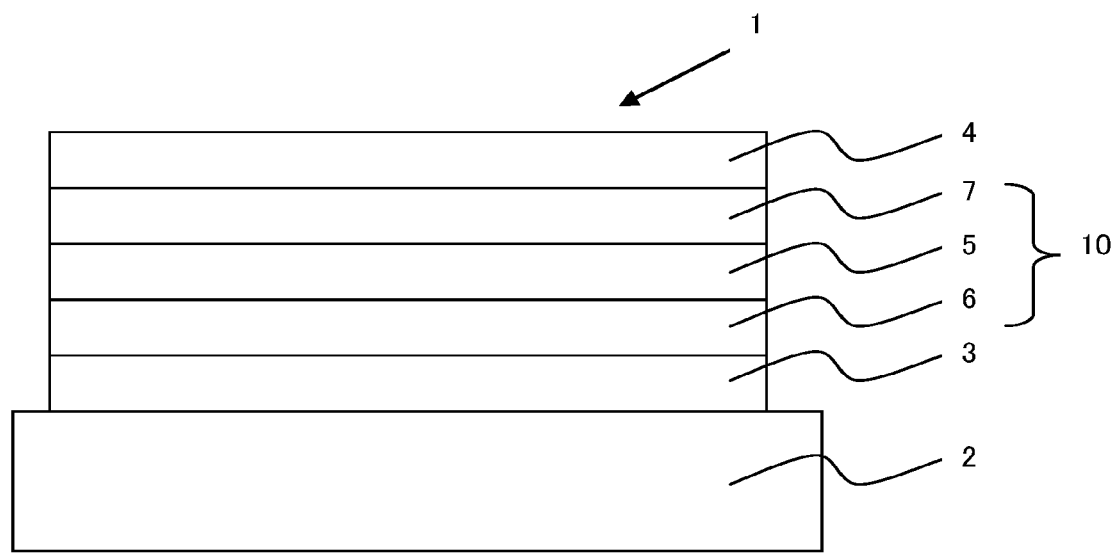

COMPOUND, MATERIAL FOR ORGANIC ELECTROLUMINESCENCE ELEMENTS, ORGANIC ELECTROLUMINESCENCE ELEMENT, AND ELECTRONIC DEVICE

TECHNICAL FIELD

The present invention relates to compounds, materials for organic electroluminescence devices, organic electroluminescence devices, and electronic devices.

BACKGROUND ART

An organic electroluminescence device ("organic EL device") generally comprises an anode, a cathode, and an organic thin film layer comprising one or more layers between the anode and the cathode. When a voltage is applied between the electrodes, electrons are injected from the cathode and holes are injected from the anode into a light emitting region. The injected electrons recombine with the injected holes in the light emitting region to form excited states. When the excited state returns to the ground state, the energy is released as light. Therefore, it is important for increasing the efficiency of an organic EL device to develop a compound which transports electrons or holes into a light emitting region efficiently and facilitates the recombination of electrons and holes.

Patent Literature 1 describes a tertiary amine compound, for example, compound H14, wherein at least one dibenzofuran ring or dibenzothiophene ring is bonded to the central nitrogen atom via a linker. Patent Literature 1 describes that the compound described therein is usable in a hole injecting layer, a hole transporting layer, a light emitting layer, or other layers of organic EL devices.

Patent Literature 2 describes a tertiary amine compound, for example, compounds 1-1, 4-2, and 4-3, wherein a 3-phenanthryl group is bonded to the central nitrogen atom directly or via a linker. Patent Literature 2 describes that these compounds are usable in a hole injecting layer, a hole transporting layer, a light emitting layer, or other layers of organic EL devices. In the working examples, these compounds are used in electron blocking layers (EBL).

However, a new material which makes it possible to drive organic EL devices at a low voltage has been still demanded to develop.

CITATION LIST

Patent Literature

Patent Literature 1: WO 2007/125714
Patent Literature 2: US 2015/0155491A

SUMMARY OF INVENTION

Technical Problem

The present invention has been made to solve the above problem and an object thereof is to provide organic EL devices which are operated at a low driving voltage and new materials which realize such organic EL devices.

Solution to Problem

As a result of extensive research for achieving the above object, the inventors have found that, by using a compound represented by formula (1), organic EL devices which are operated at a low driving voltage are obtained and further organic EL devices having long lifetime are obtained.

In an aspect of the invention, the following (1) to (4) are provided.

(1) A compound represented by formula (1) (hereinafter also referred to as "compound (1)"):

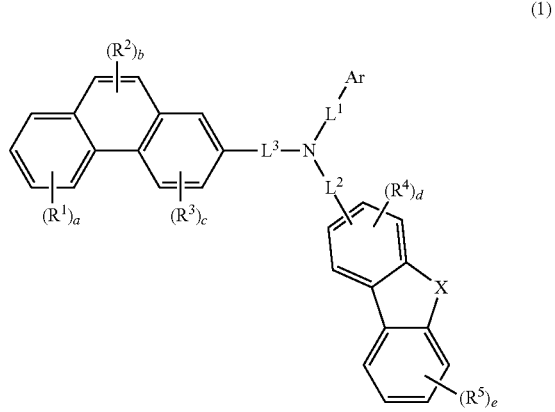

(1)

wherein:
each of $R^1$ to $R^3$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;

each of $R^4$ and $R^5$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;

a is an integer of 0 to 4, b is an integer of 0 to 2, c is an integer of 0 to 3, d is an integer of 0 to 3, e is an integer of 0 to 4; each of $(R^4)_0$, $(R^2)_0$, $(R^3)_0$, $(R^4)_0$, and $(R^5)_0$ respectively mean that $R^1$, $R^2$, $R^3$, $R^4$ or $R^5$ is not present; when a, b, c, d, or e is an integer of 2 or more, two to four $R^1$'s, two $R^2$'s, two or three $R^3$'s, two or three $R^4$'s, and two to four $R^5$'s may be the same or different, respectively; and adjacent two selected from $R^1$ to $R^5$ are not bonded to each other, thereby failing to form a ring structure;

each of $L^1$ to $L^3$ is independently a single bond or a substituted or unsubstituted arylene group having 6 to 30 ring carbon atoms;

Ar is a substituted or unsubstituted aryl group having 6 to 50 ring carbon atoms, a substituted or unsubstituted heteroaryl group having 5 to 12 ring atoms, or a substituted or unsubstituted heteroaryl group having 13 to 50 ring atoms, wherein at least one ring heteroatom is selected from an oxygen atom and a sulfur atom;

X is an oxygen atom or a sulfur atom; and an optional substituent referred to by "substituted or unsubstituted" is one selected from the group consisting of an alkyl group having 1 to 20 carbon atoms, an aryl group having 6 to 18 ring carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group, and two or more optional groups, if present, may be the same or different.
(2) A material for organic electroluminescence devices comprising the compound (1) of the item (1).
(3) An organic electroluminescence device comprising a cathode, an anode, and an organic thin film layer disposed between the cathode and the anode, wherein the organic thin film layer comprises one or more layers, the organic thin film layer comprises a light emitting layer, and at least one layer of the organic thin film layer comprises the compound (1) of the item (1).
(4) An electronic device comprising the organic electroluminescence device of the item (3).

Advantageous Effects of Invention

Organic EL devices produced by using the compound (1) are operated at a low driving voltage.

BRIEF DESCRIPTION OF DRAWINGS

FIG. 1 is a schematic view showing the structure of the organic EL device in an aspect of the invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

In the compound in an aspect of the present invention, examples, preferred examples, etc. described with respect to a group may be combined with any of examples, preferred examples, etc. described with respect to other groups. A specific group selected from examples, preferred examples, etc. described with respect to a group may be combined with another specific group selected from examples, preferred examples, etc. described with respect to any of other groups.

The same also applies to the number of atoms, the number of carbon atoms, and other features. In addition, the same also applies to any of the combinations between the groups, the number of atoms, the number of carbon atoms, and other features.

The compound in an aspect of the invention is represented by formula (1):

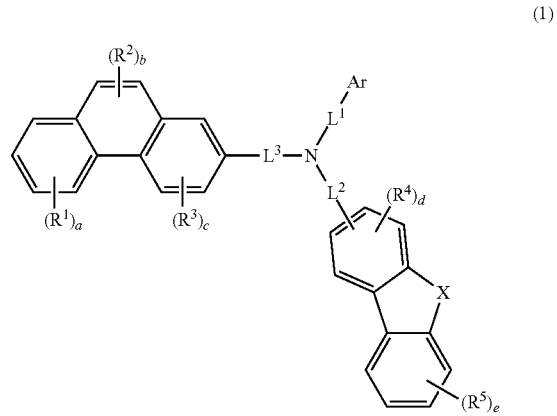

wherein:
each of $R^1$ to $R^3$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;

each of $R^4$ and $R^5$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;

a is an integer of 0 to 4, b is an integer of 0 to 2, c is an integer of 0 to 3, d is an integer of 0 to 3, and e is an integer of 0 to 4; $(R^4)_0$, $(R^2)_0$, $(R^3)_0$, $(R^4)_0$, and $(R^5)_0$ respectively mean that $R^1$, $R^2$, $R^3$, $R^4$ or $R^5$ is not present; when a, b, c, d, or e is an integer of 2 or more, two to four $R^1$'s, two $R^2$'s, two or three $R^3$'s, two or three $R^4$'s, and two to four $R^5$'s respectively may be the same or different; and adjacent two selected from $R^1$ to $R^5$ are not bonded to each other, thereby failing to form a ring structure;

each of $L^1$ to $L^3$ is independently a single bond or a substituted or unsubstituted arylene group having 6 to 30 ring carbon atoms;

Ar is a substituted or unsubstituted aryl group having 6 to 50 ring carbon atoms, a substituted or unsubstituted heteroaryl group having 5 to 12 ring atoms, or a substituted or unsubstituted heteroaryl group having 13 to 50 ring atoms, wherein at least one ring heteroatom is selected from an oxygen atom and a sulfur atom;

X is an oxygen atom or a sulfur atom;

an optional substituent referred to by "substituted or unsubstituted" is one selected from the group consisting of an alkyl group having 1 to 20 carbon atoms, an aryl group having 6 to 18 ring carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group; and two or more optional groups, if present, may be the same or different.

The compound (1) is preferably represented by any of formulae (2) to (5):

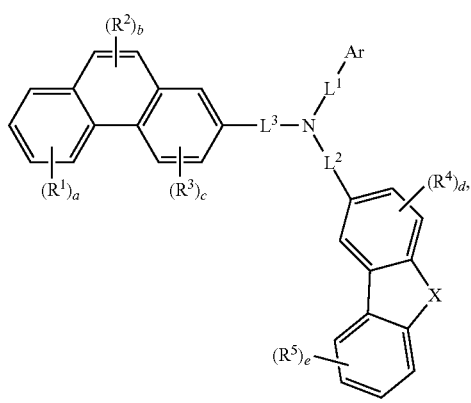
(2)

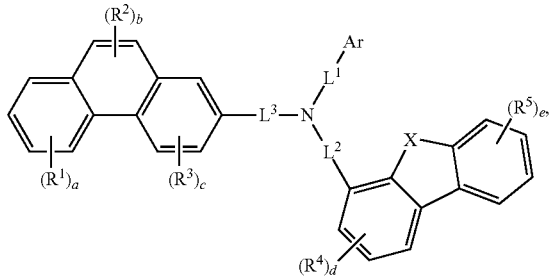
(3)

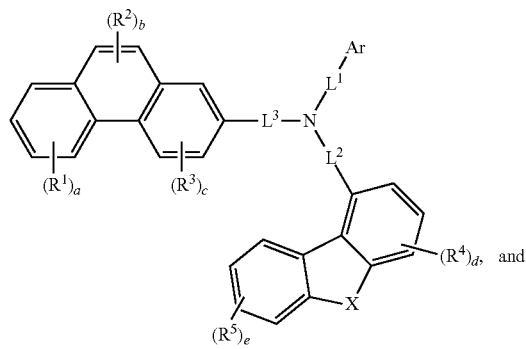
(4)

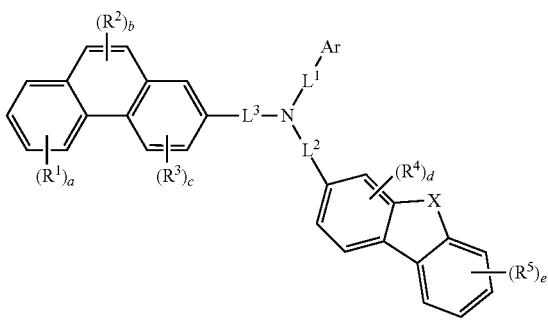
(5)

wherein $R^1$ to $R^5$, a to e, $L^1$ to $L^3$, Ar, and X are as defined in formula (1).

Each of $R^1$ to $R^3$ is independently an alkyl group having 1 to 20, preferably 1 to 5, and more preferably 1 to 4 carbon atoms; a cycloalkyl group having 3 to 50, preferably 3 to 10, more preferably 3 to 6, and still more preferably 5 or 6 ring carbon atoms; a haloalkyl group having 1 to 20, preferably 1 to 5, and more preferably 1 to 4 carbon atoms; an alkoxy group having 1 to 20, preferably 1 to 5, and more preferably 1 to 4 carbon atoms; a haloalkoxy group having 1 to 20, preferably 1 to 5, and more preferably 1 to 4 carbon atoms; an aryl group having 6 to 18, preferably 6 to 12, more preferably 6 to 10, and still more preferably 6 ring carbon atoms; an aryloxy group having 6 to 18 and preferably 6 to 12 ring carbon atoms; a halogen atom; or a cyano group.

Preferably, each of $R^1$ to $R^3$ is independently one selected from the group consisting of an alkyl group having 1 to 20 carbon atoms, an aryl group having 6 to 18 ring carbon atoms, an aryloxy group having 6 to 50 ring carbon atoms, and a cyano group, and more preferably an alkyl group having 1 to 20 carbon atoms or an aryl group having 6 to 18 ring carbon atoms.

Each of $R^4$ and $R^5$ is independently an alkyl group having 1 to 20, preferably 1 to 5, and more preferably 1 to 4 carbon atoms; a cycloalkyl group having 3 to 50, preferably 3 to 10, and more preferably 3 to 6 ring carbon atoms; a haloalkyl group having 1 to 20, preferably 1 to 5, and more preferably 1 to 4 carbon atoms; an alkoxy group having 1 to 20, preferably 1 to 5, and more preferably 1 to 4 carbon atoms; a haloalkoxy group having 1 to 20, preferably 1 to 5, and more preferably 1 to 4 carbon atoms; an aryl group having 6 to 18 and preferably 6 to 12 ring carbon atoms; an aryloxy group having 6 to 18 and preferably 6 to 12 ring carbon atoms; a halogen atom; or a cyano group.

Preferably, each of $R^4$ and $R^5$ is independently selected from an alkyl group having 1 to 20 carbon atoms and an aryl group having 6 to 18 ring carbon atoms.

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred, a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the cycloalkyl group having 3 to 50 ring carbon atoms include a cyclopropyl group, a cyclobutyl group, a cyclopentyl group, a cyclohexyl group, and a cycloheptyl group.

The haloalkyl group having 1 to 20 carbon atoms is, for example, a group obtained by replacing at least one, preferably 1 to 7 hydrogen atoms, or all the hydrogen atoms of the alkyl group having 1 to 20 carbon atoms mentioned above with a halogen atom selected from the group consisting of a fluorine atom, a chlorine atom, a bromine atom, and an iodine atom, preferably a fluorine atom. The haloalkyl group is preferably a heptafluoropropyl group (inclusive of isomeric groups), a pentafluoroethyl group, a 2,2,2-trifluoroethyl group, or a trifluoromethyl group, more preferably a pentafluoroethyl group, a 2,2,2-trifluoroethyl group, or a trifluoromethyl group, and still more preferably a trifluoromethyl group.

The alkoxy group having 1 to 20 carbon atoms is represented by $—OR^{11}$, wherein $R^{11}$ is the alkyl group having 1 to 20 carbon atoms mentioned above. The alkoxy group is preferably a t-butoxy group, a propoxy group (inclusive of isomeric groups), an ethoxy group, or a methoxy group, more preferably an ethoxy group or a methoxy group, and still more preferably a methoxy group.

The haloalkoxy group having 1 to 20 carbon atoms is represented by $—OR^{12}$, wherein $R^{12}$ is the haloalkyl group having 1 to 20 carbon atoms mentioned above and preferably a fluoroalkyl group having 1 to 20 carbon atoms. The haloalkoxy group is preferably a heptafluoropropoxy group (inclusive of isomeric groups), a pentafluoroethoxy group, a 2,2,2-trifluoroethoxy group, or a trifluoromethoxy group, more preferably a pentafluoroethoxy group, a 2,2,2-trifluoroethoxy group, or a trifluoromethoxy group, and still more preferably a trifluoromethoxy group.

The aryl group having 6 to 18 ring carbon atoms is, for example, a phenyl group, a biphenylyl group, a terphenylyl group, a biphenylenyl group, a naphthyl group, an acenaphthylenyl group, an anthryl group, a benzanthryl group, an aceanthryl group, a phenanthryl group (also referred to as "phenanthrenyl group"), a benzophenanthryl group, a triphenylenyl group, a phenalenyl group, a fluorenyl group, a benzofluorenyl group, a pyrenyl group, a chrysenyl group, a s-indacenyl group, an as-indacenyl group, and a fluoranthenyl group, with a phenyl group, a biphenylyl group, a terphenylyl group, and a naphthyl group being preferred, a phenyl group, a biphenylyl group, and a naphthyl group being more preferred, and a phenyl group and a biphenylyl group being still more preferred. The naphthyl group includes a 1- or 2-naphthyl group. The biphenylyl group includes a 2-, 3- or 4-biphenylyl group. The terphenyl group includes, for example, a 2-p-terphenylyl group, a 4-p-terphenylyl group, a 2'-m-terphenylyl group, and a 5'-m-terphenylyl group. When $R^5$ is a biphenylyl group, a 3-biphenylyl group is preferred.

The aryloxy group having 6 to 18 ring carbon atoms is represented by $—OR^{13}$, wherein $R^{13}$ is an aryl group having 6 to 18 and preferably 6 to 12 ring carbon atoms.

Examples of the aryl group include a phenyl group, a biphenylyl group, a terphenylyl group, a biphenylenyl group, a naphthyl group, an acenaphthylenyl group, an anthryl group, a benzanthryl group, an aceanthryl group, a phenanthryl group, a benzophenanthryl group, a triphenylenyl group, a phenalenyl group, a fluorenyl group, a benzofluorenyl group, a pyrenyl group, a chrysenyl group, a s-indacenyl group, an as-indacenyl group, and a fluoranthenyl group, with a phenyl group, a biphenylyl group, a terphenylyl group, and a naphthyl group being preferred, a phenyl group, a biphenylyl group, and a naphthyl group being more preferred, and a phenyl group being still more preferred.

The halogen atom includes a fluorine atom, a chlorine atom, a bromine atom and an iodine atom, with a fluorine atom being preferred.

a is an integer of 0 to 4, preferably 0 to 2, and more preferably 0 or 1.

b is an integer of 0 to 2 and preferably 0 or 1.

c is an integer of 0 to 3, preferably 0 to 2, and more preferably 0 or 1.

d is an integer of 0 to 3, preferably 0 to 2, and more preferably 0 or 1.

e is an integer of 0 to 4, preferably 0 to 2, and more preferably 0 or 1.

When any of a to e is 0, i.e., $(R^1)_0$, $(R^2)_0$, $(R^3)_0$, $(R^4)_0$, or $(R^5)_0$ means that $R^1$, $R^2$, $R^3$, $R^4$, or $R^5$ is not present, i.e., each benzene ring is not substituted by $R^1$, $R^2$, $R^3$, $R^4$, or $R^5$.

When a, b, c, d or e is an integer of 2 or more, two to four $R^1$'s, two $R^2$'s, two or three $R^3$'s, two or three $R^4$'s, and two to four $R^5$'s may be respectively the same or different. Adjacent two selected from $R^1$ to $R^5$ are not bonded to each other, thereby failing to form a ring structure○

Ar is a substituted or unsubstituted aryl group having 6 to 50, preferably 6 to 24, and more preferably 6 to 12 ring carbon atoms; a substituted or unsubstituted heteroaryl group having 5 to 12 ring atoms; or a substituted or unsubstituted heteroaryl group having 13 to 50, preferably 13 to 30, more preferably 13 to 24, and still more preferably 13 to 18 ring atoms, wherein at least one ring heteroatom is selected from an oxygen atom and a sulfur atom.

The heteroaryl group includes preferably 1 to 5, more preferably 1 to 3, and still more preferably 1 to 2 ring heteroatoms.

The aryl group having 6 to 50 ring carbon atoms for Ar is, for example, a phenyl group, a biphenylyl group, a terphenylyl group, a biphenylenyl group, a naphthyl group, an acenaphthylenyl group, an anthryl group, a benzanthryl group, an aceanthryl group, a 2-phenanthryl group, a benzophenanthryl group, a phenalenyl group, a fluorenyl group, a benzofluorenyl group, a 9,9'-spirobifluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group, with a phenyl group, a biphenylyl group, a terphenylyl group, a naphthyl group, and a fluorenyl group being preferred. Example of the substituted aryl group is preferably a 9,9-diphenylfluorenyl group.

The heteroaryl group having 5 to 12 ring atoms for Ar is, for example, a pyrrolyl group, a furyl group (also referred to as "furanyl group," the same applies below), a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group (also referred to as "benzothienyl group," the same applies below), an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, or a benzisothiazolyl group.

The heteroaryl group having 13 to 50 ring atoms for Ar, having an oxygen atom or a sulfur atom as the heteroatom is, for example, a dibenzofuranyl group, a naphthobenzofuranyl group, a dibenzothiophenyl group (also referred to as "dibenzothienyl group," the same applies below), a naphthobenzothiophenyl group (also referred to as "naphthobenzothienyl group," the same applies below), a phenoxazinyl group, or a xanthenyl group. Examples of the substituted heteroaryl group are preferably a dibenzofuranyl group and a dibenzothiophenyl group.

Each of $L^1$ to $L^3$ is independently a single bond or a substituted or unsubstituted arylene group having 6 to 30, preferably 6 to 24, and more preferably 6 to 12 ring carbon atoms.

The arylene group having 6 to 30 ring carbon atoms for $L^1$ to $L^3$ is a group obtained by removing one hydrogen atom from an aryl group having 6 to 30 ring carbon atoms. The aryl group is, for example, a phenyl group, a biphenylyl group, a terphenylyl group, a biphenylenyl group, a naphthyl group, an acenaphthylenyl group, an anthryl group, a benzanthryl group, an aceanthryl group, a 2-phenanthryl group, a benzophenanthryl group, a triphenylenyl group, a phenalenyl group, a fluorenyl group, a benzofluorenyl group, a 9,9'-spirobifluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, or a perylenyl group, with a phenyl group, a biphenylyl group, a terphenylyl group, a naphthyl group, and a fluorenyl group being preferred. Example of the substituted arylene group is preferably a group obtained by removing one hydrogen atom from a 9,9-diphenylfluorenyl group.

In formulae (1) to (5), the optional substituent referred to by "substituted or unsubstituted" is at least one selected from the group consisting of an alkyl group having 1 to 20, preferably 1 to 5, and more preferably 1 to 4 carbon atoms; an aryl group having 6 to 18, preferably 6 to 12, more preferably 6 to 10, and still more preferably 6 ring carbon atoms; a cycloalkyl group having 3 to 50, preferably 3 to 10, more preferably 3 to 6, and still more preferably 5 or 6 ring carbon atoms; an aralkyl group having 7 to 30 carbon atoms which includes an aryl group having 6 to 18, preferably 6 to 12, more preferably 6 to 10, and still more preferably 6 ring carbon atoms; an alkoxy group having 1 to 20, preferably 1 to 5, and more preferably 1 to 4 carbon atoms; an aryloxy group having 6 to 18, preferably 6 to 12, and more preferably 6 ring carbon atoms; a mono-, di-, or tri-substituted silyl group having a substituent selected from an alkyl group having 1 to 20, preferably 1 to 5, and more preferably 1 to 4 carbon atoms and an aryl group having 6 to 18, preferably 6 to 12, and more preferably 6 ring carbon atoms; a haloalkyl group having 1 to 20, preferably 1 to 5, and more preferably 1 to 4 carbon atoms; a haloalkoxy group having 1 to 20, preferably 1 to 5, and more preferably 1 to 4 carbon atoms; a halogen atom; a cyano group; and a nitro group. Two or more optional groups, if present, may be the same or different.

The details of the alkyl group having 1 to 20 carbon atoms, the aryl group having 6 to 18 ring carbon atoms, the cycloalkyl group having 3 to 50 ring carbon atoms, the alkoxy group having 1 to 20 carbon atoms, the aryloxy group having 6 to 18 ring carbon atoms, the haloalkyl group having 1 to 20 carbon atoms, the haloalkoxy group having 1 to 20 carbon atoms, and the halogen atom, each for the optional substituent, are as described above with respect to $R^1$ to $R^5$.

The details of the aryl group having 6 to 18 ring carbon atoms in the aralkyl group having 7 to 30 carbon atom which includes an aryl group having 6 to 18 ring carbon atoms, mentioned above as the optional substituent, are as described above.

The details of the alkyl group and the aryl group in the mono-, di-, or tri-substituted silyl group including a substituent selected from an alkyl group having 1 to 20 carbon atoms and an aryl group having 6 to 18 ring carbon atoms, mentioned above as the optional substituent, are as described above. Examples thereof include a trimethylsilyl group, a triethylsilyl group, a t-butyldimethylsilyl group, a propyklimethylsilyl group, an isopropyldimethylsilyl group, a triphenylsilyl group, a phenyldimethylsilyl group, a t-butyldiphenylsilyl group, and a tritolylsilyl group.

In preferred embodiments of the compounds represented by formulae (1) to (5), Ar is independently one selected from the group consisting of formulae (a) to (m):

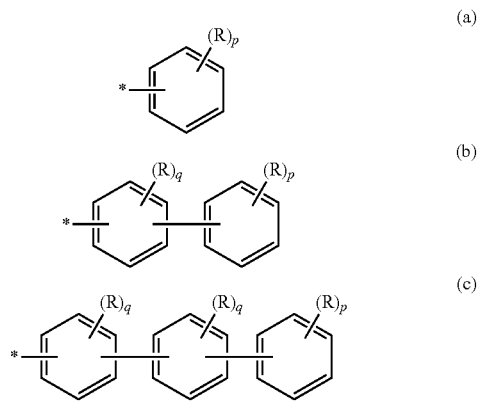

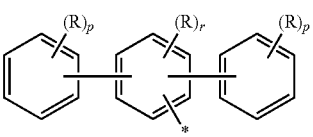

In formulae (a) to (m), * is a bond to L¹ in formulae (1) to (5).

In formulae (a) to (m), each R is independently one selected from the substituents described above with respect to the optional substituents referred to by "substituted or unsubstituted" in formulae (1) to (5), wherein the preferred R is also the same as that of the optional substituent.

In formulae (a) to (m), each p is independently an integer of 0 to 5, preferably 0 to 3, more preferably 0 or 1, and still more preferably 0. Each q is independently an integer of 0 to 4, preferably 0 to 2, more preferably 0 or 1, and still more preferably 0. Each r is independently an integer of 0 to 3, preferably 0 to 2, more preferably 0 or 1, and still more preferably 0. s is an integer of 0 to 2, preferably 0 or 1, and more preferably 0. t is 0 or 1 and preferably 0.

When p, q, r or s is an integer of 2 or more, two to five Rs, two to four Rs, two to three Rs, or two Rs may be the same or different.

When each of p to t is independently 0, each (R)₀ means that R is not present, i.e., each ring is not substituted by R. In an embodiment of the invention, the group represented by any of formulae (a) to (m) has preferably one or two Rs more preferably one R. In another embodiment of the invention, the hydrogen atom on the group represented by any of formulae (a) to (m) is preferably not substituted for a substituent R, i.e., p to t are preferably all 0.

Each of $R^a$ and $R^b$ of formula (g) is independently one selected from the group consisting of an alkyl group having 1 to 20, preferably 1 to 5, and more preferably 1 to 4 carbon atoms; an aryl group having 6 to 18, preferably 6 to 12, more preferably 6 to 10, and still more preferably 6 ring carbon atoms; a cycloalkyl group having 3 to 50, preferably 3 to 10, more preferably 3 to 6, and still more preferably 5 or 6 ring carbon atoms; an aralkyl group having 7 to 30 carbon atoms including an aryl group having 6 to 18, preferably 6 to 10, and more preferably 6 ring carbon atoms; an alkoxy group having 1 to 20, preferably 1 to 5, and more preferably 1 to 4 carbon atoms; an aryloxy group having 6 to 18, preferably 6 to 12, and more preferably 6 ring carbon atoms; an mono-, di-, or tri-substituted silyl group having an substituent selected from an alkyl group having 1 to 20, preferably 1 to 5, and more preferably 1 to 4 carbon atoms and an aryl group having 6 to 18, preferably 6 to 12, and more preferably 6 ring carbon atoms; a haloalkyl group having 1 to 20, preferably 1 to 5, and more preferably 1 to 4 carbon atoms; a haloalkoxy group having 1 to 20, preferably 1 to 5, and more preferably 1 to 4 carbon atoms; a halogen atom; a cyano group; and a nitro group.

The details for the groups represented by $R^a$ and $R^b$ are the same as those mentioned above with respect to the optional substituents referred to by "substituted or unsubstituted" of the compound (1).

Preferably, each of $R^a$ and $R^b$ is independently from an aryl group having 6 to 12 ring carbon atoms and more preferably a phenyl group.

Y of formulae (j) and (k) is a nitrogen atom, an oxygen atom, or a sulfur atom, with an oxygen atom or a sulfur atom being more preferred and a sulfur atom being more preferred.

In formulae (a) to (e) and (h) to (j), adjacent two Rs may be bonded to each other to form a ring structure together with ring carbon atoms to which the adjacent two Rs are bonded. In formula (g), two selected from R, $R^a$, and $R^b$ may be bonded to each other to form a ring structure.

The ring structure is preferably an aromatic hydrocarbon ring, such as a benzene ring, or an aromatic heterocyclic ring comprising a ring heteroatom, such as an oxygen atom and a sulfur atom.

In another embodiment of the compound represented by formula (1), adjacent two Rs are not bonded to each other.

Two selected from R, $R^a$, and $R^b$ may be bonded to each other to form a ring structure, provided that adjacent two Rs in formulae (f) and (k) to (m) are not bonded to each other, thereby failing to form a ring structure.

In an embodiment of the compound represented by any of formulae (1) to (5), the group represented by any of formulae (a) to (o) has preferably one or two Rs and more preferably one R.

In another embodiment of the compound represented by any of formulae (1) to (5), the hydrogen atom on the group represented by any of formulae (a) to (o) is preferably not substituted for R, i.e., p to t are preferably all 0.

Formula (b) is preferably a 2-biphenylyl group, a 3-biphenylyl group, or a 4-biphenylyl group, each optionally having a substituent R.

Formula (c) is preferably a 2-, 3- or 4-p-terphenylyl group, a 2-, 3- or 4-m-terphenylyl group, or a 2-, 3- or 4-o-terphenylyl group, each optionally having a substituent R.

Formula (d) is preferably a 2'-p-terphenylyl group, a 2'-, 4'-, or 5'-m-terphenylyl group, or a 4'-o-terphenylyl group, each optionally having a substituent R.

Formula (e) is preferably a 1-naphthyl group or a 2-naphthyl group, each optionally having a substituent R.

Formula (f) is preferably a 2-phenanthryl group optionally having a substituent R.

In formula (g), $R^a$ and $R^b$ are preferably both phenyl groups, or one of $R^a$ and $R^b$ is a methyl group and the other is a phenyl group. More preferably, $R^a$ and $R^b$ are both phenyl groups. The group represented by formula (g) is bonded to $L^1$ of formulae (1) to (5) at any of 1-position to 4-position, preferably at 2-position or 4-position, and more preferably at 2-position of the fluorene ring.

Formula (h) is preferably a 4-(9-phenylfluorene-9-yl)phenyl group optionally having a substituent R.

The group represented by formula (i) is bonded to $L^1$ of formulae (1) to (5) at any of 1-position to 4-position and preferably at 2-position or 4-position of the fluorene ring.

The group represented by formula (j) is bonded to $L^1$ of formulae (1) to (5) preferably at 2-position of the thiophene ring.

The group represented by formula (k) is bonded to $L^1$ of formulae (1) to (5) preferably at 2-position of the benzothiophene ring.

The group represented by formula (l) is bonded to $L^1$ of formulae (1) to (5) at any of 1-position to 4-position and preferably at 2-position or 4-position of the dibenzofuran ring.

The group represented by formula (m) is bonded to $L^1$ of formulae (1) to (5) at any of 1-position to 4-position and preferably at 2-position or 4-position of the dibenzothiophene ring.

In a more preferred embodiment of the compounds represented by formulae (1) to (5), Ar is independently represented by formula (b-1), (b-2), (b-3), (c-1), (c-2), (c-3), (d-1), (d-2), (d-3), (e-1), (f), (g-1), (i-1), (i-2), (l-1), (l-2), (m-1), or (m-2).

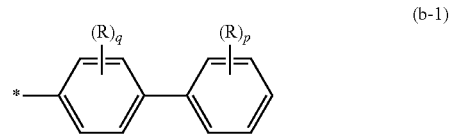

(b-1)

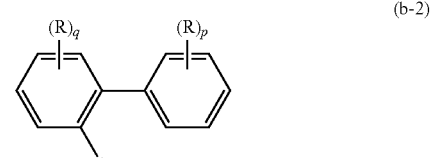

(b-2)

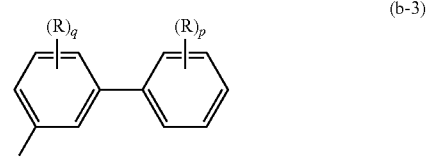

(b-3)

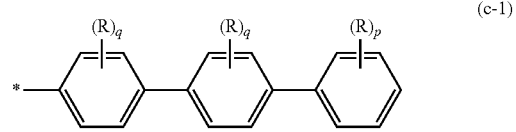

(c-1)

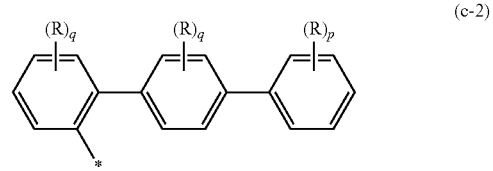

(c-2)

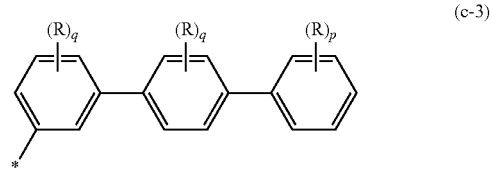

(c-3)

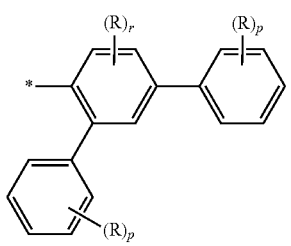
(d-1)

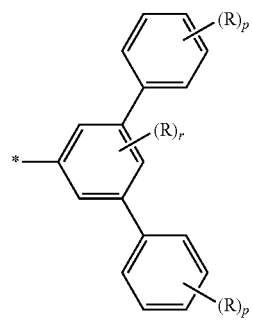
(d-2)

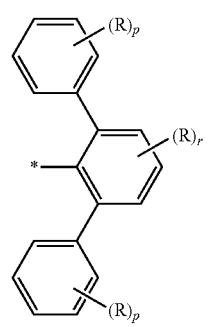
(d-3)

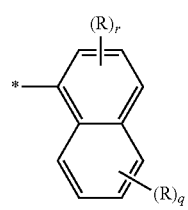
(e-1)

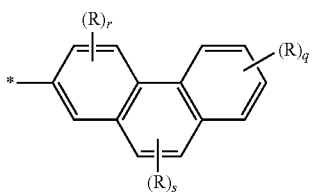
(f)

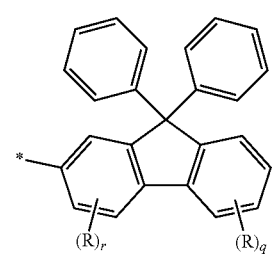
(g-1)

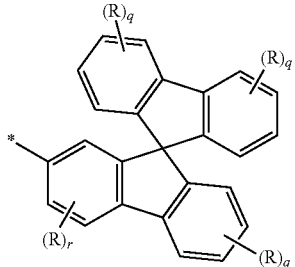
(i-1)

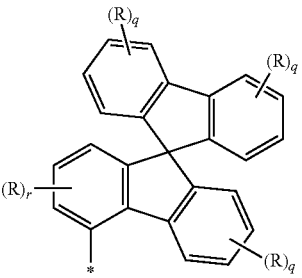
(i-2)

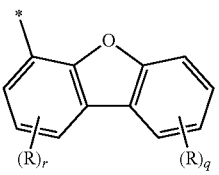
(l-1)

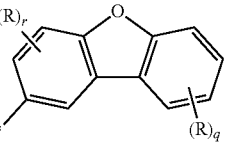
(l-2)

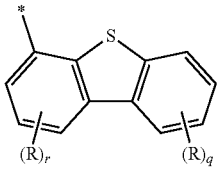
(m-1)

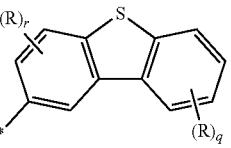
(m-2)

In formulae (b-1) to (b-3), (c-1) to (c-3), (d-1) to (d-3), (e-1), (f), (g-1), (i-2), (l-1), (l-2), (m-1), and (m-2), R, p, q, r, s, and * are the same as defined with respect to formulae (a) to (m); and $(R)_0$ means that R is not present;

provided that, in formulae (b-1) to (b-3), (c-1) to (c-3), (d-1) to (d-3), (e-1), (f), (g-1), (i-2), (l-1), (l-2), (m-1), and (m-2), adjacent two Rs are not bonded to each other, thereby failing to form a ring structure.

In an embodiment of the compounds represented by formulae (1) to (5), each of $L^1$ to $L^3$ may be a single bond or each of $L^1$ to $L^3$ may be a substituted or unsubstituted arylene group having 6 to 30, preferably 6 to 24, and more preferably 6 to 12 ring carbon atoms.

In an embodiment of the compounds represented by formulae (1) to (5), $L^3$ is preferably a single bond.

In an embodiment of the compounds represented by formulae (1) to (5), L² is preferably a substituted or unsubstituted arylene group having 6 to 30, more preferably 6 to 24, and still more preferably 6 to 12 ring carbon atoms.

The substituted or unsubstituted arylene group having 6 to 30 ring carbon atoms for L¹ to L³ is preferably represented by formula (ii) or (iii);

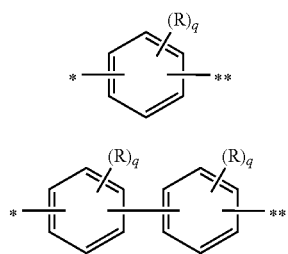

wherein:
R and q are the same as defined with respect to formulae (a) to (m);
when L¹ is represented by formula (ii) or (iii), one of * and ** is a bond to Ar in formulae (1) to (5), and the other is a bond to the nitrogen atom in formulae (1) to (5);
when L² is represented by formula (ii) or (iii), one of * and ** is a bond to the dibenzofuran ring or the dibenzothiophene ring in formulae (1) to (5), and the other is a bond to the nitrogen atom in formulae (1) to (5); and
when L³ is represented by formula (ii) or (iii), one of * and ** is a bond to the 2-phenanthryl group in formulae (1) to (5), and the other is a bond to the nitrogen atom in formulae (1) to (5).

Formulae (ii) and (iii) are preferably represented by the following formulae;

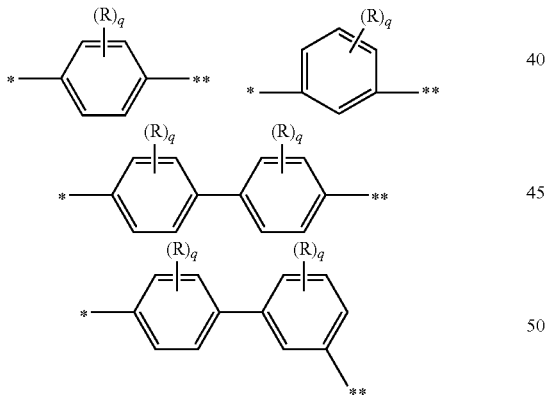

wherein R, q, *, and ** are as described above.
More preferably, formula (ii) is a p-phenylene group.
The compound represented by formula (1) is still more preferably selected from the group consisting of:
a compound represented by formula (2) or (3), wherein Ar is a group represented by any one selected from the group consisting of formulae (b-1), (b-2), (b-3), (c-1), (c-2), (c-3), (d-1), (d-3), (f), (g-1), (i-1), and (i-2), each of L¹ and L³ is a single bond, and L² is a group represented by formula (ii);
a compound represented by formula (2) or (3), wherein Ar is a group represented by formula (b-1), (b-2), (c-1), or (g-1), L¹ is a single bond, and each of L² and L³ is a group represented by formula (ii);

a compound represented by formula (2) or (3), wherein Ar is a group represented by formula (d-2), (e-1), (l-1), (l-2), (m-1), or (m-2), each of L¹ and L² is a group represented by formula (ii), and L³ is a single bond;
a compound represented by formula (4) or (5), wherein Ar is a group represented by formula (b-1) or (c-1), each of L¹ and L² is a group represented by (ii), and L³ is a single bond; and
a compound represented by formula (2) or (3), wherein Ar is a group represented by formula (b-1) or (c-1), each of L¹ and L³ is a single bond, L² is a group represented by formula (ii), R⁴ is a phenyl group, R⁵ is a phenyl group or a biphenyl group, d is 0 or 1, and e is 1.

Examples of the compound (1) are shown below, although not limited thereto.

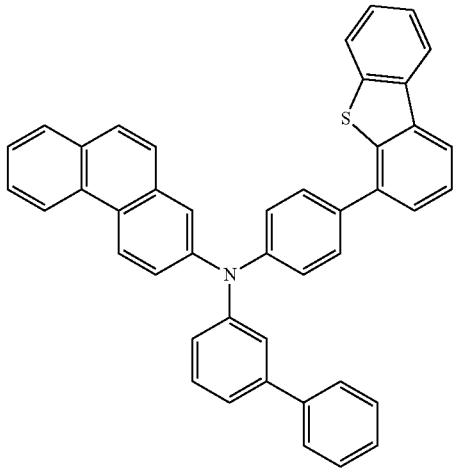

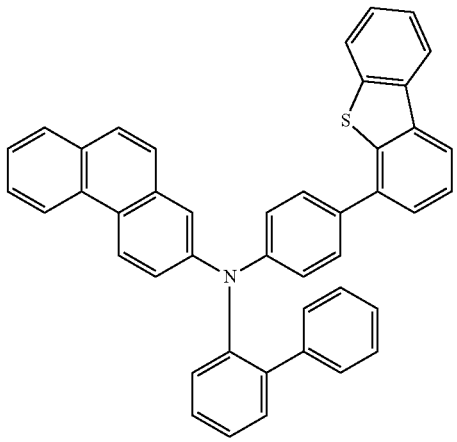

19
-continued
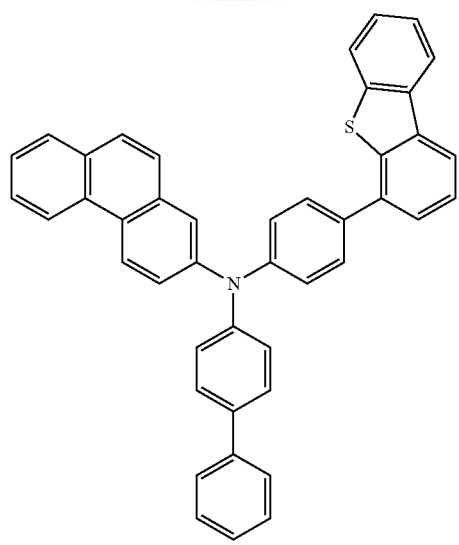
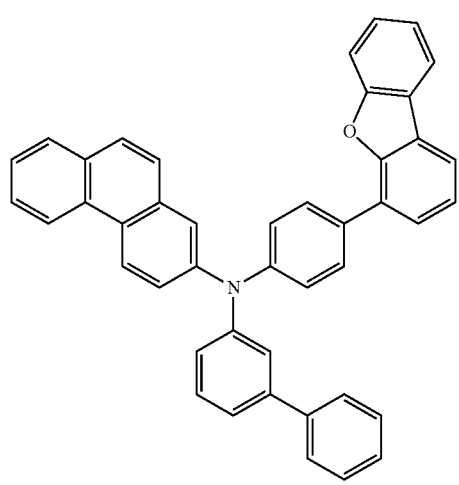
20
-continued
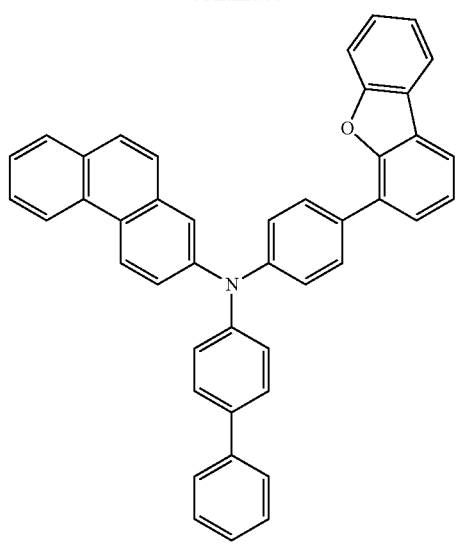
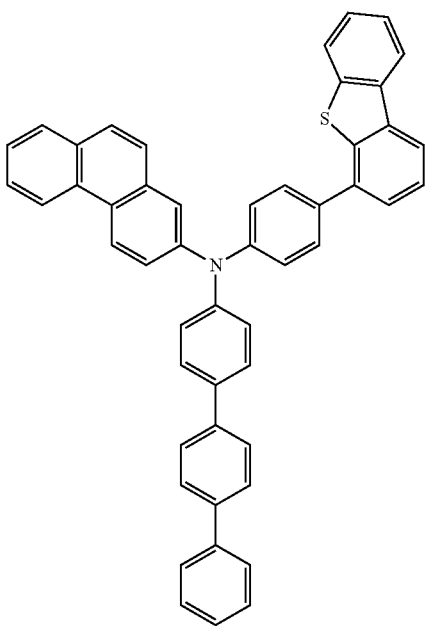

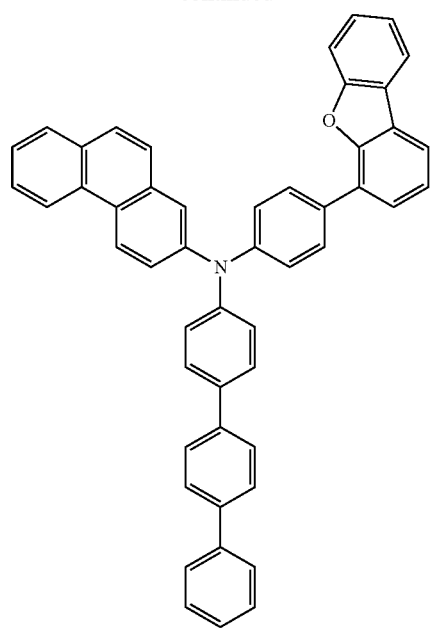
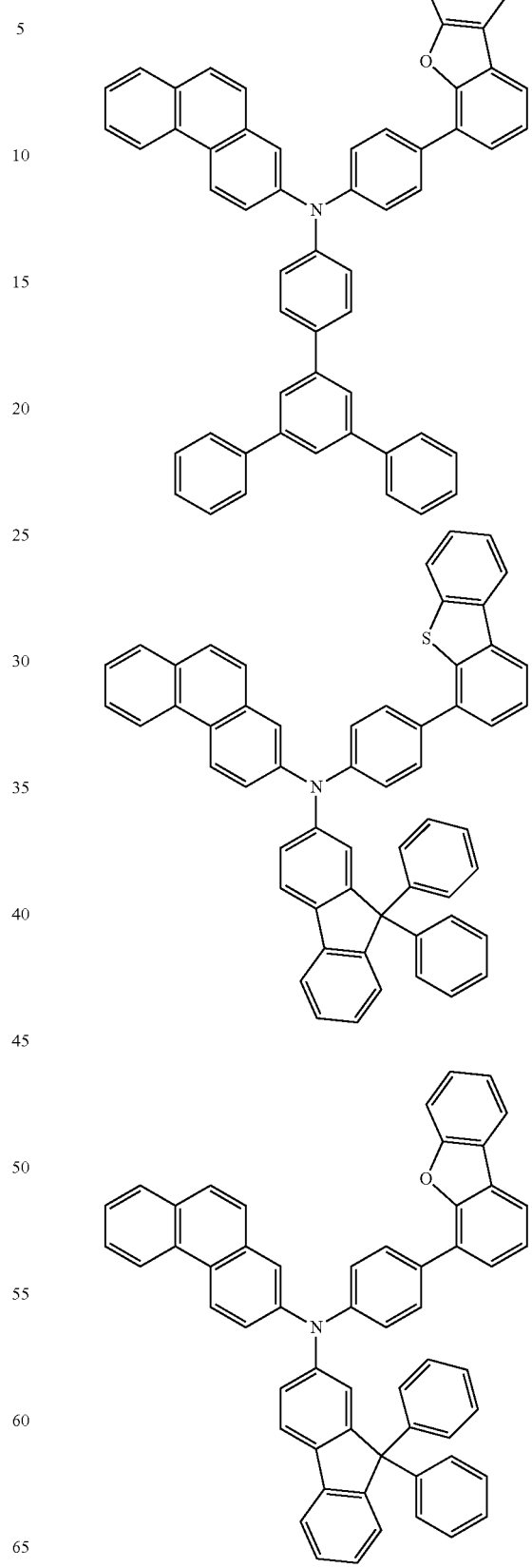

23
-continued
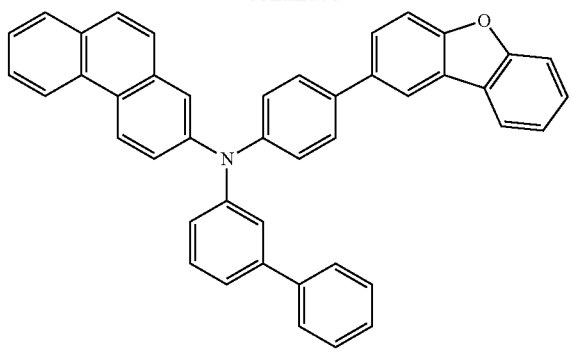
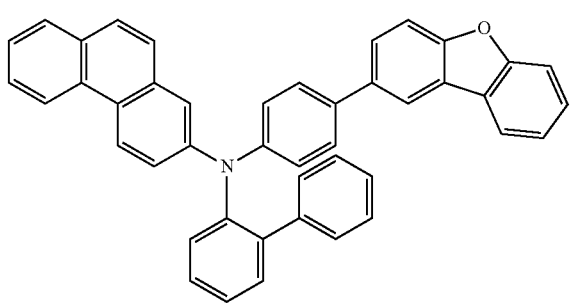
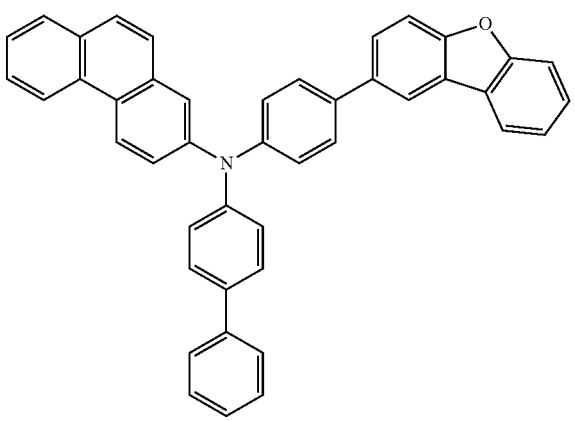
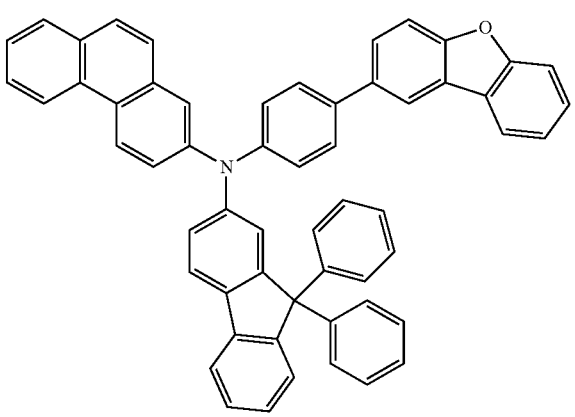
24
-continued
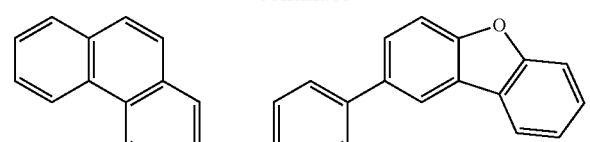
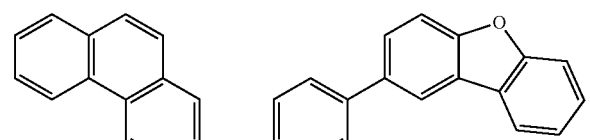
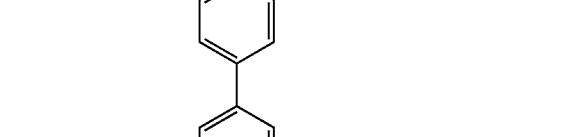
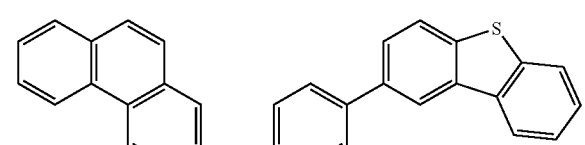
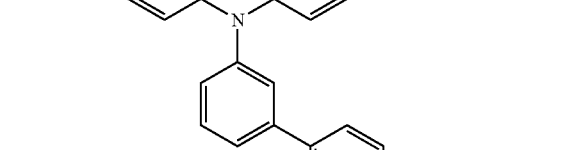
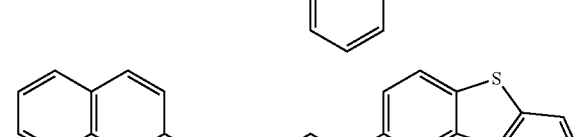
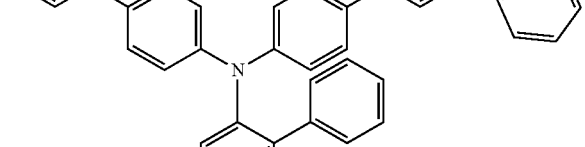

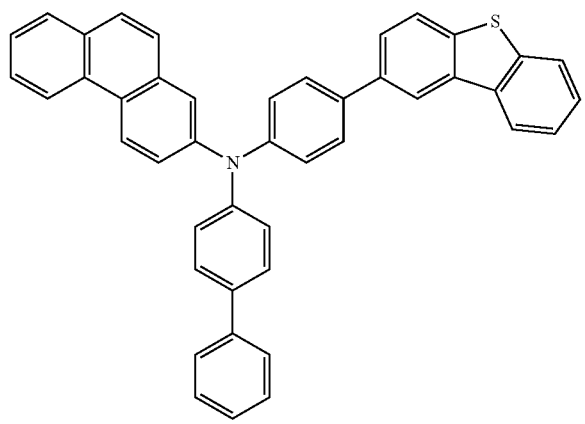
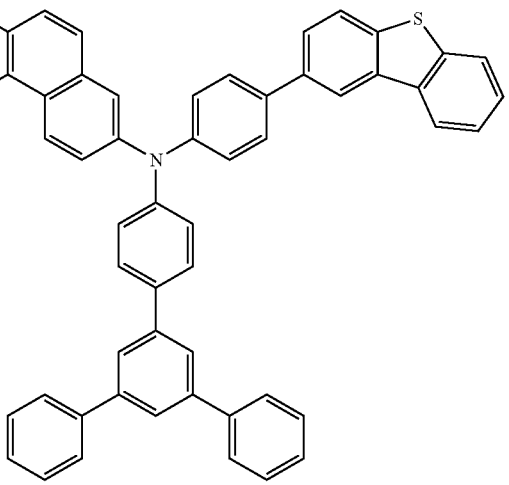
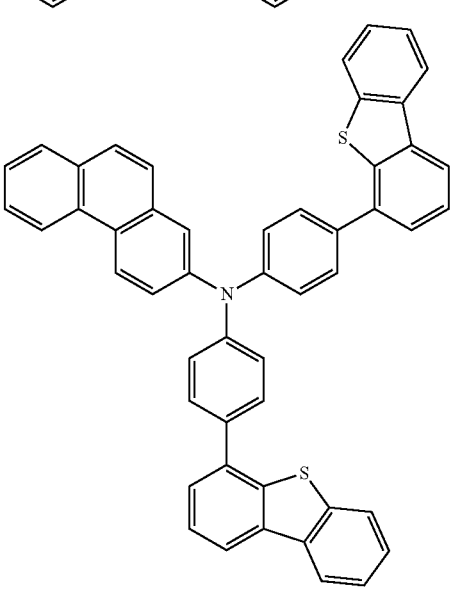
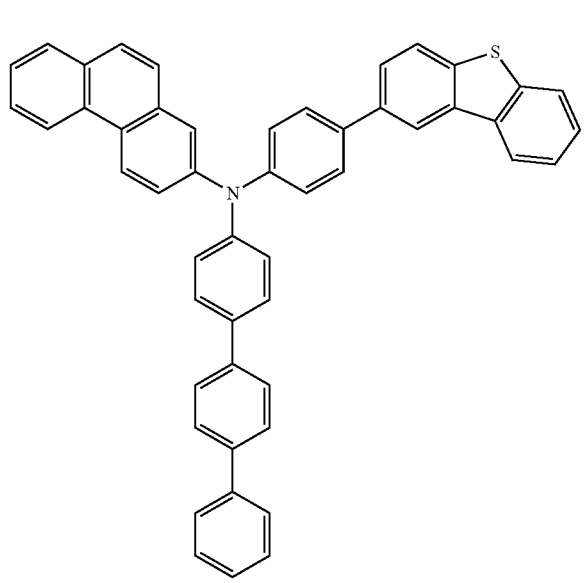
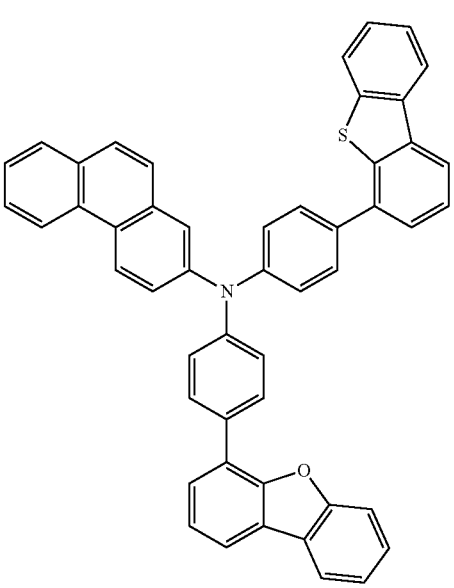

27
-continued
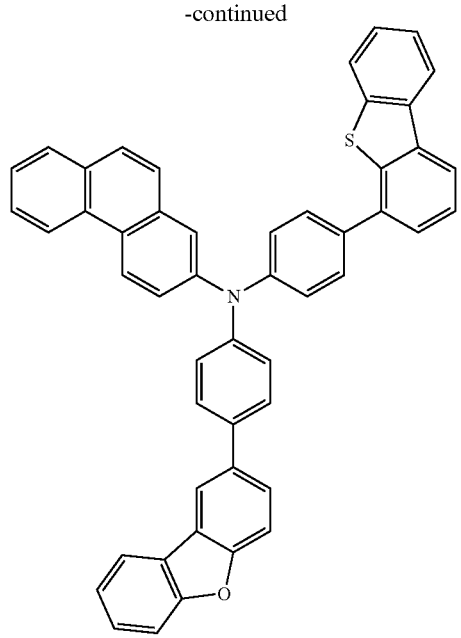
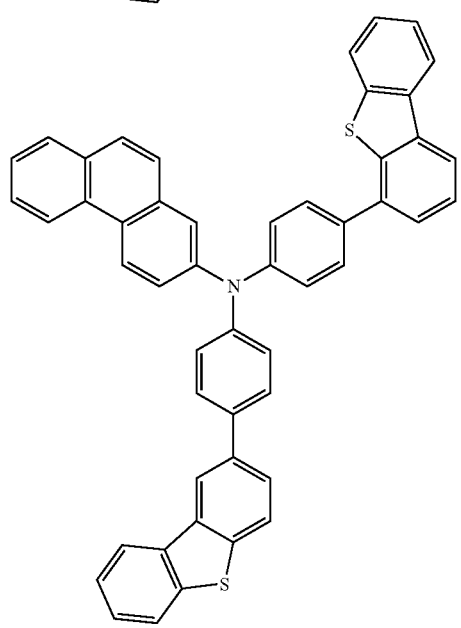
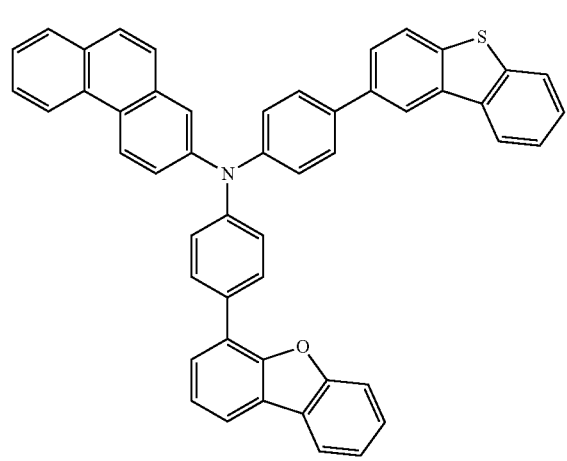
28
-continued
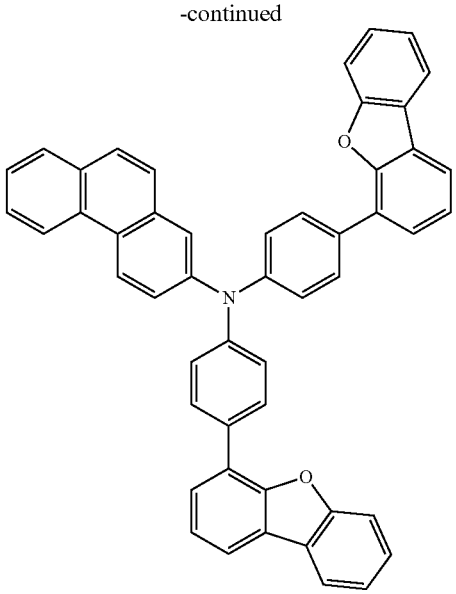
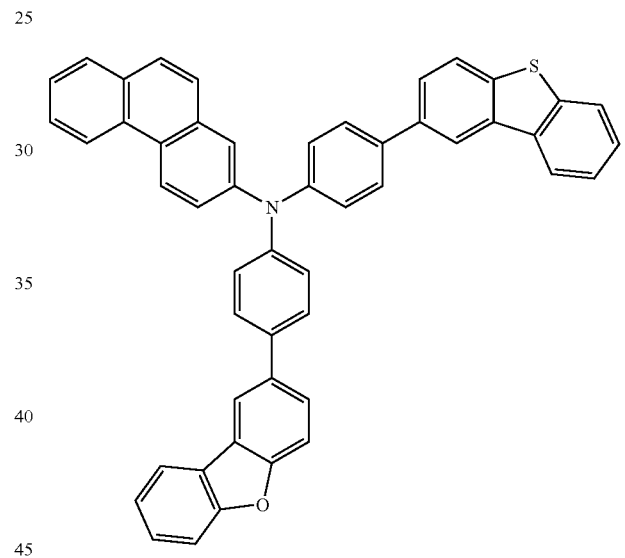
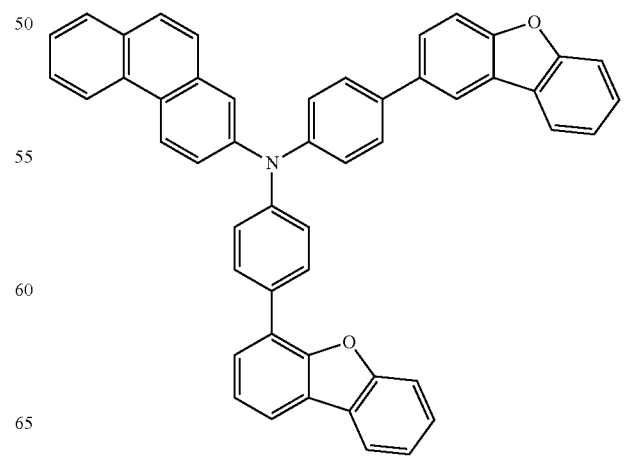

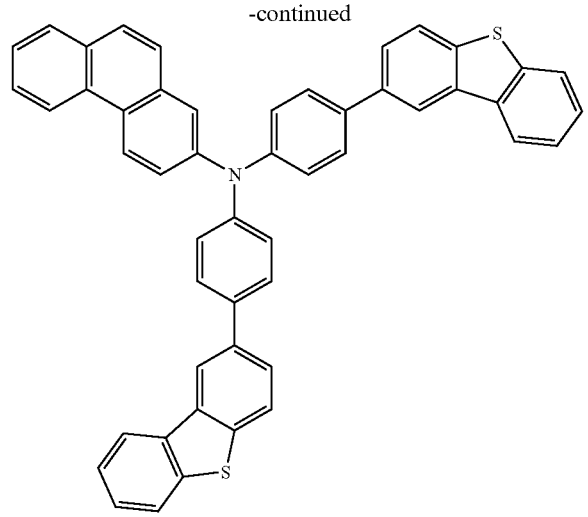
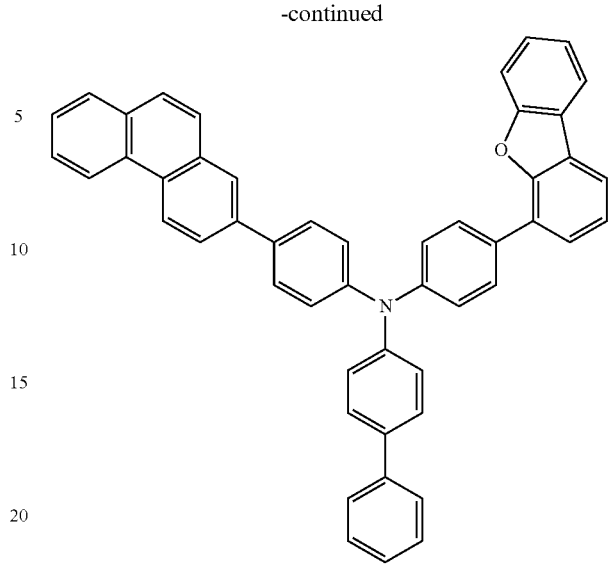
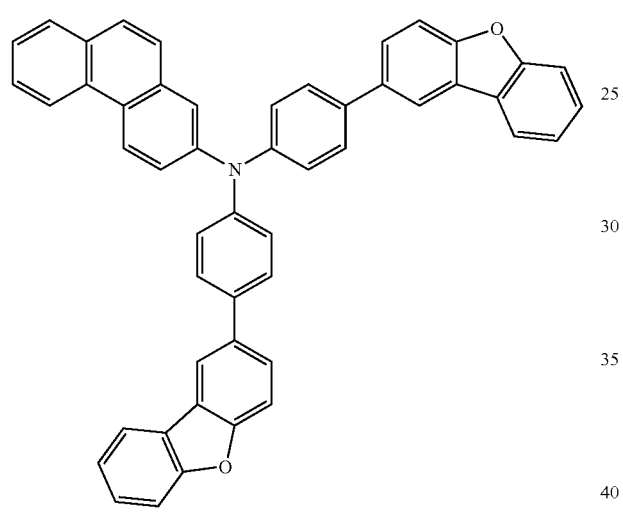
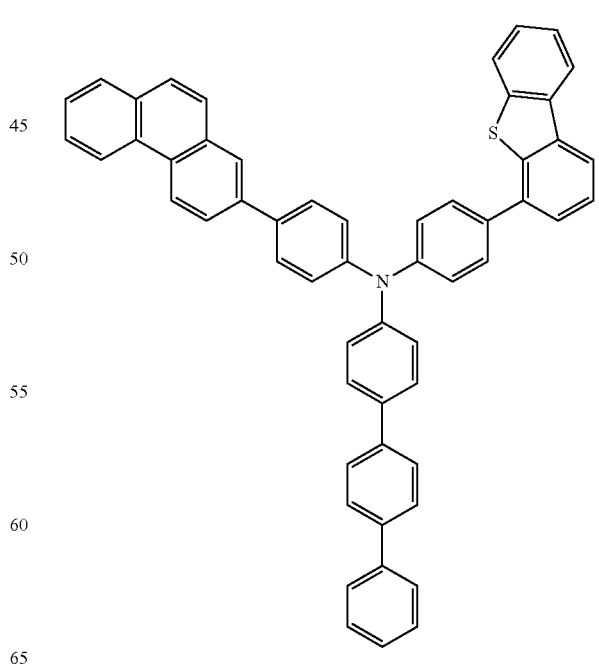

31
-continued
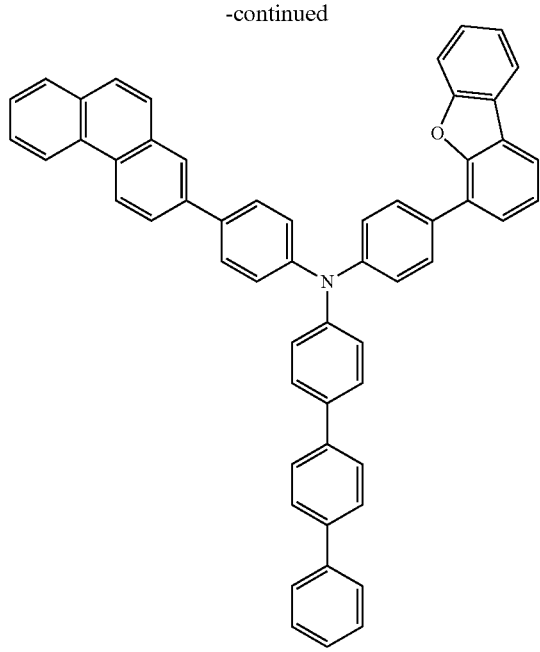
32
-continued
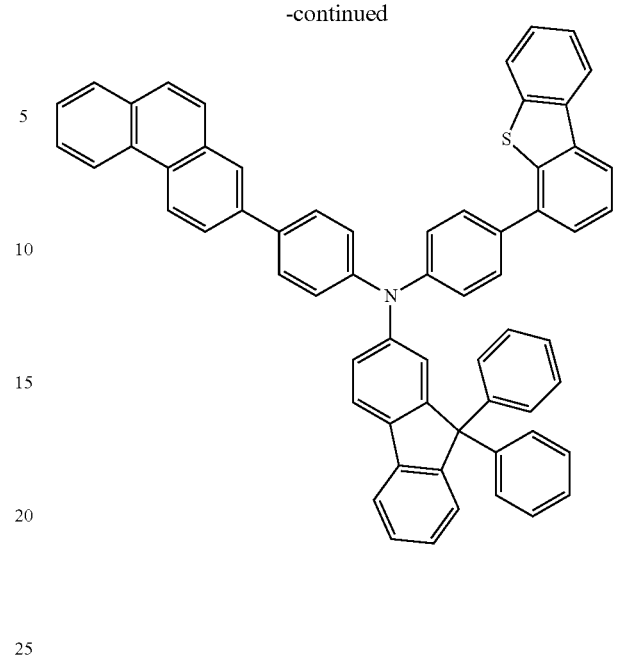
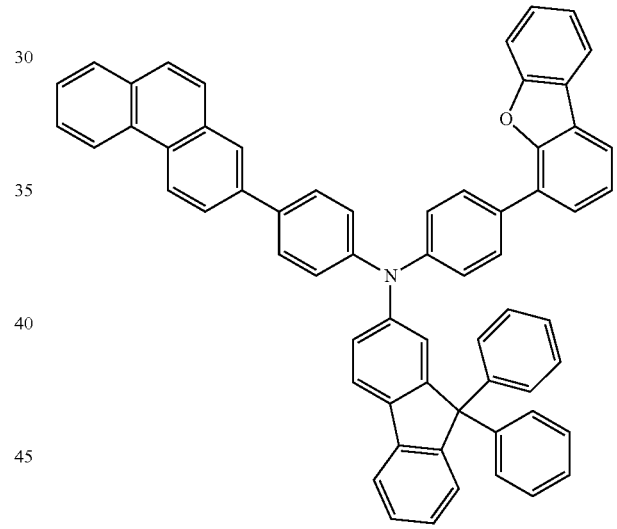
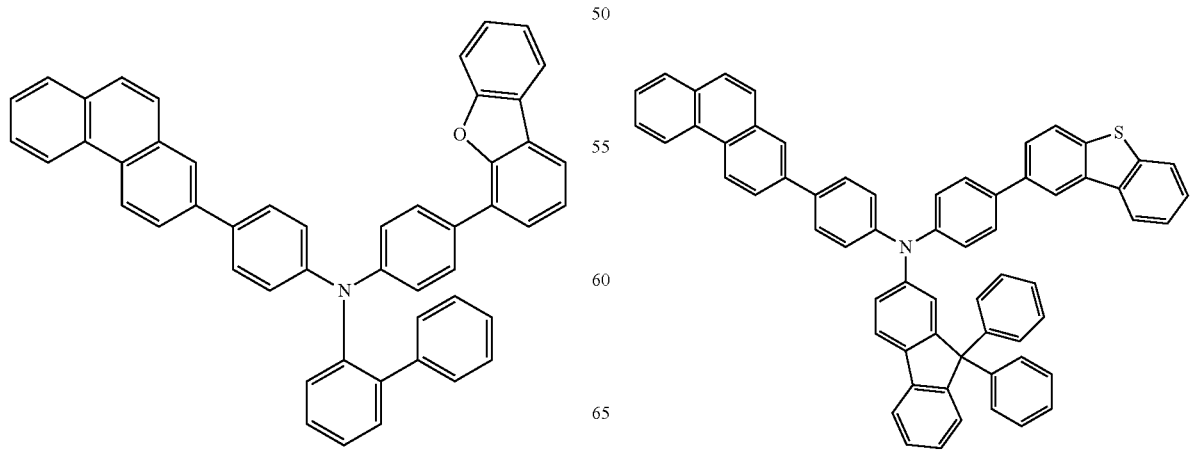

33
-continued
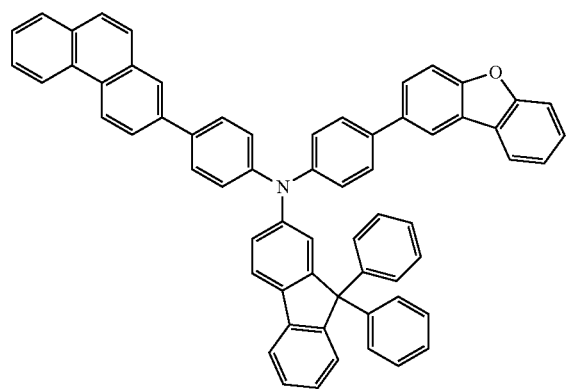
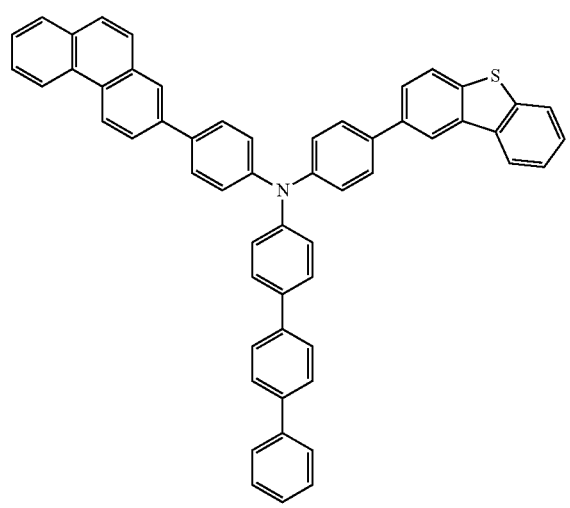
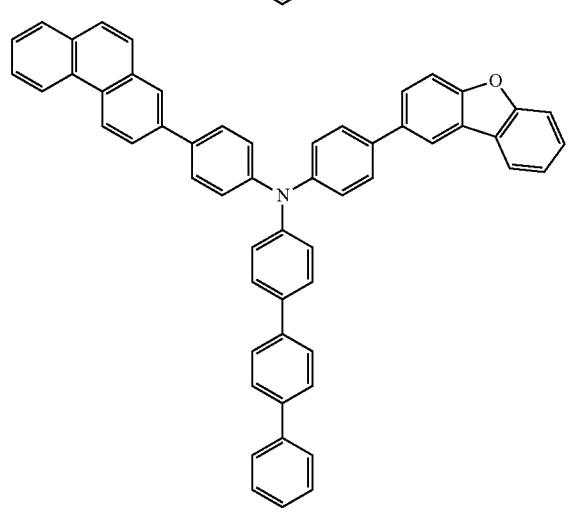
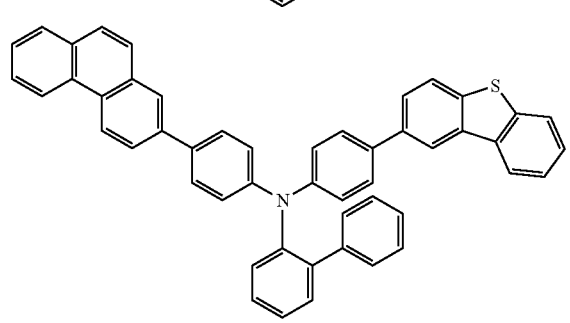
34
-continued
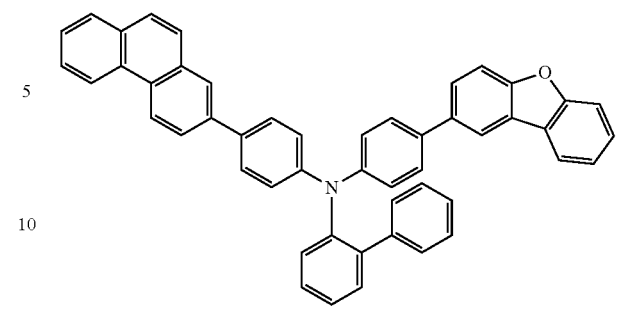
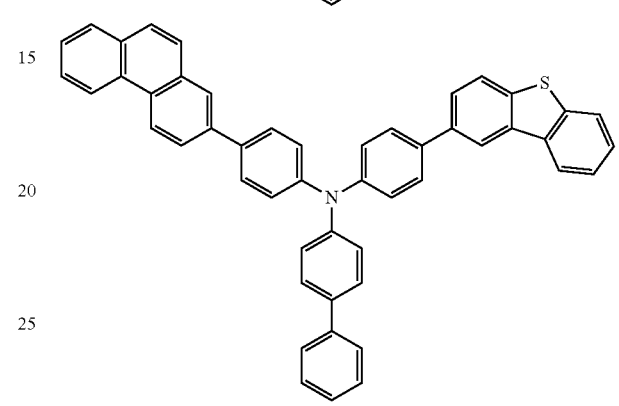
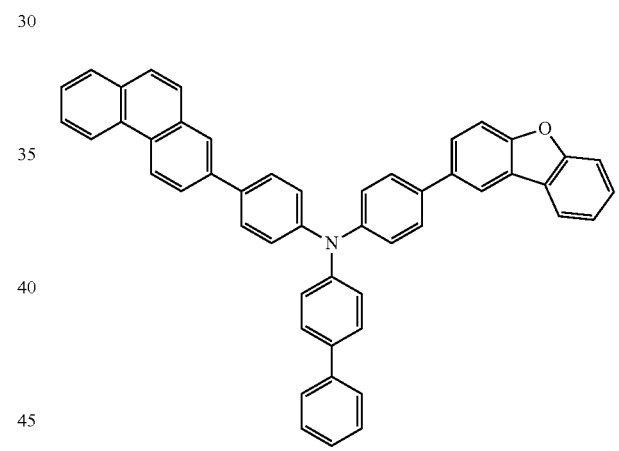
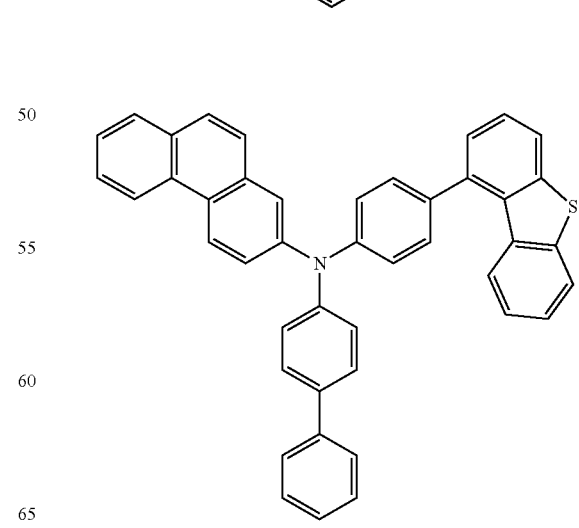

35
-continued
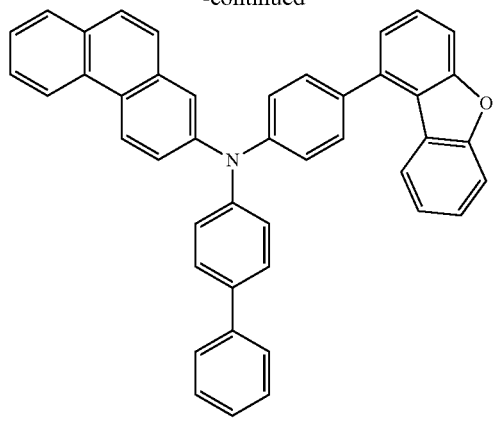
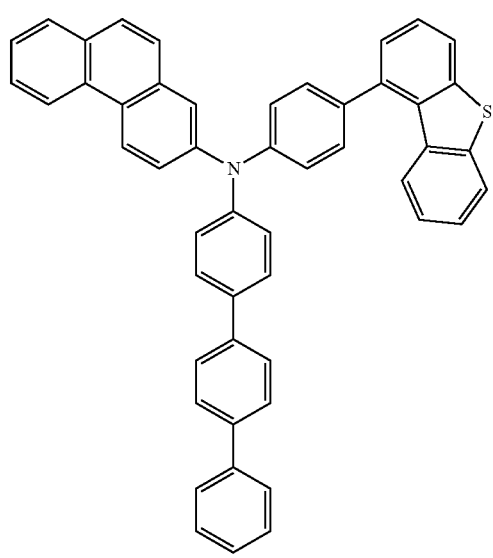
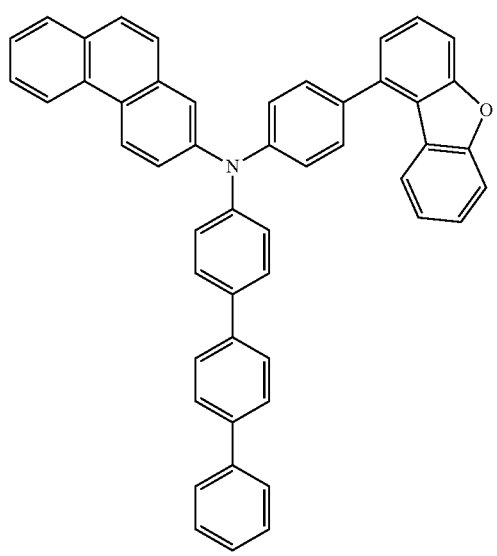
36
-continued
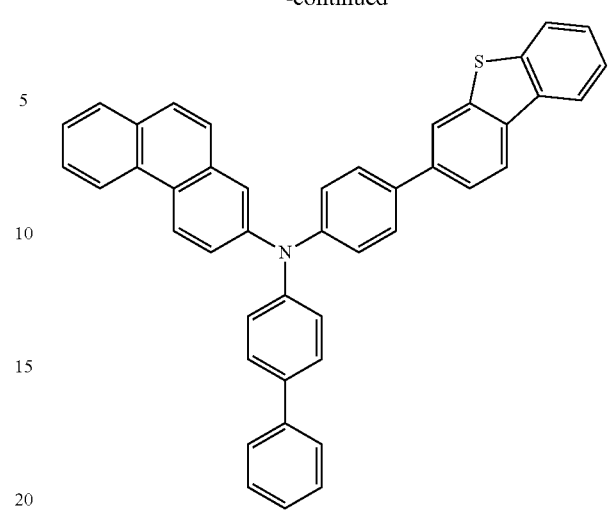
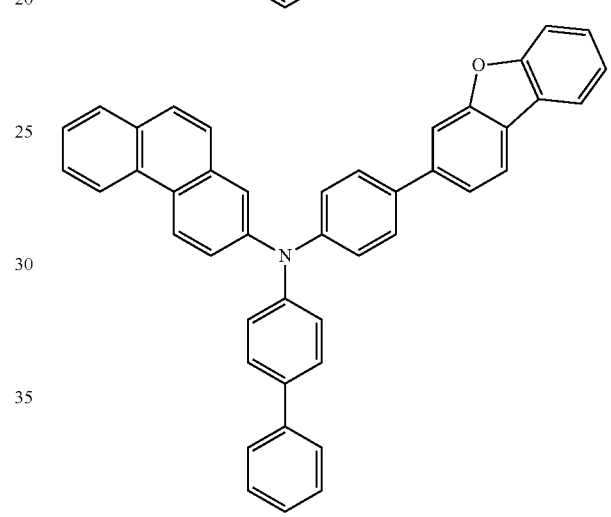
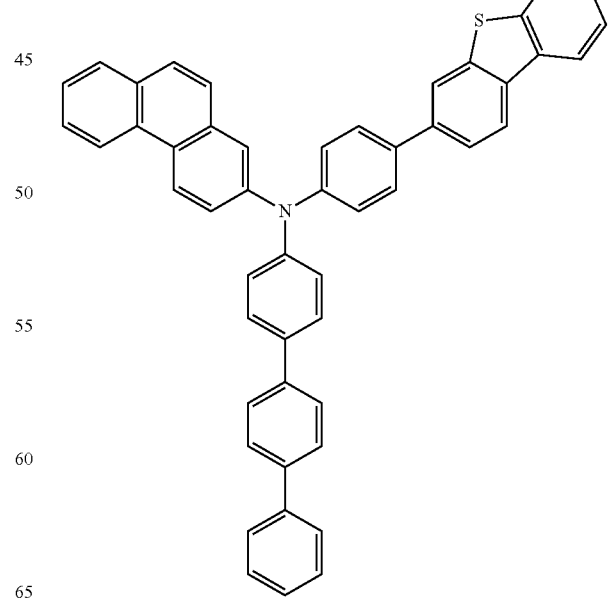

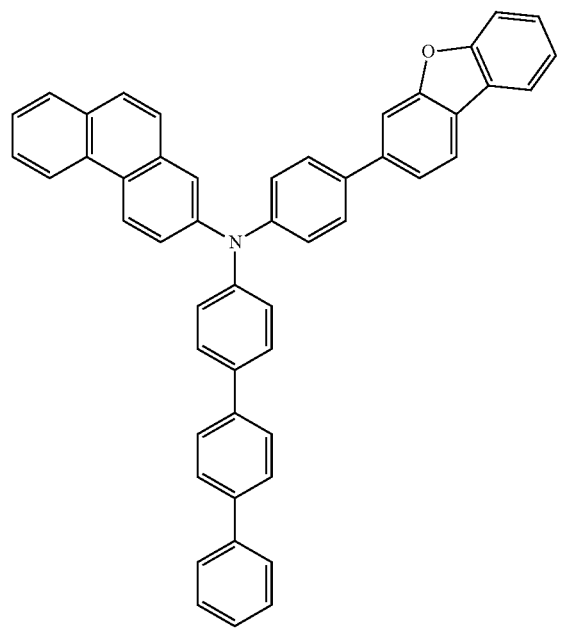
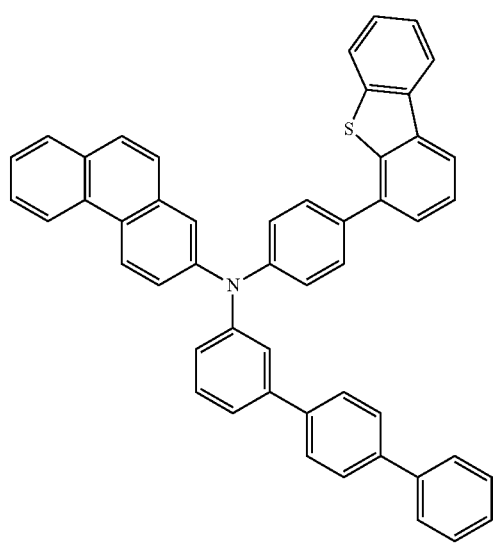
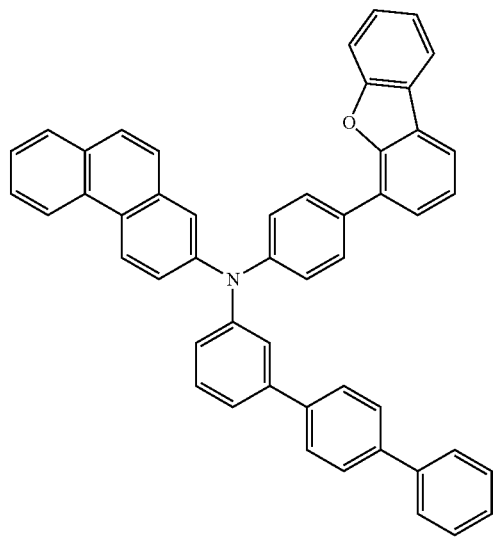
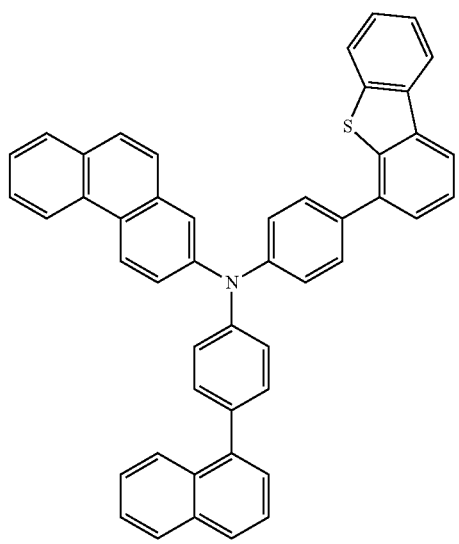
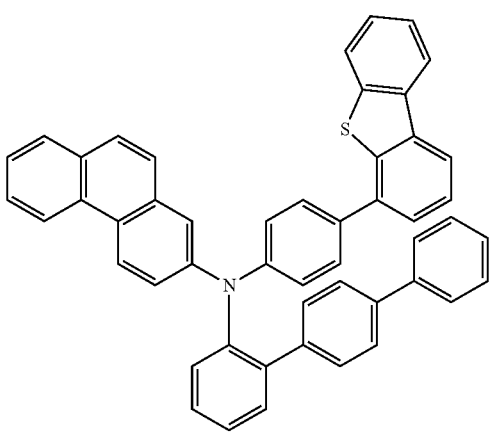
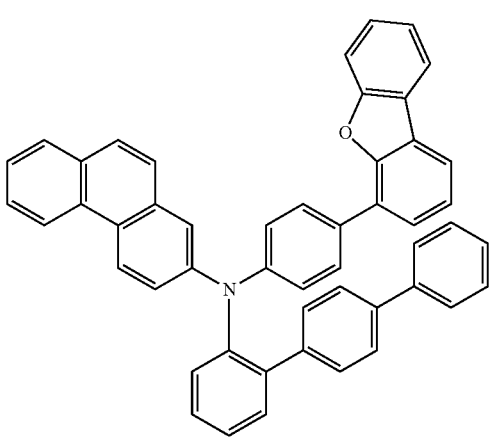

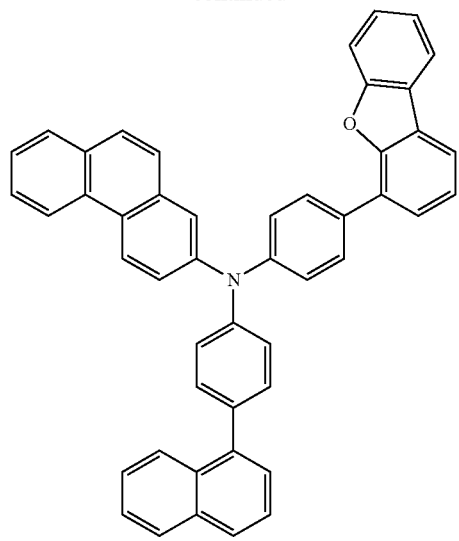
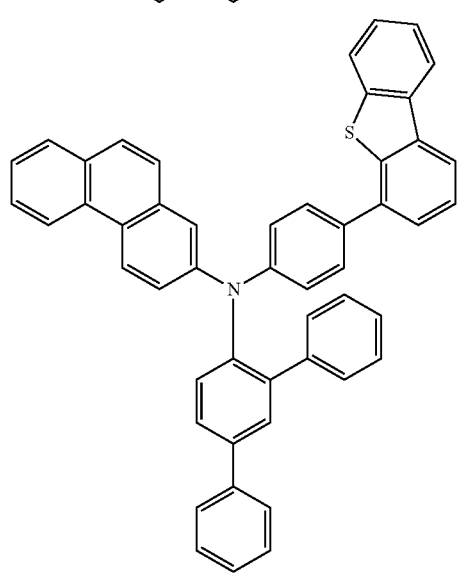
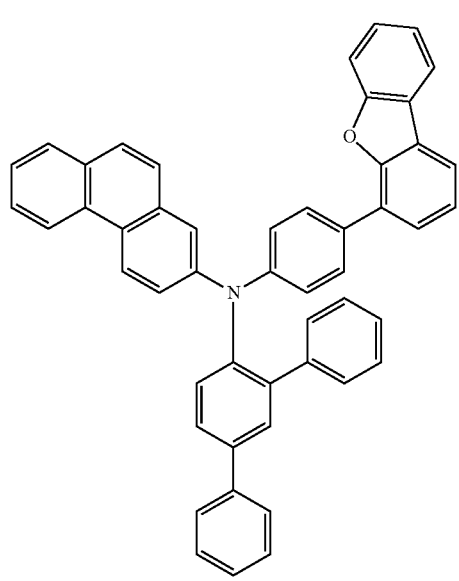
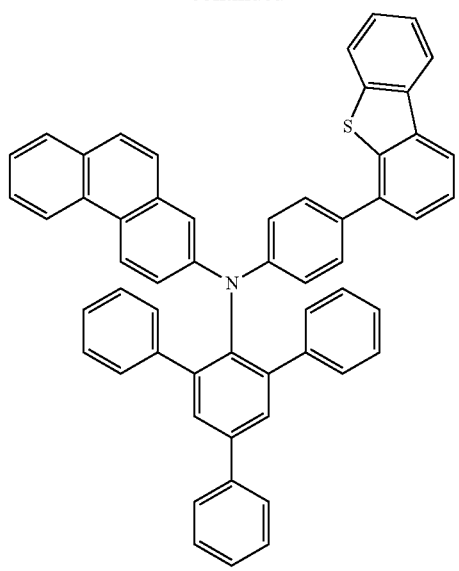
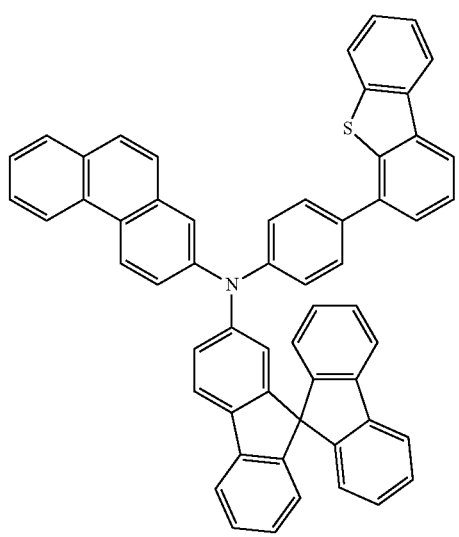
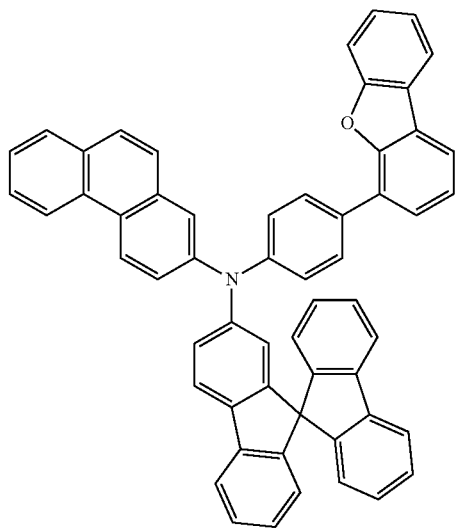

41
-continued
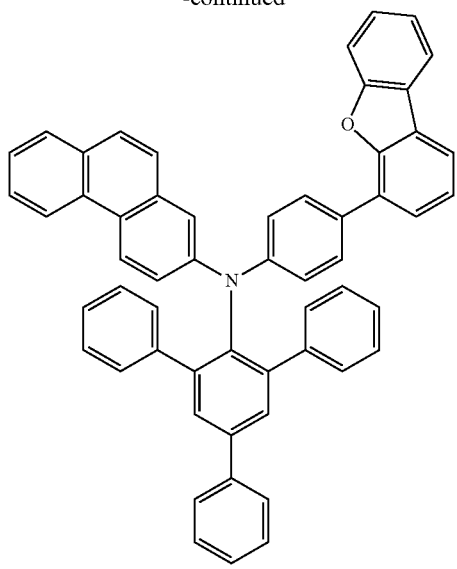
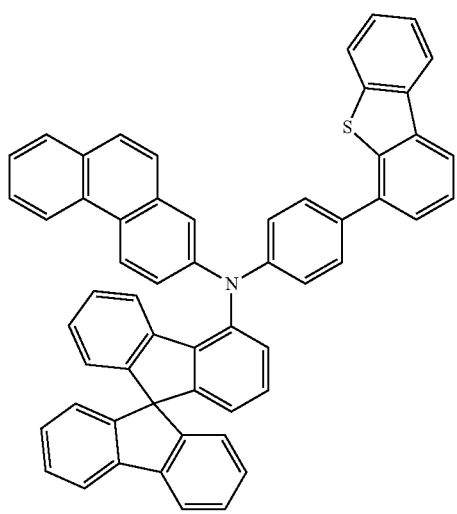
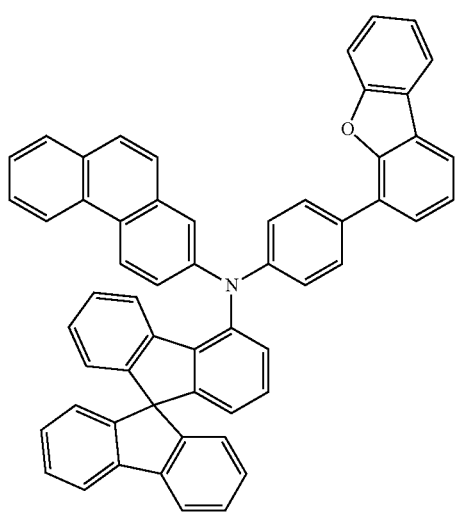
42
-continued
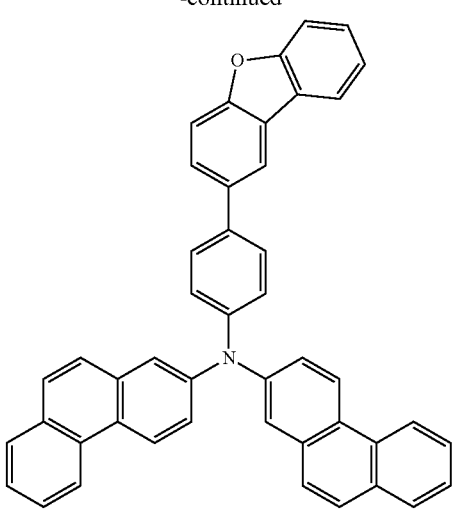
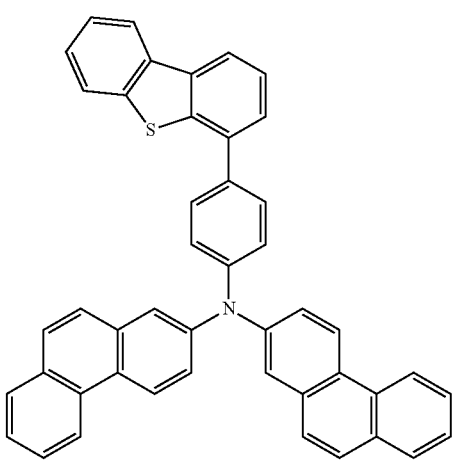
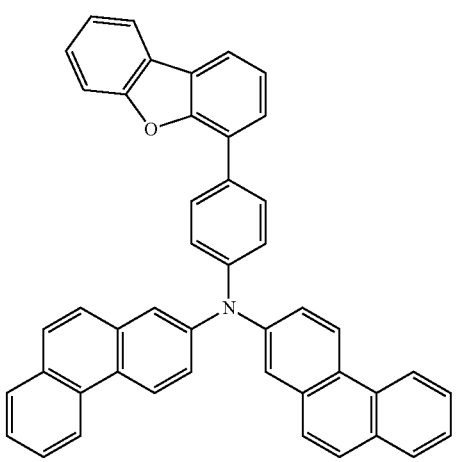

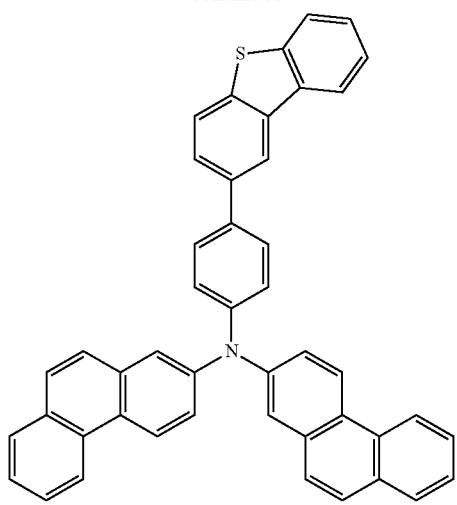
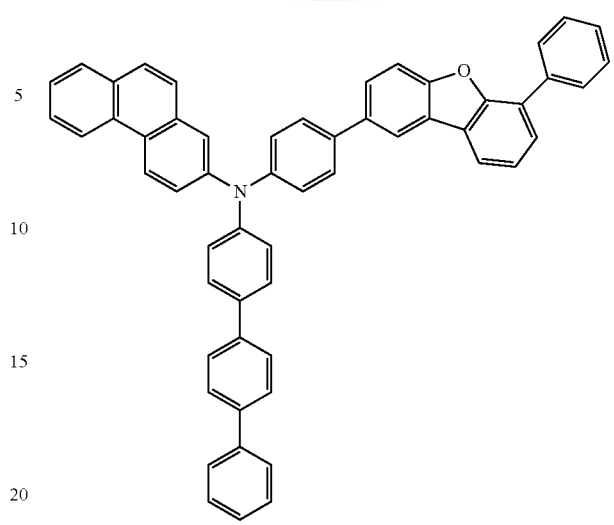
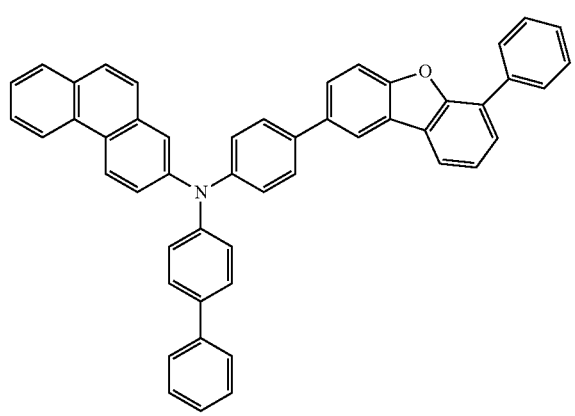
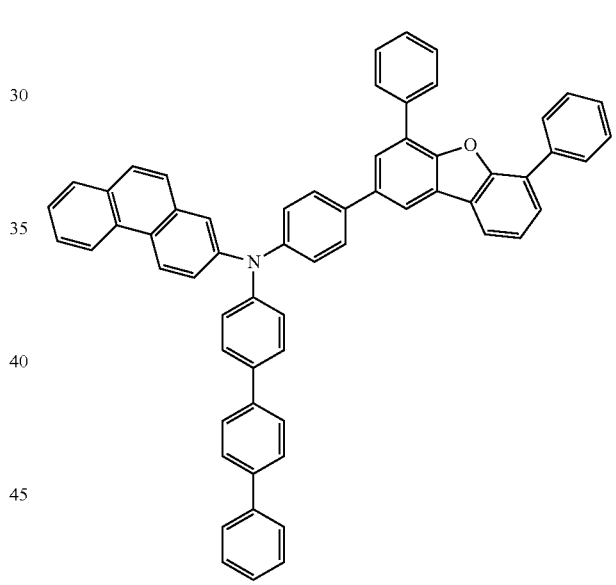
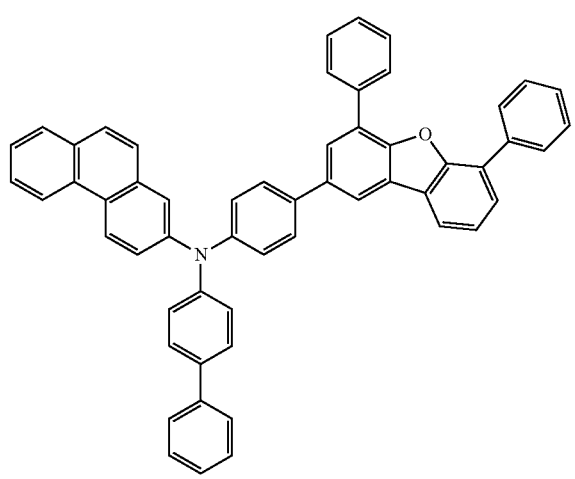
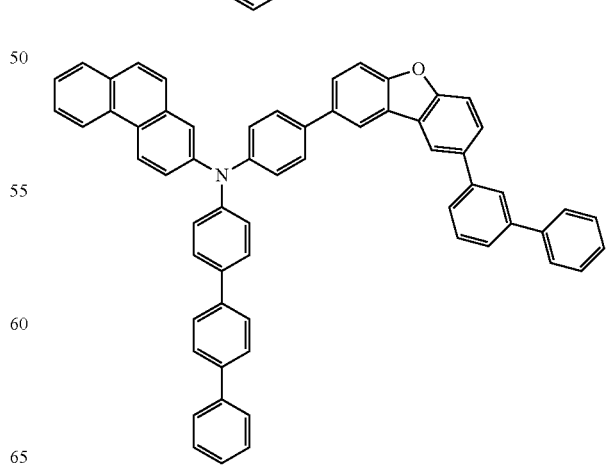

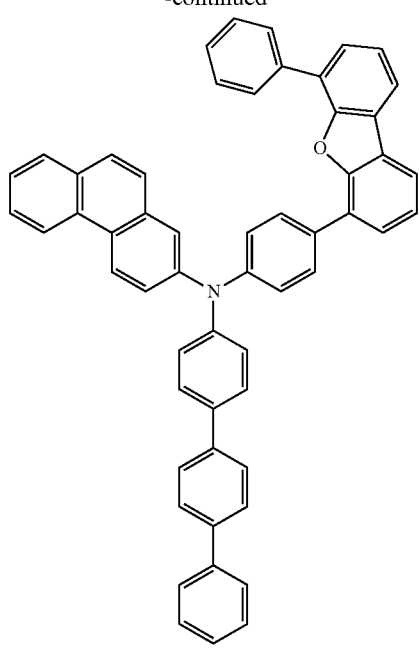
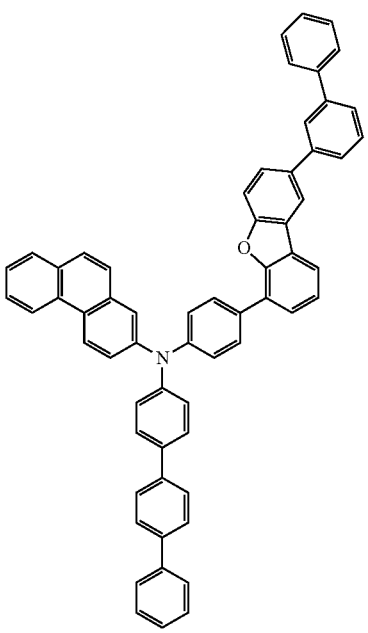
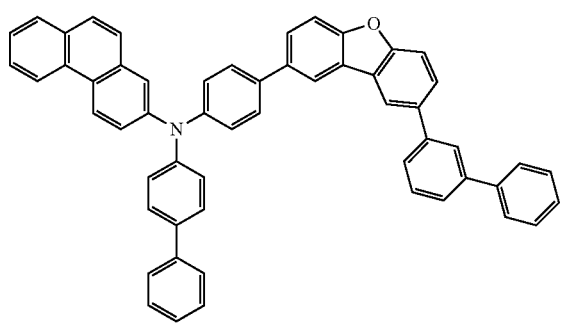
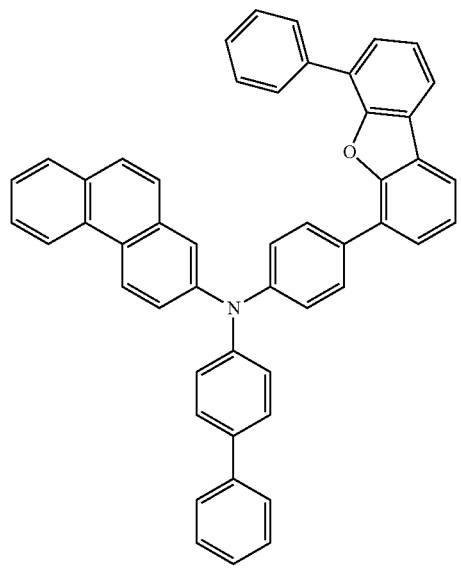
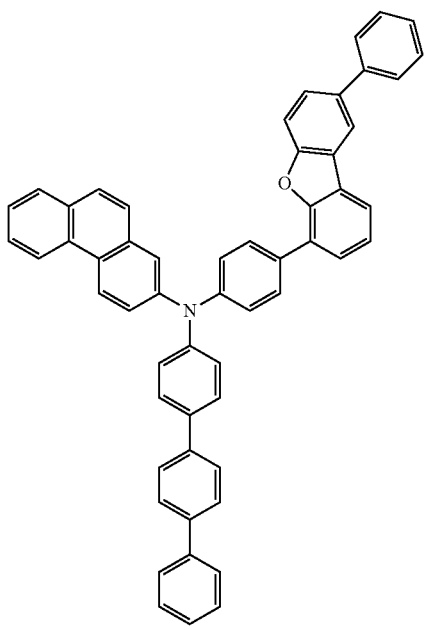

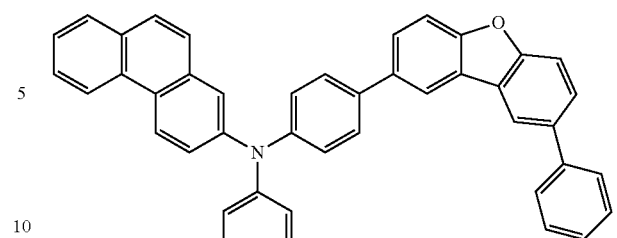
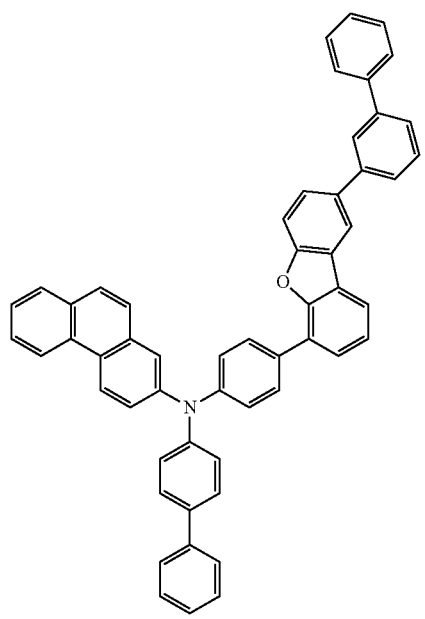

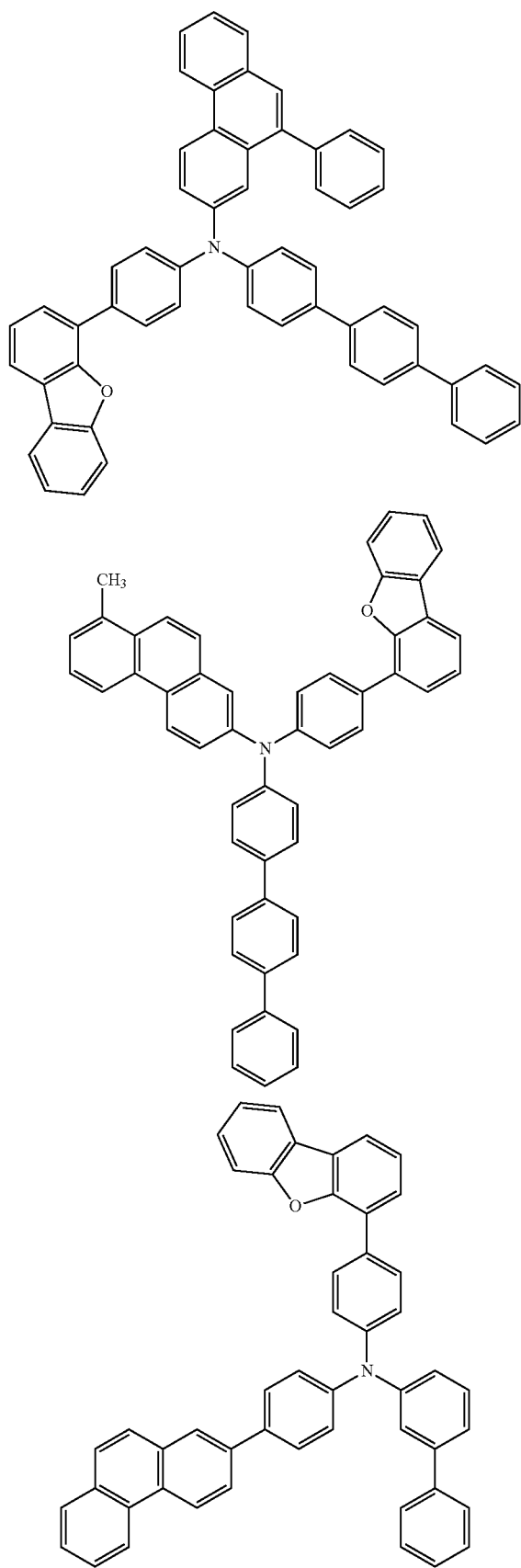
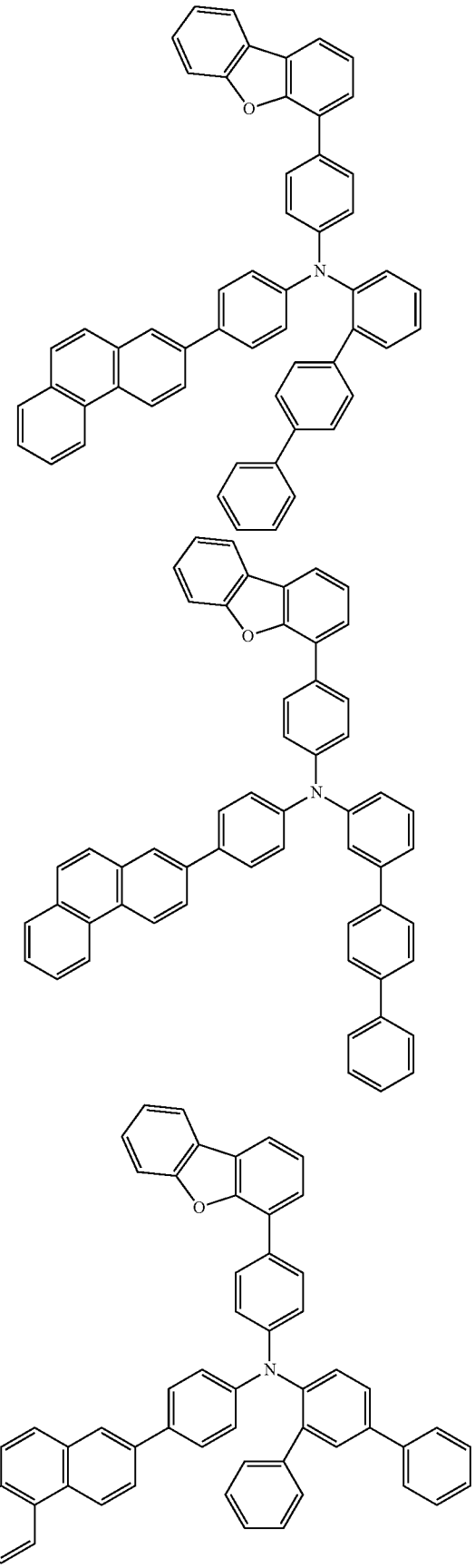

51
-continued
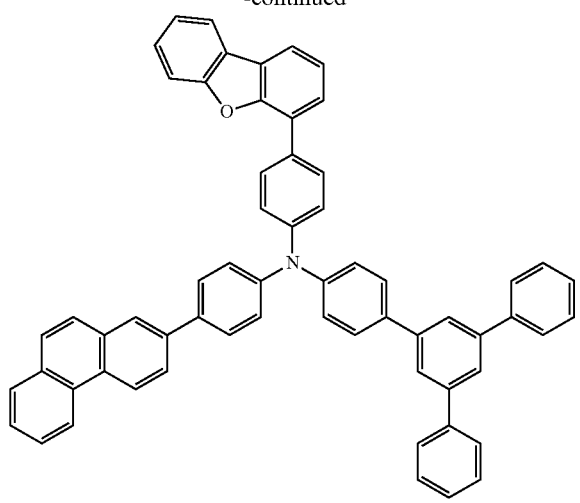
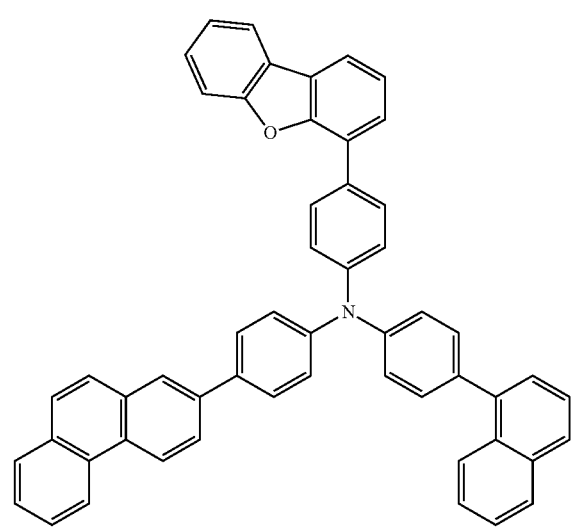
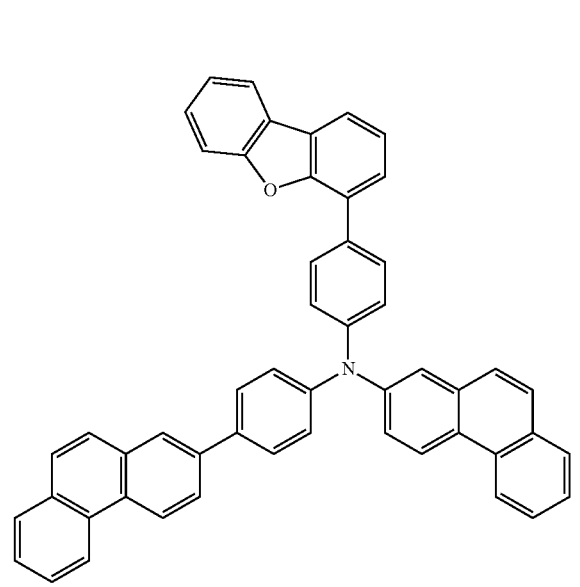
52
-continued
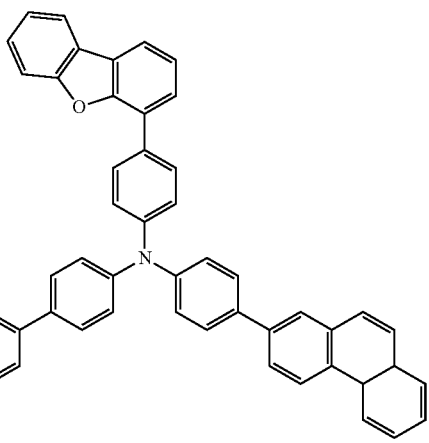
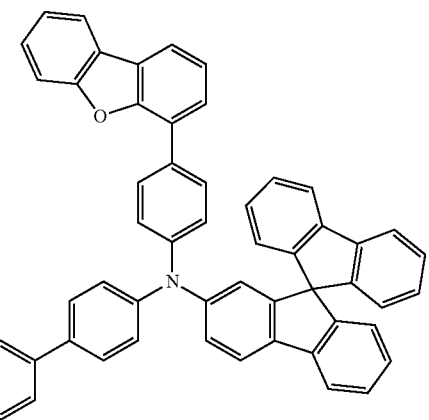
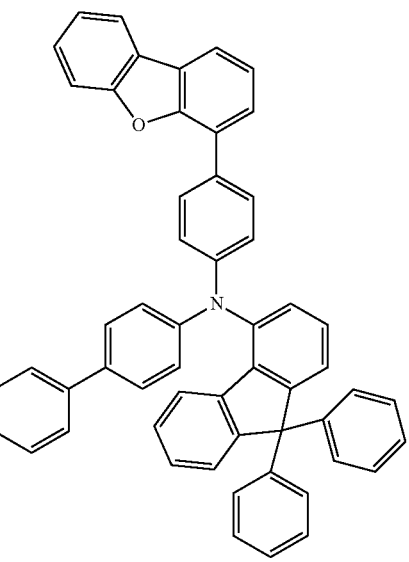

53
-continued
54
-continued
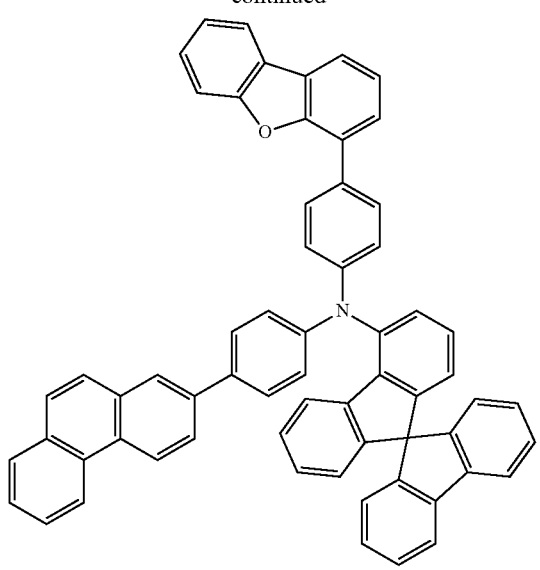
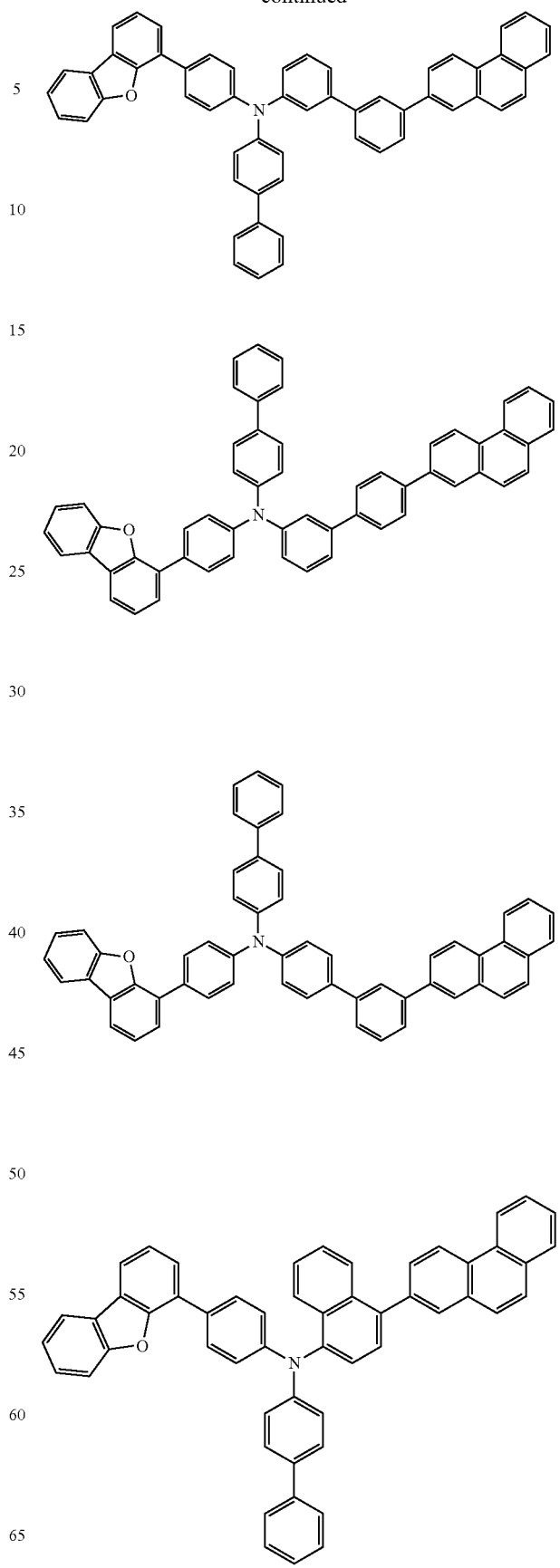

-continued
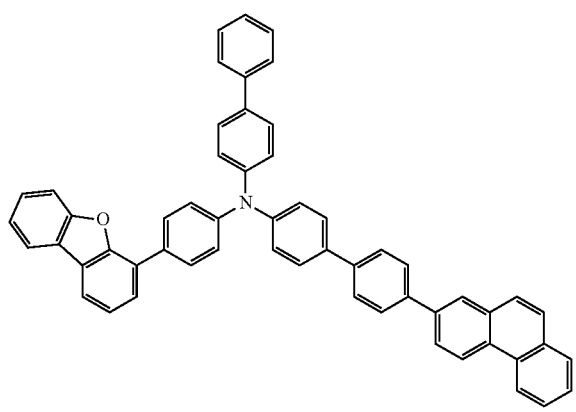
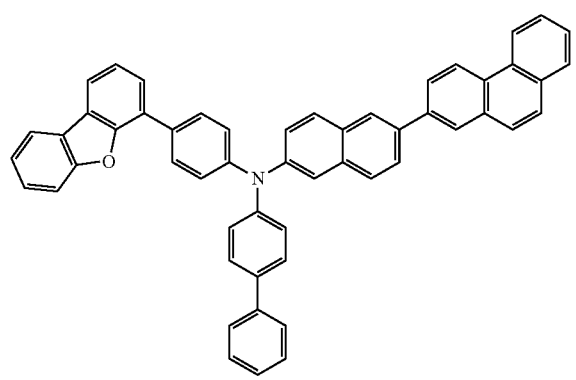
-continued
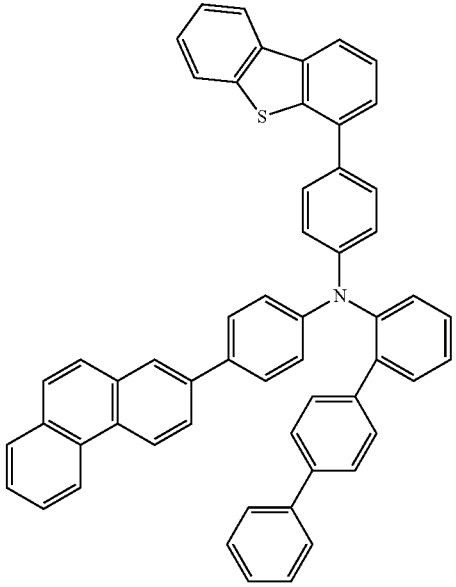
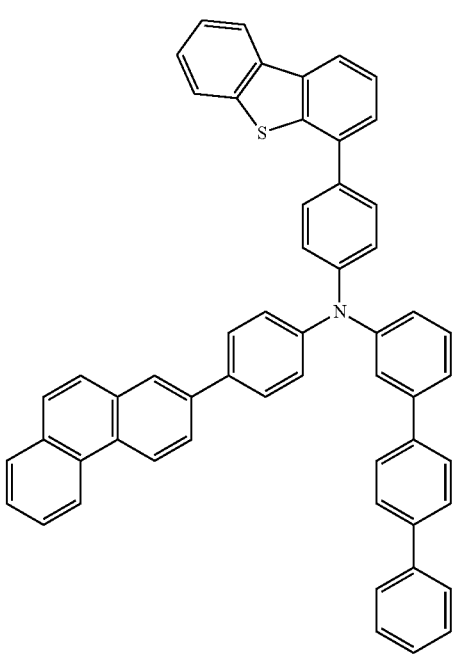

57
-continued
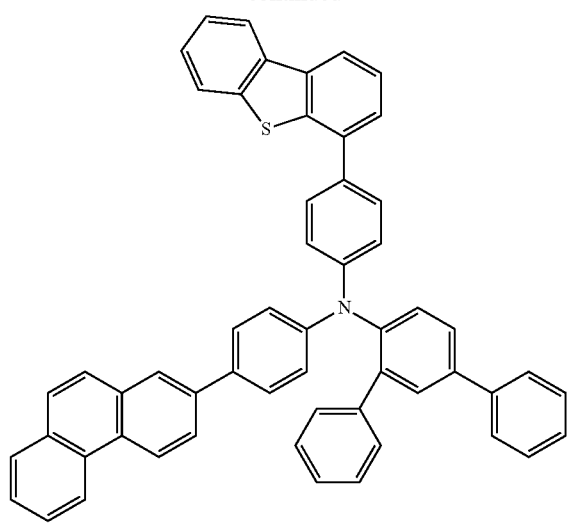
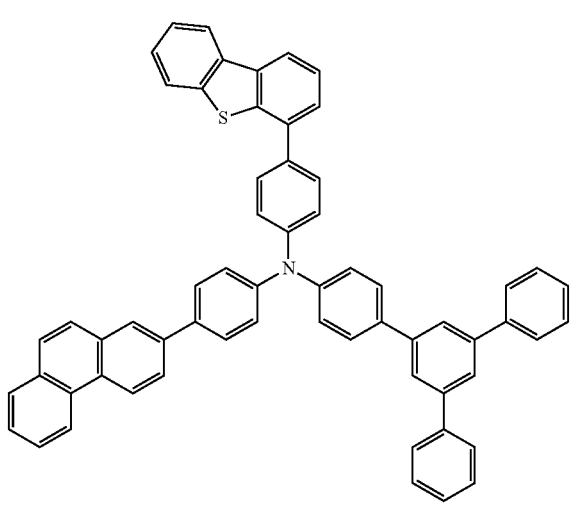
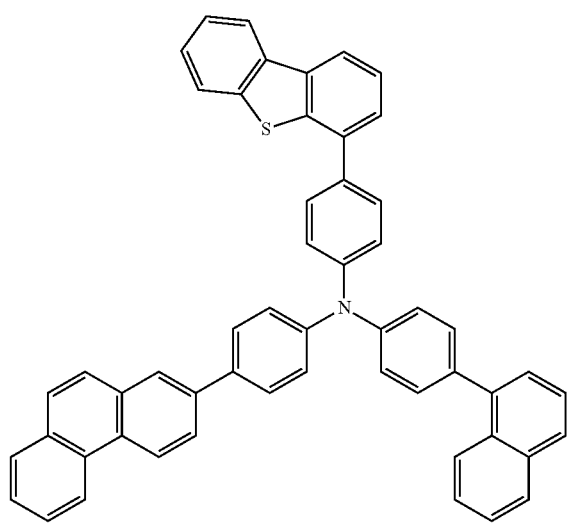
58
-continued
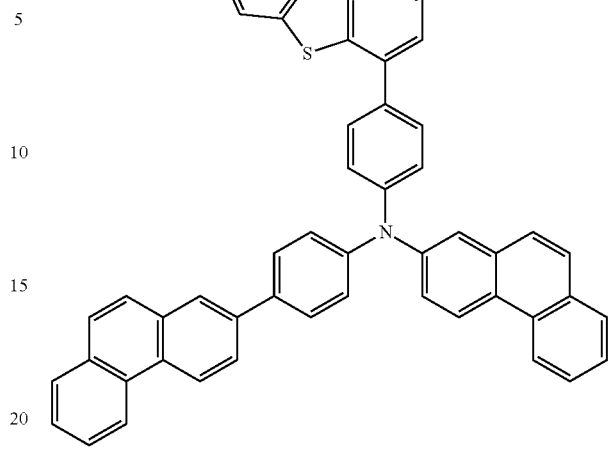
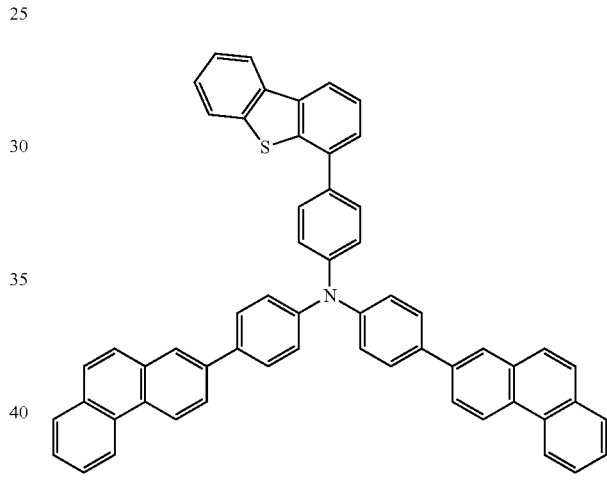
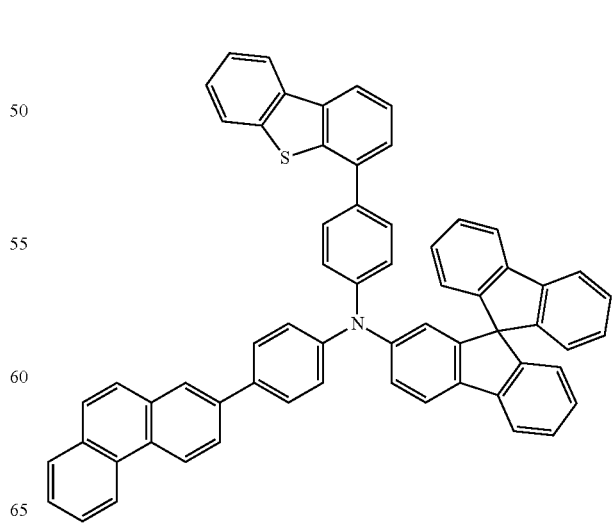

59
-continued
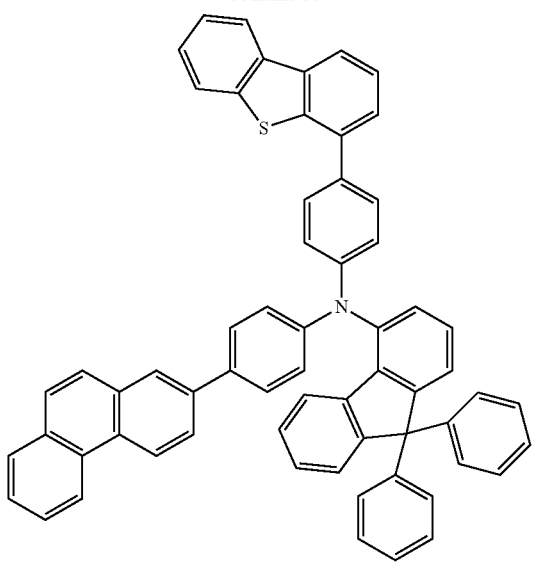
60
-continued
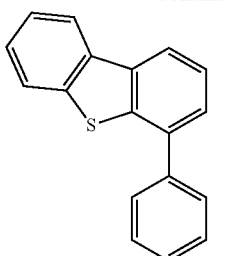
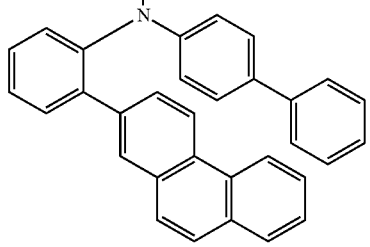
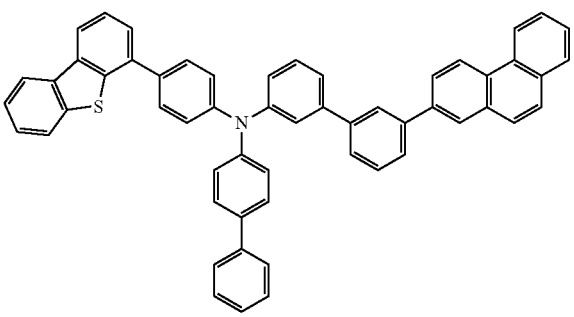
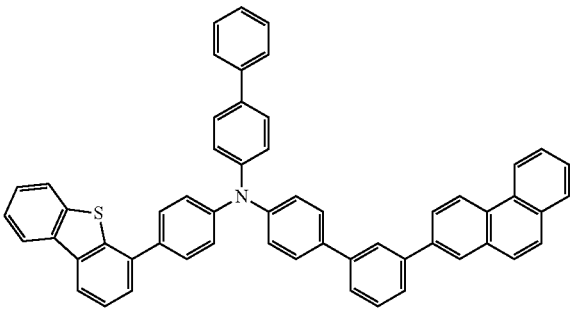
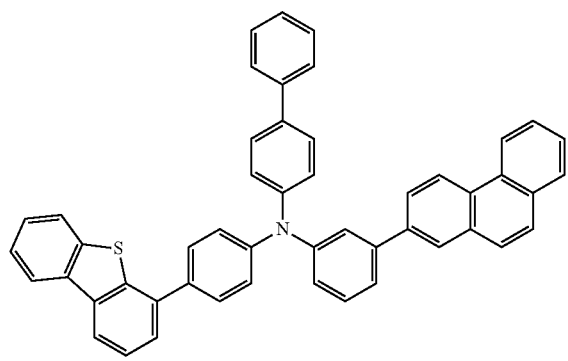
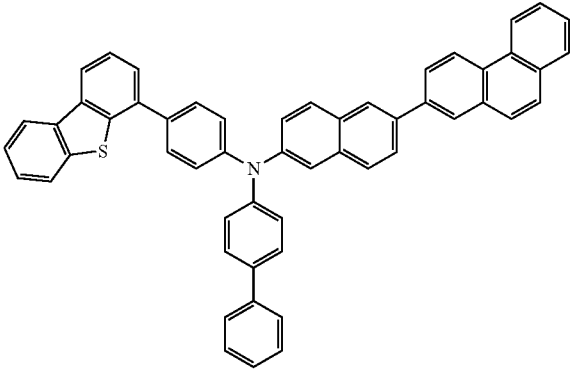

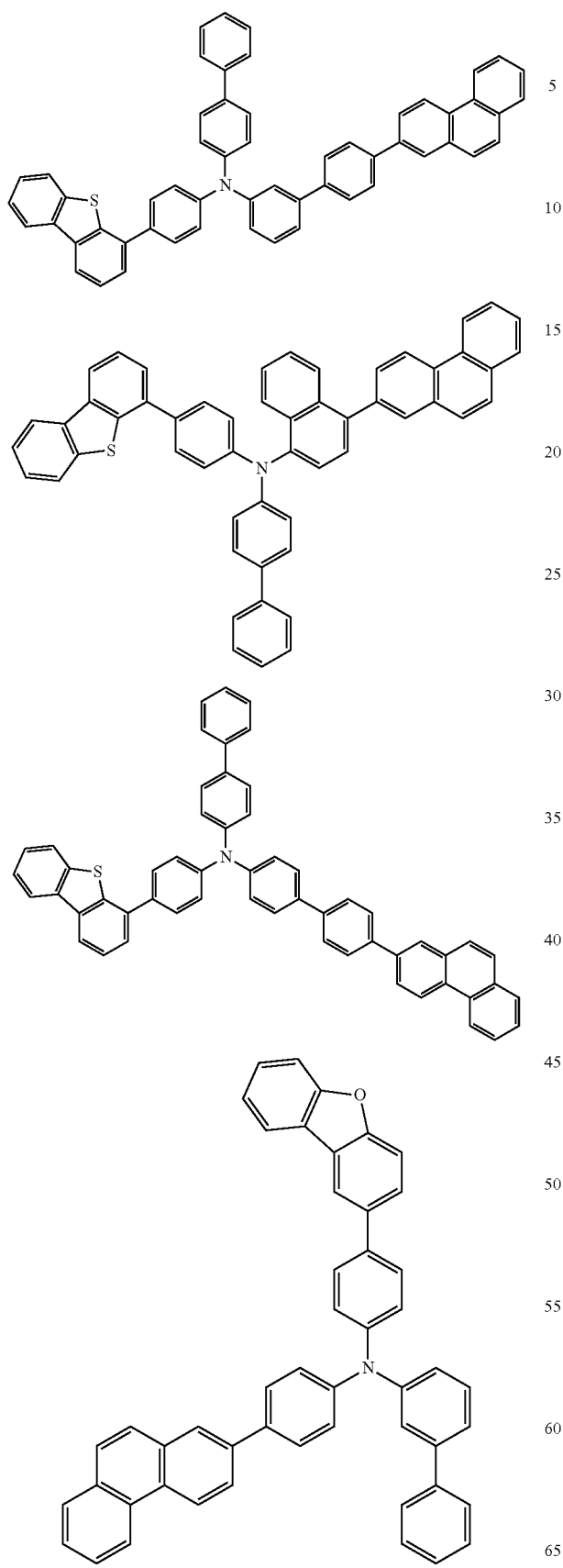
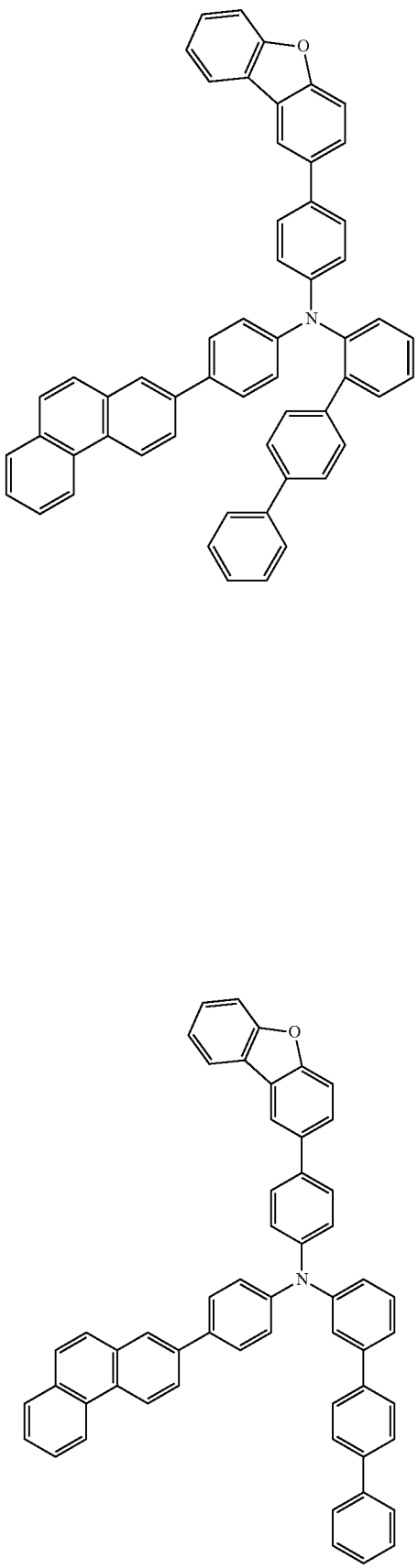

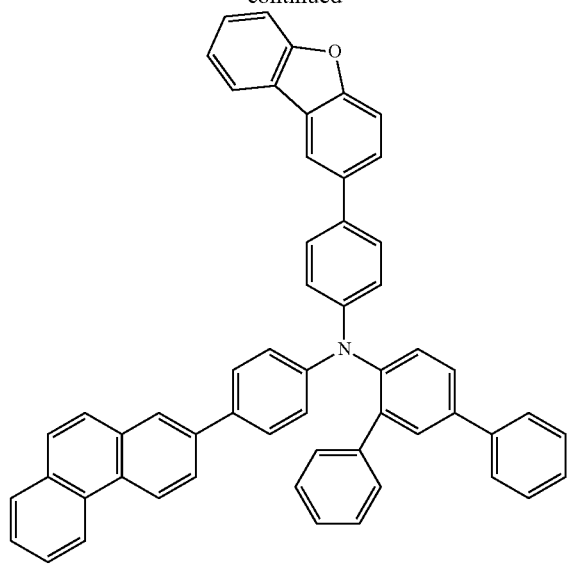
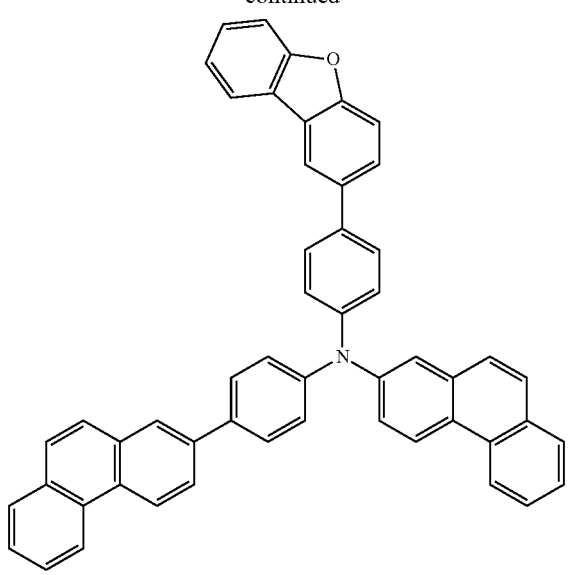
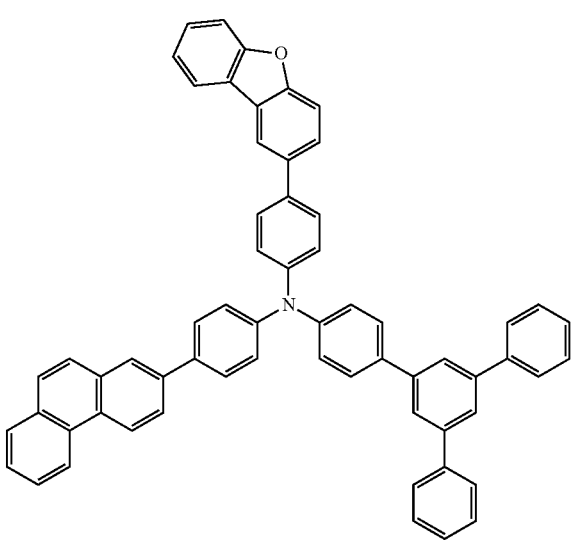
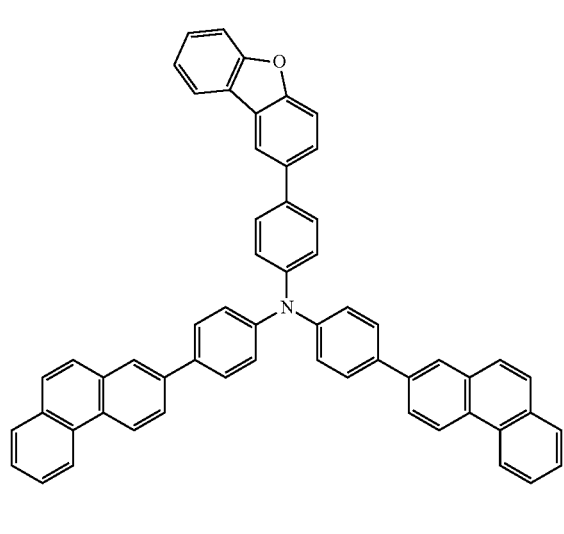
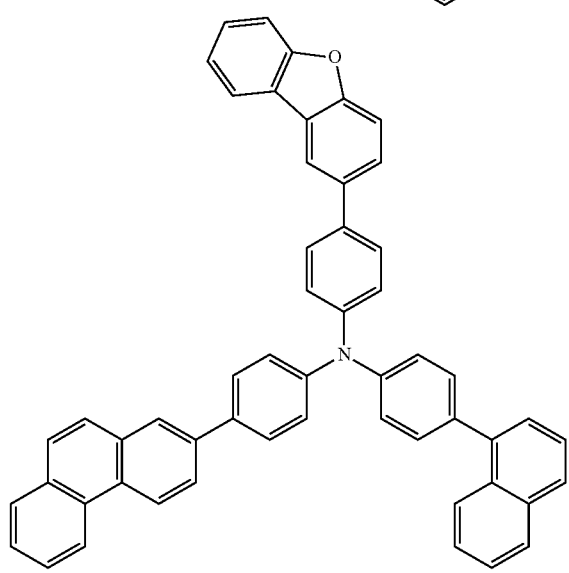
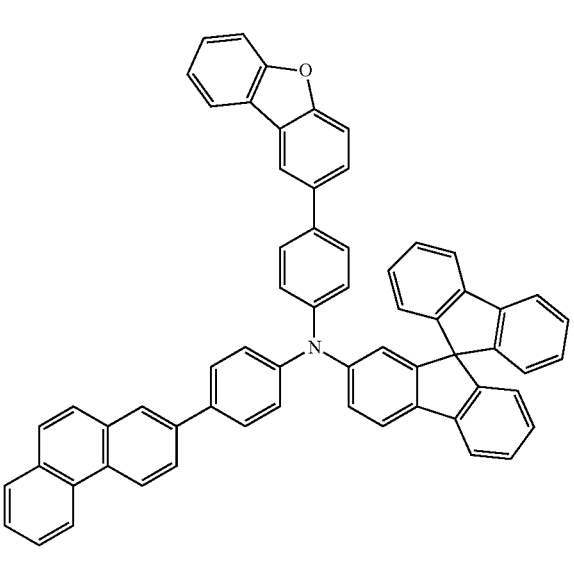

65
-continued
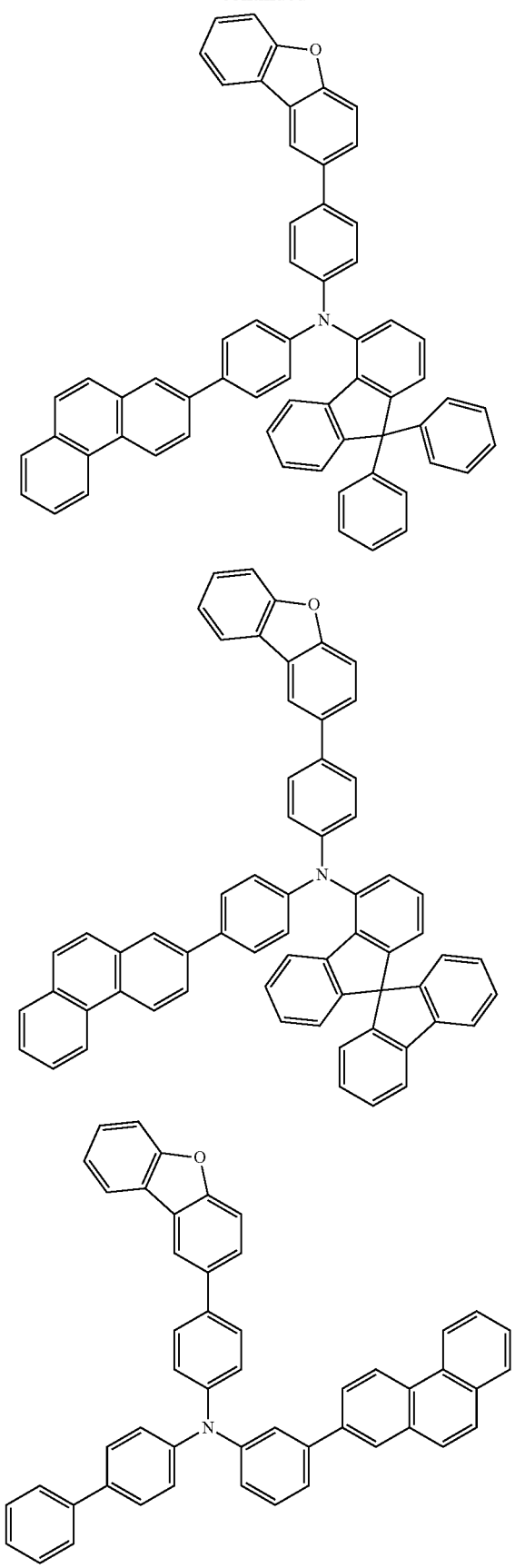
66
-continued
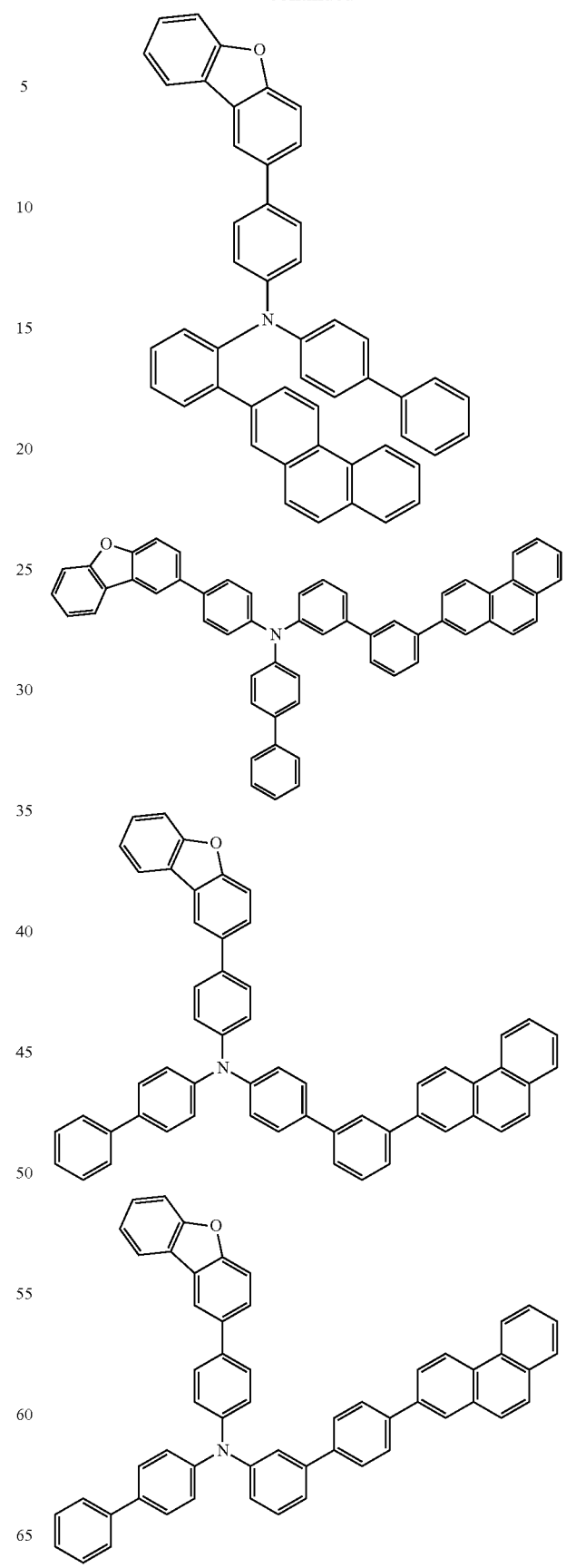

67
-continued
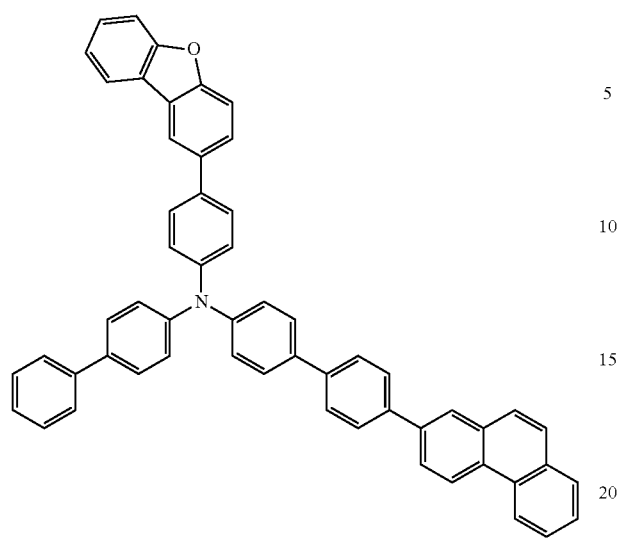
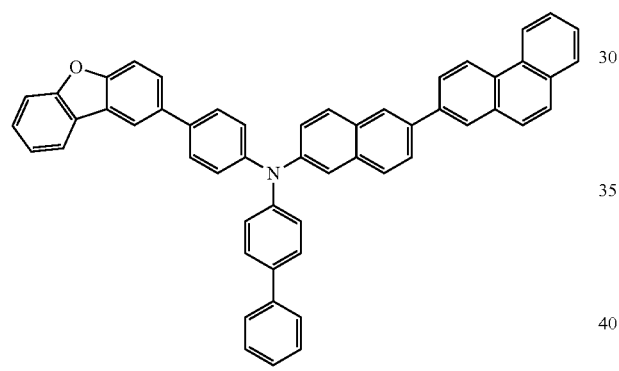
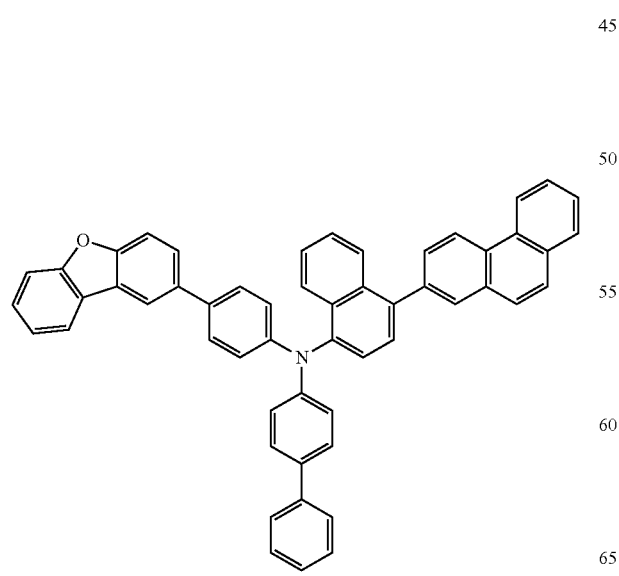
68
-continued
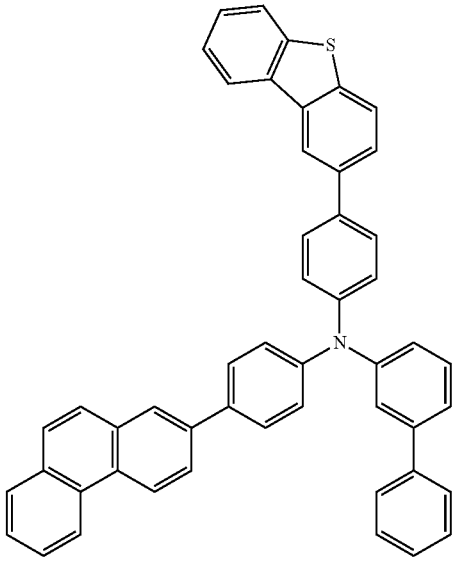
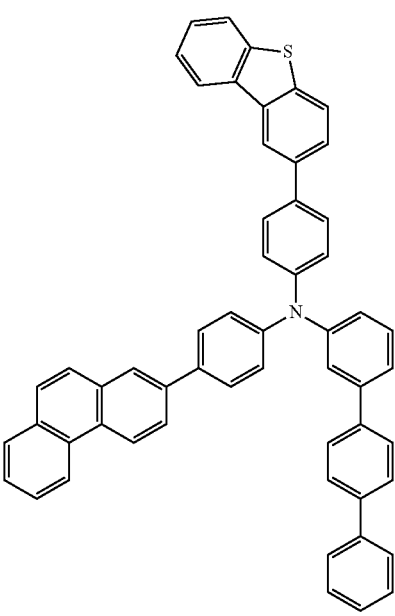

-continued
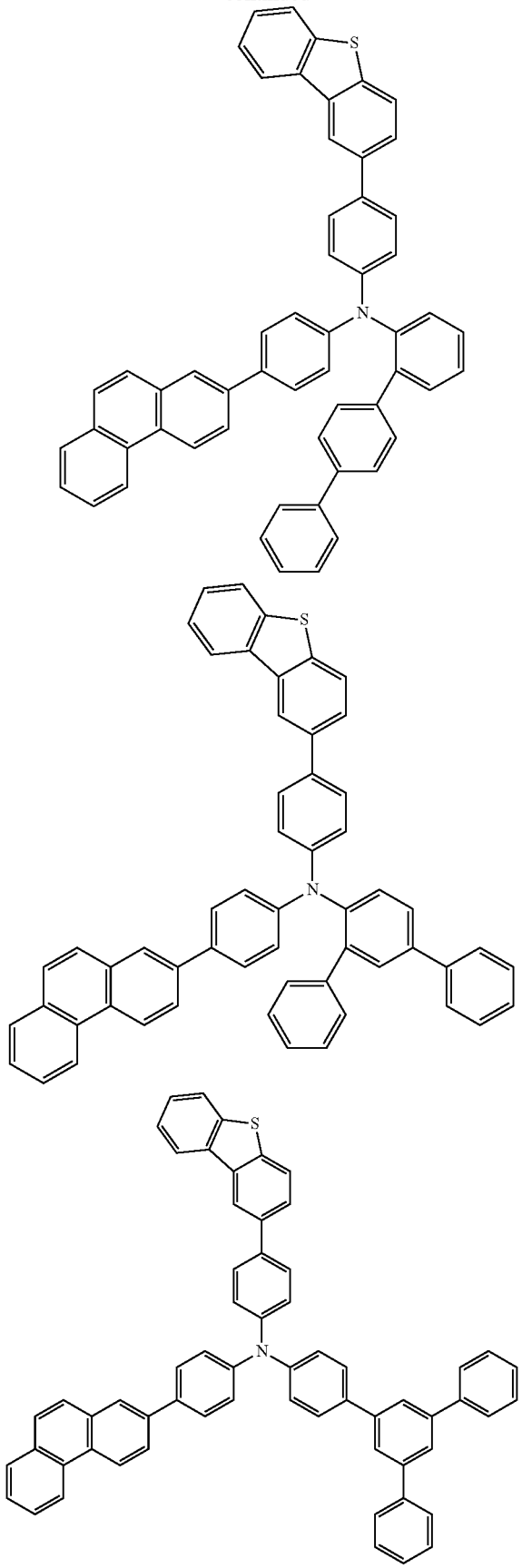
-continued
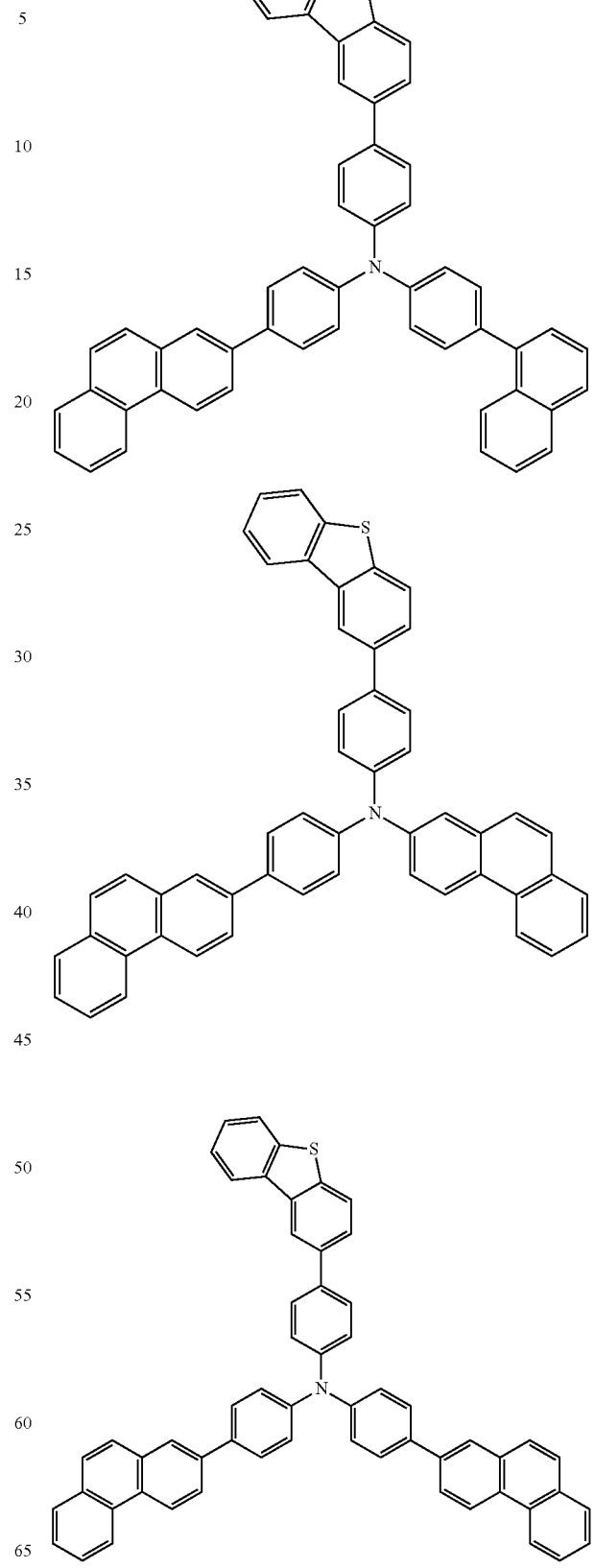

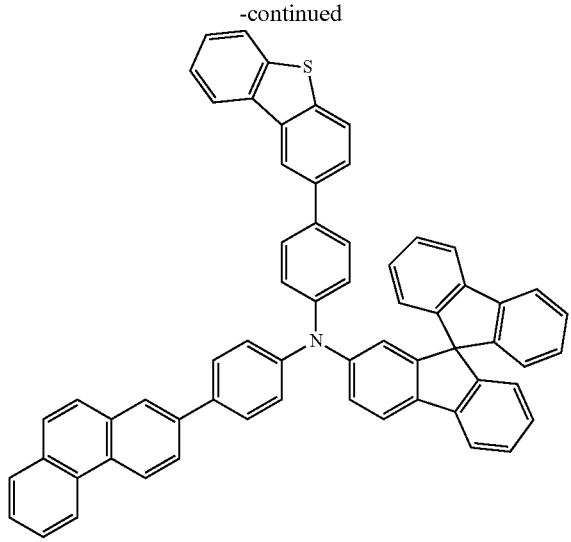
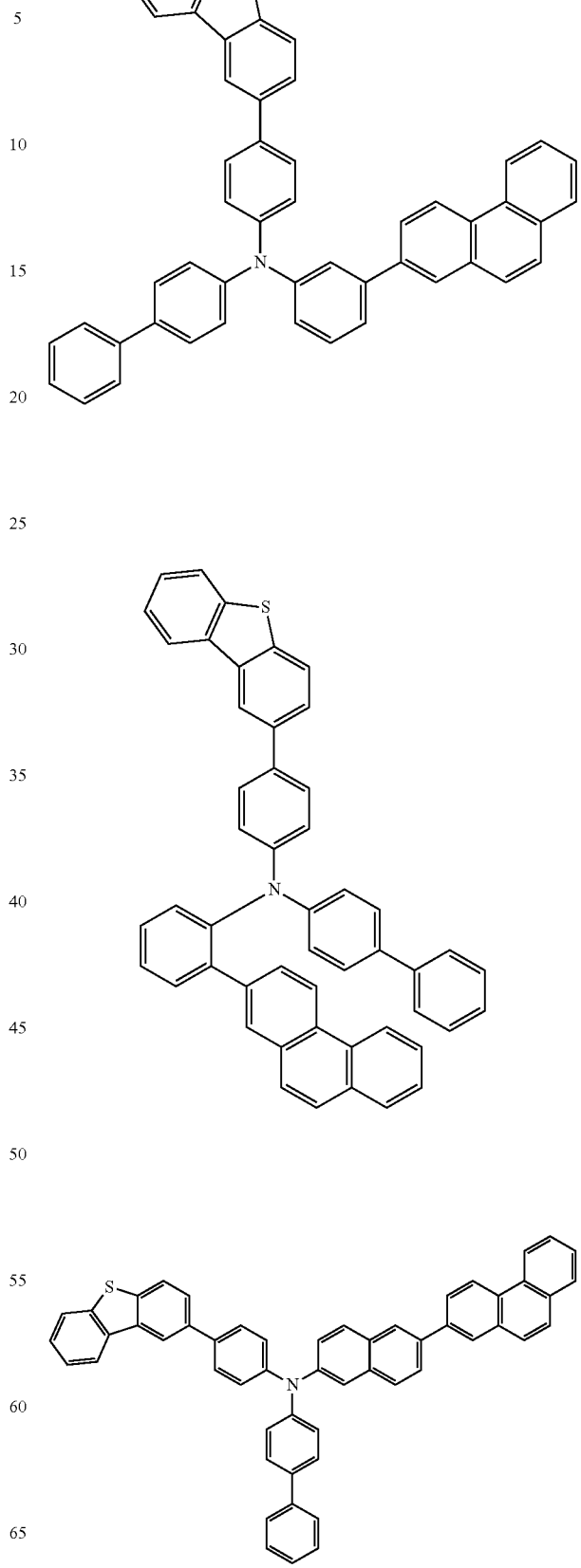

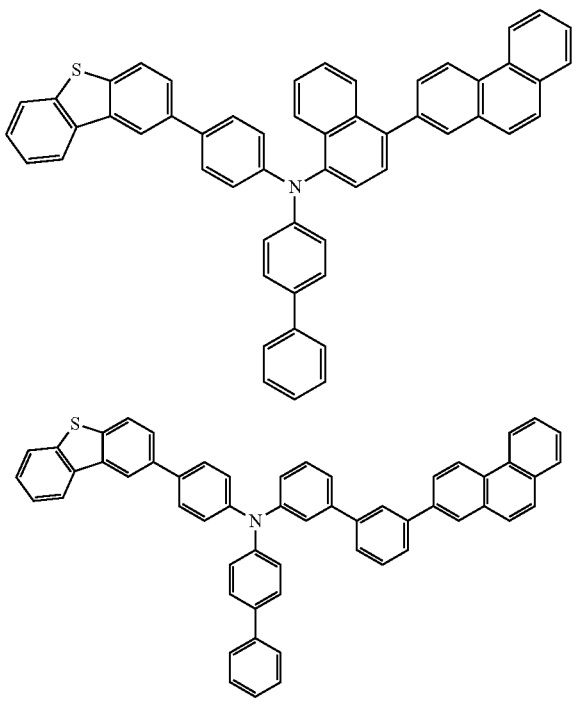
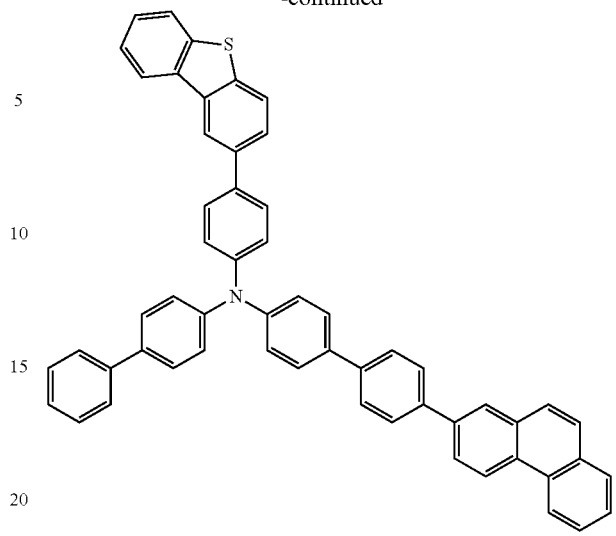
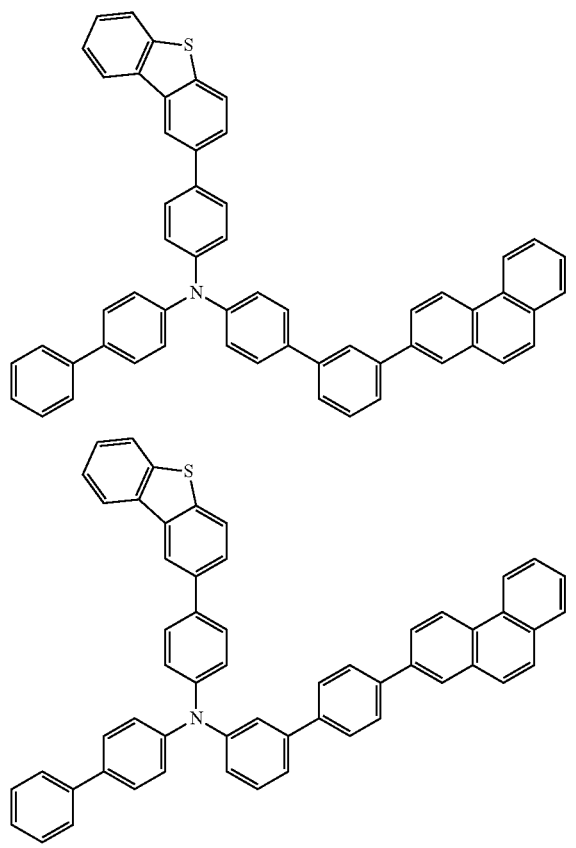

Material for Organic Electroluminescence Devices

The material for organic electroluminescence devices in an aspect of the invention comprises the compound represented by formula (1) (compound (1)), preferably at least one selected from the group consisting of the compounds represented by formulae (2) to (5).

The following description related to the compound (1) is equally applicable to the compounds represented by formulae (2) to (5) which are within formula (1) and any of species within formula (1).

The content of the compound (1) in the material for organic electroluminescence devices in an aspect of the invention is, but not particularly limited, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%).

The material for organic EL devices in an aspect of the invention is useful as a material for producing an organic EL device and may be used, for example, in a light emitting layer of a fluorescent emission unit as a host material or a dopant material or in a light emitting layer of a phosphorescent emission unit as a host material. In addition, in either a fluorescent emission unit or a phosphorescent emission unit, the material for organic EL device of the invention is also useful as a material for an anode-side organic thin film layer, for example, a hole transporting layer, a hole injecting layer, and an electron blocking layer, which is formed between an anode and a light emitting layer, and a material for a cathode-side organic thin film layer, for example, an electron transporting layer, an electron injecting layer, and a hole blocking layer, which is formed between a cathode and a light emitting layer. The anode-side organic thin film layer may be a multilayer comprising two or more layers which may be hole transporting layers. The material for organic EL devices of the invention may be included any of the two or more hole transporting layers. Thus, the material for organic EL devices of the invention may be used in any of a hole transporting layer closest to a light emitting layer, a hole transporting layer closest to an anode, and a hole transporting layer between them.

Organic Electroluminescence Device

The organic EL device in an aspect of the invention will be described below.

The organic EL device comprises an organic thin film layer between a cathode and an anode. The organic thin film layer comprises one or more layers, the organic thin film layer comprises a light emitting layer, and at least one layer of the organic thin film layer comprises the compound (1).

Examples of the organic thin film layer which comprises the compound (1) include an anode-side organic thin film layer formed between an anode and a light emitting layer (hole transporting layer, hole injecting layer, electron blocking layer, exciton blocking layer, etc.), a light emitting layer, a space layer, and a blocking layer, although not limited thereto. The compound (1) is usable in a fluorescent emission unit, for example, as a host material or a dopant material in a light emitting layer, a hole injecting layer material, and a hole transporting layer material. The compound (1) is also usable in a phosphorescent emission unit as a host material in a light emitting layer, a hole injecting layer material and a hole transporting layer material. When the anode-side organic thin film layer comprises two or more hole transporting layers, the compound (1) may be included in any of the hole transporting layers. Namely, the compound (1) may be included in any of the hole transporting layer closest to the light emitting layer, the hole transporting layer closest to the anode, and a hole transporting layer between them.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units. The "emission unit" referred to herein is the smallest unit for emitting light by the recombination of injected holes and injected electrons, which comprises an organic thin film layer comprising one or more layers, wherein at least one layer is a light emitting layer.

Representative device structures of the simple-type organic EL device are shown below:

(I) Anode/Emission Unit/Cathode

The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, with the layers in parentheses being optional:

(au) (Hole injecting layer/) Hole transporting layer/Fluorescent emitting layer (/Electron transporting layer);
(bu) (Hole injecting layer/) Hole transporting layer/Phosphorescent emitting layer (/Electron transporting layer);
(cu) (Hole injecting layer/) Hole transporting layer/First fluorescent emitting layer/Second fluorescent emitting layer (/Electron transporting layer);
(du) (Hole injecting layer/) Hole transporting layer/First phosphorescent emitting layer/Second phosphorescent emitting layer (/Electron transporting layer);
(eu) (Hole injecting layer/) Hole transporting layer/Phosphorescent emitting layer/Space layer/Fluorescent emitting layer (/Electron transporting layer);
(fu) (Hole injecting layer/) Hole transporting layer/First phosphorescent emitting layer/Second phosphorescent emitting layer/Space layer/Fluorescent emitting layer (/Electron transporting layer);
(gu) (Hole injecting layer/) Hole transporting layer/First phosphorescent emitting layer/Space layer/Second phosphorescent emitting layer/Space layer/Fluorescent emitting layer (/Electron transporting layer);
(hu) (Hole injecting layer/) Hole transporting layer/Phosphorescent emitting layer/Space layer/First fluorescent emitting layer/Second fluorescent emitting layer (/Electron transporting layer);
(iu) (Hole injecting layer/) Hole transporting layer/Electron blocking layer/Fluorescent emitting layer (/Electron transporting layer);
(ju) (Hole injecting layer/) Hole transporting layer/Electron blocking layer/Phosphorescent emitting layer (/Electron transporting layer);
(ku) (Hole injecting layer/) Hole transporting layer/Exciton blocking layer/Fluorescent emitting layer (/Electron transporting layer);
(lu) (Hole injecting layer/) Hole transporting layer/Exciton blocking layer/Phosphorescent emitting layer (/Electron transporting layer);
(mu) (Hole injecting layer/) First hole transporting layer/Second hole transporting layer/Fluorescent emitting layer (/Electron transporting layer);
(nu) (Hole injecting layer/) First hole transporting layer/Second hole transporting layer/Phosphorescent emitting layer (/Electron transporting layer);
(ou) (Hole injecting layer/) Hole transporting layer/Fluorescent emitting layer/Hole blocking layer (/Electron transporting layer); and
(pu) (Hole injecting layer/) Hole transporting layer/Fluorescent emitting layer/Triplet blocking layer (/Electron transporting layer).

The emission color of the fluorescent emitting layer and that of the phosphorescent emitting layer may be different. For example, the layered structure of the laminated emission unit (fu) may be (Hole injecting layer/) Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(II) Anode/First emission unit/Intermediate layer/Second emission unit/Cathode.

The layered structure of the first emission unit and the second emission unit may be independently selected from those exemplified above as the simple-type emission units.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting layer or a hole transporting layer 6 (anode-side organic thin film layer) may be disposed between the light emitting layer 5 and the anode 3, and an electron injecting layer or a electron transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material (hole injecting material). The compound of the invention may be used in the hole injecting layer alone or in combination with the following material.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting material: 4,4',4"-tris(N,N-diphenylamino)triphenylamine (TDATA), 4,4',4"-tris[N-(3-methylphenyl)-N-phenylamino]triphenylamine (MT-DATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino) biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 6-bis[N-(9-phenylcarbazole-3-yl)-N-phenylamino]-9-phenylcarbazole (PCzPCA2), and —[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino) phenyl]phenyl-N'-phenylamino}phenyl)methacrylamide] (PTPDMA), and poly[N,N'-bis(4-butylphenyl)-N,N'-bis (phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with the compound of the invention:

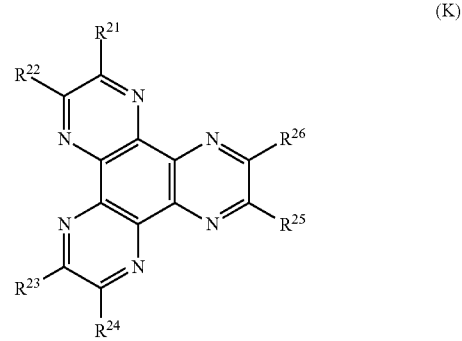

(K)

wherein $R^{21}$ to $R^{26}$ may be the same or different and each of $R^{21}$ to $R^{26}$ is independently a cyano group, —$CONH_2$, a carboxyl group, or —$COOR^{27}$ wherein $R^{27}$ is an alkyl group having 1 to 20 carbon atoms or a cycloalkyl group having 3 to 20 carbon atoms, or $R^{24}$ and $R^{22}$, $R^{23}$ and $R^{24}$, or $R^{25}$ and $R^{26}$ may be bonded to each other to form a group represented by —CO—O—CO—.

Examples of $R^{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a highly hole transporting material (hole transporting material). The compound (1) may be used in the hole transporting layer alone or in combination with the following material.

Examples of the hole transporting material include an aromatic amine compound, a carbazole derivative, and an anthracene derivative. Examples of the aromatic amine compound are 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4''-tris(N,N-diphenylamino)triphenylamine (TDATA), 4,4',4''-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of generally $10^{-6}$ cm$^2$/Vs or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly (N-vinylcarbazole) (PVK) and poly(4-vinyltriphenylamine) (PVTPA).

Compounds other than those mentioned above are also usable if their hole transporting ability is higher than their electron transporting ability. The layer comprising a highly hole-transporting material may be a single layer or a laminate of two or more layers each comprising the compound mentioned above. For example, the hole transporting layer may be a two-layered structure of a first hole transporting layer (anode side) and a second hole transporting layer (cathode side). In this case, the compound (1) may be used in either of the first hole transporting layer and the second hole transporting layer. In an embodiment of the invention, the compound (1) is preferably used in the first hole transporting layer. In another embodiment of the invention, the compound (1) is preferably used in the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carb azole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2'] iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5☐]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato) (monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the dopant material mentioned above in another material (host material). The compound (1) and other various compounds may be used as the host material. The host material preferably has a lowest unoccupied molecular orbital level (LUMO level) higher than that of the dopant material and a highest occupied molecular orbital level (HOMO level) lower than that of the dopant material.

The host material may include, for example, (1h) a metal complex, such as an aluminum complex, a beryllium complex, and a zinc complex;

(2h) a heterocyclic compound, such as an oxadiazole derivative, a benzimidazole derivative, and a phenanthroline derivative;

(3h) a fused aromatic compound, such as a carbazole derivative, an anthracene derivative, a phenanthrene derivative, a pyrene derivative, and a chrysene derivative; and (4h) an aromatic amine compound, such as a triarylamine derivative and a fused aromatic polycyclic amine derivative.

Examples thereof include:

a metal complex, such as tris(8-quinolinolato)aluminum (III) ($Alq_3$ or Alq), tris(4-methyl-8-quinolinolato)aluminum (III) ($Almq_3$), bis(10-hydroxybenzo[h]quinolinato)beryllium(II) ($BeBq_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used alone or in combination of two or more.

Electron Transporting Layer

The electron transporting layer comprises a highly electron-transporting material (electron transporting material). Examples thereof are:

(1e) a metal complex, such as an aluminum complex, a beryllium complex, and a zinc complex;

(2e) a heteroaromatic compound, such as an imidazole derivative, a benzimidazole derivative, an azine derivative, a carbazole derivative, and a phenanthroline derivative; and (3e) a macromolecular compound.

Examples of the metal complex include tris(8-quinolinolato)aluminum (III) (Alq), tris(4-methyl-8-quinolinolato) aluminum ($Almq_3$), bis(10-hydroxybenzo[h]quinolinato)beryllium ($BeBq_2$), bis(2-methyl-8-quinolinolato)(4-phenylphenolato)aluminum (III)(BAlq), bis(8-quinolinato) zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly [(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of mainly $10^{-6}$ $cm^2/Vs$ or more. Materials other than those mentioned above are also usable in the electron transporting layer if their electron transporting ability is higher than their hole transporting ability. The electron transporting layer may be a single layer or a laminate of two or more layers each comprising the material mentioned above. For example, the electron transporting layer may comprise a first electron transporting layer (light emitting layer side) and a second electron transporting layer (cathode side).

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride($CaF_2$), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as aluminum (Al), silver (Ag), indium tin oxide alloy (ITO), graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer is preferably interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be made into laminated layers.

Space Layer

For example, in an organic EL device wherein a fluorescent emitting layer and a phosphorescent emitting layer are laminated, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

In the organic EL device, a blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer. The compound (1) of the invention is preferably used also as the material for the electron blocking layer and the triplet blocking layer.

Each layer of the organic EL device can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each layer is not particularly limited and preferably 5 nm to 10 µm, more preferably 10 nm to 0.2 µm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

Synthesis Example 1 (Synthesis of Compound H1)

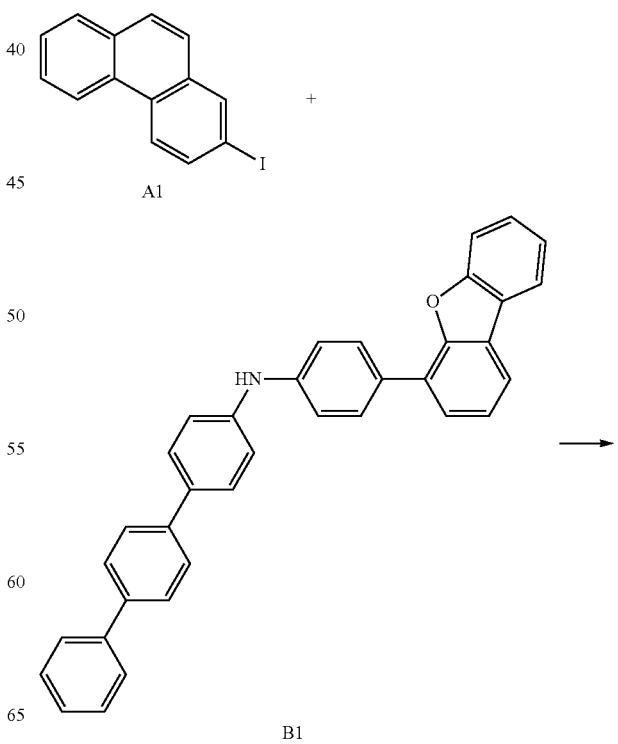

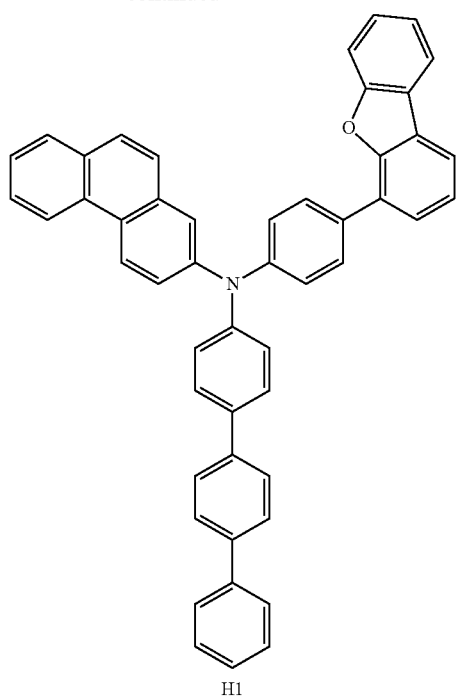

H1

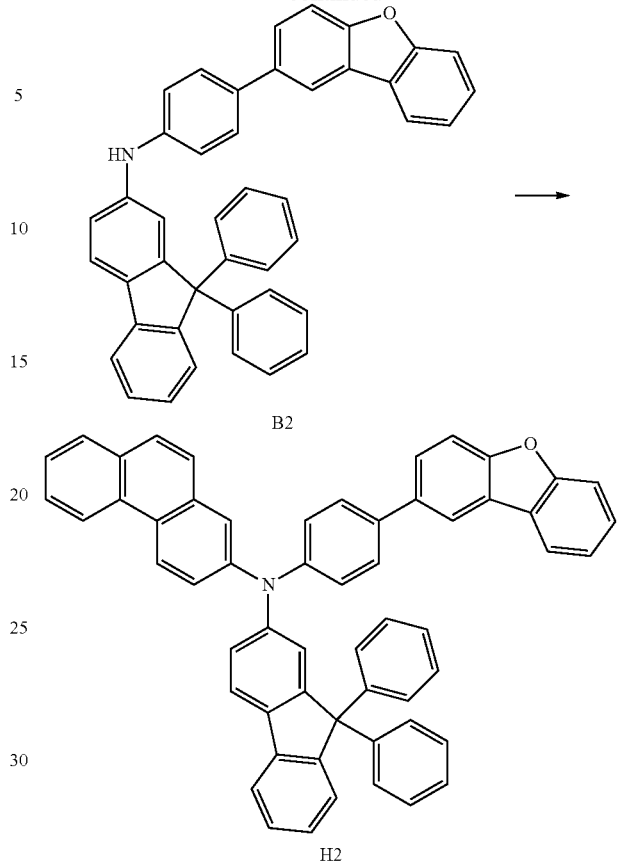

B2

H2

Under argon atmosphere, the compound A1 synthesized by the method described in WO 2009/116628 (3.34 g, 10.0 mmol), the compound B1 synthesized by the method described in 2010/061824 (4.88 g, 10.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (1.92 g, 20.0 mmol), and anhydrous xylene (100 mL) were successively mixed, and the resultant mixture was refluxed under heating for 7 h.

After cooling the reaction liquid to room temperature, the insolubles were removed by filtration, and the organic solvent was evaporated off under reduced pressure. The obtained residue was purified by silica gel column chromatography to obtain the compound H1 (4.31 g, 65% yield).

The result of LC-MS (Liquid Chromatography-Mass Spectrometry) analysis of the compound H1 is shown below.

LC-MS: calcd. for C50H33NO=663.

found m/z=663.

Synthesis Example 2 (Synthesis of Compound H2)

Under argon atmosphere, the compound A1 synthesized by the method described in WO 2009/116628 (3.34 g, 10.0 mmol), the compound B2 synthesized by the method described in WO 2014/034795 (5.76 g, 10.0 mmol), tris (dibenzylideneacetone)dipalladium (195 mg, 0.200 mmol), 2-dicyclohexylphosphino-2',6'-dimethoxybiphenyl (328 mg, 0.800 mmol), sodium t-butoxide (1.92 g, 20.0 mmol), and anhydrous xylene (100 mL) were successively mixed, and the resultant mixture was refluxed under heating for 6 h.

After cooling the reaction liquid to room temperature, the insolubles were removed by filtration, and the organic solvent was evaporated off under reduced pressure. The obtained residue was purified by silica gel column chromatography to obtain the compound H2 (5.26 g, 70% yield).

The result of LC-MS (Liquid Chromatography-Mass Spectrometry) analysis of the compound H2 is shown below.

LC-MS: calcd. for C57H37NO=751.

found m/z=751.

Intermediate Synthesis Example 1 (Synthesis of Compound A2)

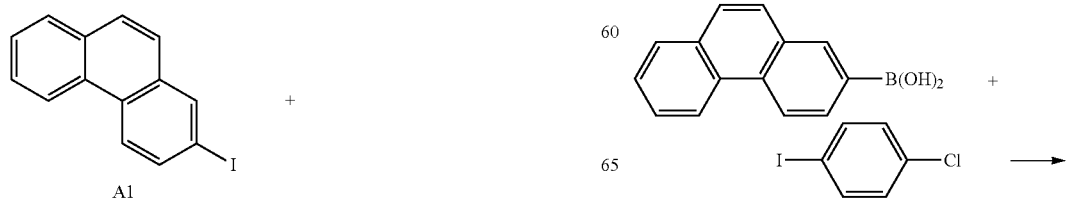

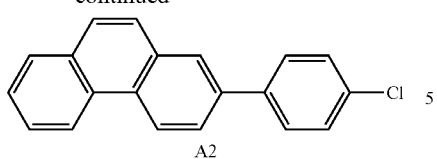

Under argon atmosphere, phenanthrene-2-boronic acid synthesized by the method described in WO 2009/116628 (11.1 g, 50 mmol), 1-chloro-4-iodobenzene (11.9 g, 50 mmol), tetrakis(triphenylphosphine)palladium(0) (1.16 g, 1 mmol), toluene (200 mL), and a 2 M aqueous solution of sodium carbonate (100 mL) were successively mixed, and the resultant mixture was refluxed under heating for 8 h.

After cooling to room temperature, the reaction solution was extracted with toluene. The aqueous layer was removed, and the organic layer was successively washed with water and a saturated brine and then dried over magnesium sulfate. After removing the magnesium sulfate, the organic layer was concentrated. The obtained residue was purified by silica gel column chromatography to obtain the compound A2 (12.9 g, 89% yield).

Synthesis Example 3 (Synthesis of Compound H3)

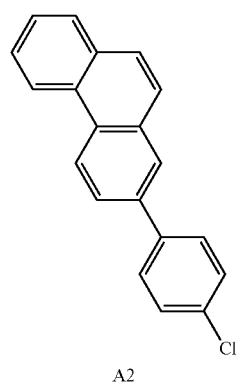

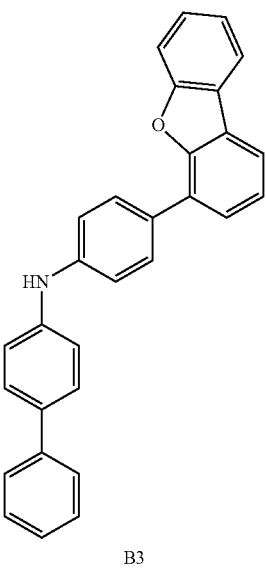

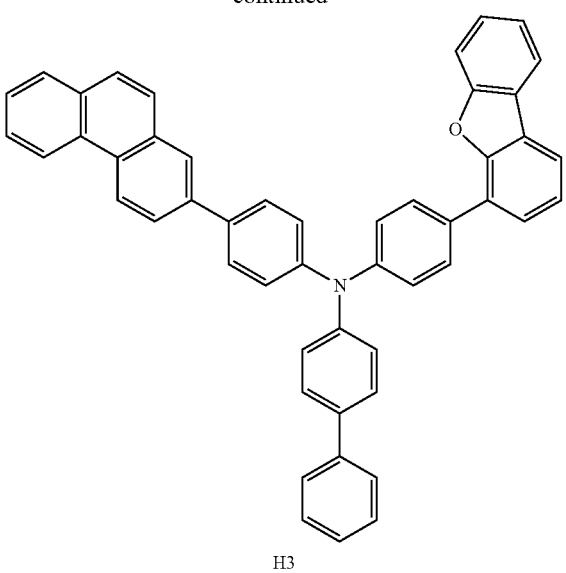

Under argon atmosphere, the compound A2 (2.89 g, 10.0 mmol), the compound B3 synthesized by the method described in WO 2007/125714 (4.11 g, 10.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (1.92 g, 20.0 mmol), and anhydrous xylene (100 mL) were successively mixed, and the resultant mixture was refluxed under heating for 8 h.

After cooling the reaction liquid to room temperature, the insolubles were removed by filtration, and the organic solvent was evaporated off under reduced pressure. The obtained residue was purified by silica gel column chromatography to obtain the compound H3 (3.65 g, 55% yield).

The result of LC-MS (Liquid Chromatography-Mass Spectrometry) analysis of the compound H3 is shown below.

LC-MS: calcd. for C50H33NO=663.

found m/z=663.

Synthesis Example 4 (Synthesis of Compound H4)

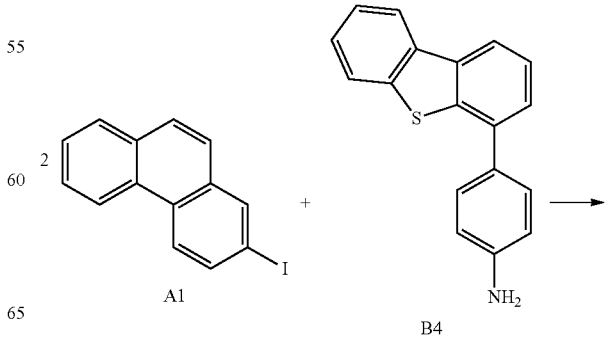

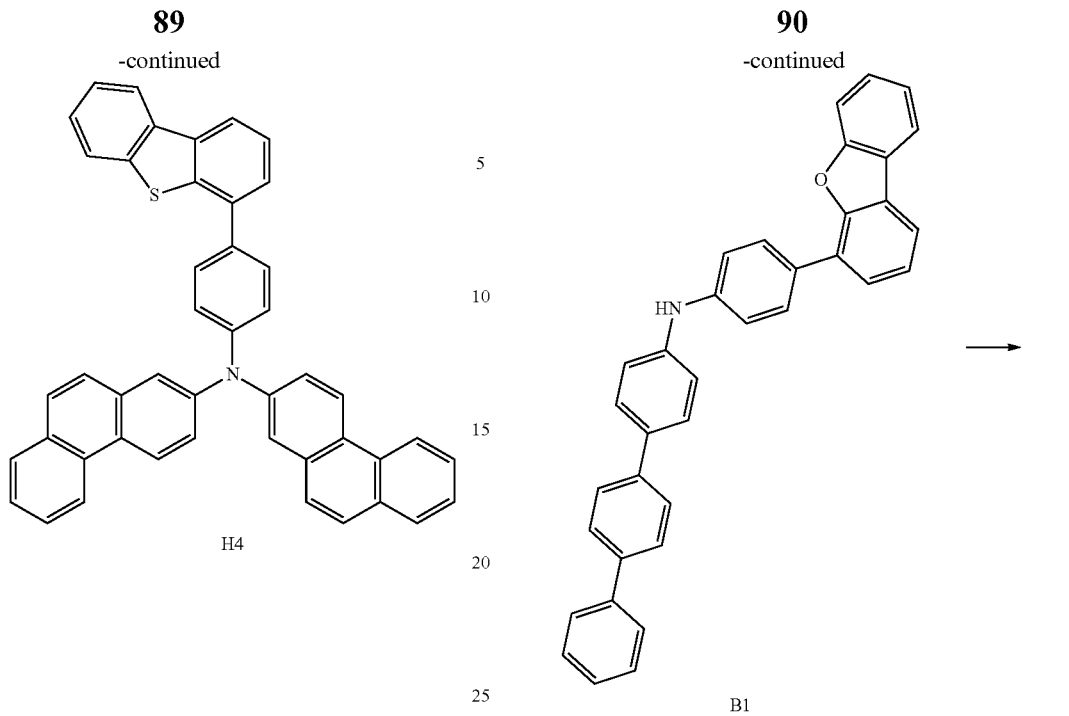

Under argon atmosphere, the compound A1 synthesized by the method described in WO 2009/116628 (6.69 g, 20.0 mmol), the compound B4 synthesized by the method described in WO 2014/034795 (2.75 g, 10.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (1.92 g, 20.0 mmol), and anhydrous xylene (100 mL) were successively mixed, and the resultant mixture was refluxed under heating for 8 h.

After cooling the reaction liquid to room temperature, the insolubles were removed by filtration, and the organic solvent was evaporated off under reduced pressure. The obtained residue was purified by silica gel column chromatography to obtain the compound H4 (2.51 g, 40% yield).

The result of LC-MS (Liquid Chromatography-Mass Spectrometry) analysis of the compound H4 is shown below.

LC-MS: calcd. for C46H29NS=627.

found m/z=627.

Synthesis Example 5 (Synthesis of Compound H5)

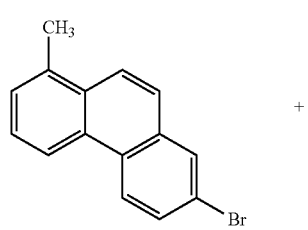

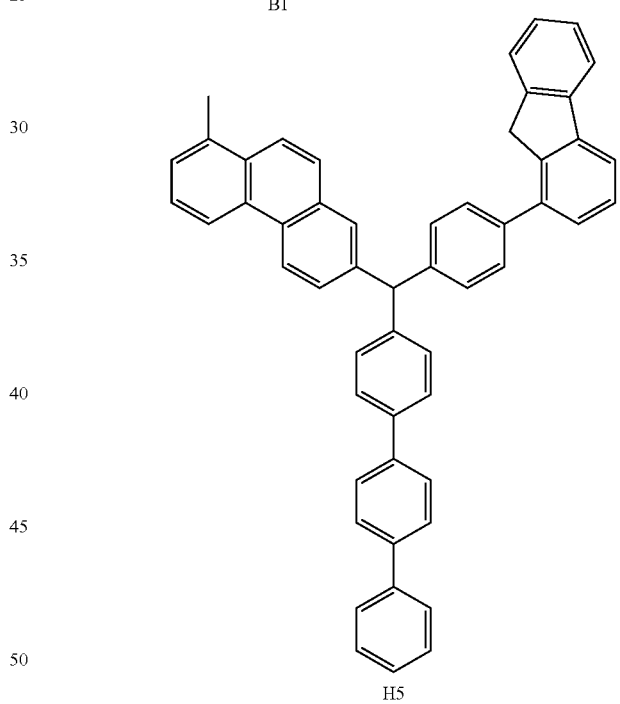

Under argon atmosphere, the compound A3 (2.71 g, 10.0 mmol), the compound B1 synthesized by the method described in WO 2010/061824 (4.87 g, 10.0 mmol), tris(dibenzylideneacetone)dipalladium (195 mg, 0.200 mmol), 2-dicyclohexylphosphino-2',6'-dimethoxybiphenyl (328 mg, 0.800 mmol), sodium t-butoxide (1.92 g, 20.0 mmol), and anhydrous xylene (100 mL) were successively mixed, and the resultant mixture was refluxed under heating for 8 h.

After cooling the reaction liquid to room temperature, the insolubles were removed by filtration, and the organic solvent was evaporated off under reduced pressure. The obtained residue was purified by silica gel column chromatography to obtain the compound H5 (3.39 g, 50% yield).

The result of LC-MS (Liquid Chromatography-Mass Spectrometry) analysis of the compound H5 is shown below.
LC-MS: calcd. for C51H35NO=677.
found m/z=677.

Synthesis Example 6 (Synthesis of Compound H6)

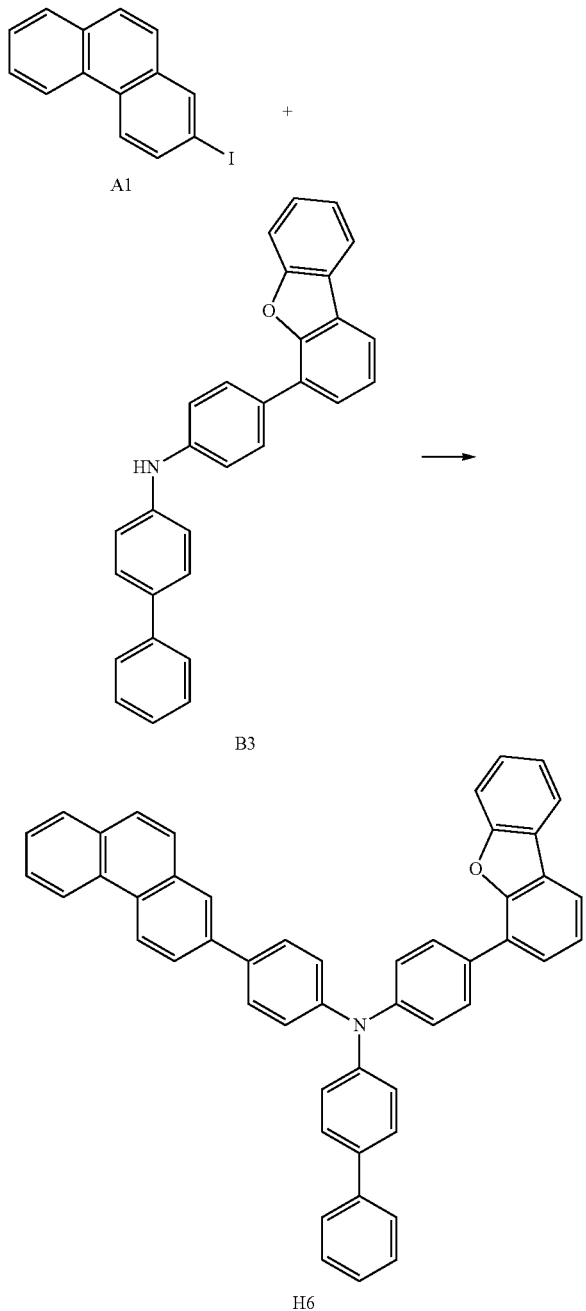

The compound H6 was synthesized in the same manner as in Synthesis Example 1 except for using the compound B3 in place of the compound B1.
The structure of the compound H6 was identified by FD-MS analysis.
FD-MS: calcd. for C50H33NO=587.
found m/z=587.

Synthesis Example 7 (Synthesis of Compound H7)

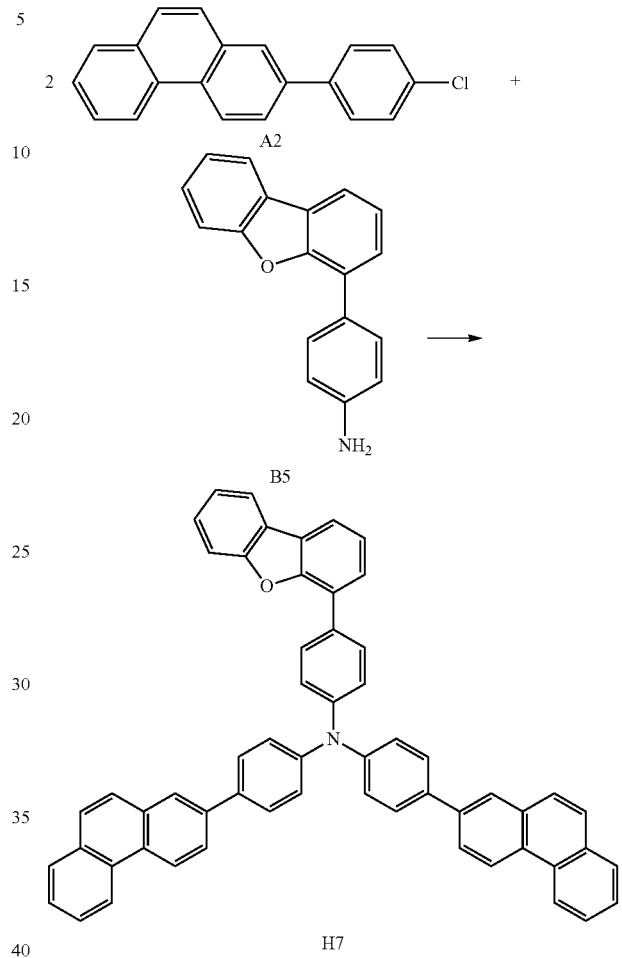

The compound H7 was synthesized in the same manner as in Synthesis Example 4 except for using the compound A2 in place of the compound A1 and using the compound B5 synthesized by the method described in WO 2014/034795 in place of the compound B4.
The structure of the compound H7 was identified by FD-MS analysis.
FD-MS: calcd. for C50H33NO=763.
found m/z=763.

Production of Organic EL Device

Example 1

A glass substrate of 75 mm long×25 mm wide×1.1 mm thick having ITO transparent electrode (product of Geomatec Company) was ultrasonically cleaned in isopropyl alcohol for 5 min and then UV/ozone cleaned for 30 min. The thickness of the ITO transparent electrode was 130 nm.
The cleaned glass substrate having ITO transparent electrode line was mounted to a substrate holder of a vacuum vapor deposition apparatus. First, the compound (HI-1) was vapor-deposited so as to cover the ITO transparent electrode line to form an HI-1 film (hole injecting layer) with a thickness of 5 nm.

On the hole injecting layer, the compound HT-1 (first hole transporting material) was vapor-deposited into an HT-1 film with a thickness of 80 nm to form a first hole transporting layer.

On the first hole transporting layer, the compound H1 was vapor-deposited into an HT-2 film with a thickness of 10 nm to form a second hole transporting layer.

On the second hole transporting layer, the compound BH-1 (host material) and the compound BD-1 (dopant material) were vapor co-deposited to form a co-deposited film with a thickness of 25 nm. The concentration of the compound BD-1 was 4.0% by mass. The co-deposited film works as a light emitting layer.

On the light emitting layer, the compound ET-1 was vapor-deposited into an ET-1 film with a thickness of 10 nm to form a first electron transporting layer. On the first electron transporting layer, the compound ET-2 was vapor-deposited into an ET-2 film with a thickness of 15 nm to form a second electron transporting layer.

On the second electron transporting layer, lithium fluoride (LiF) was vapor-deposited into a LiF film with a thickness of 1 nm to form an electron injecting electrode (cathode).

Then, on the LiF film, metallic aluminum (Al) was vapor-deposited into a metallic Al film with a thickness of 80 nm to form a metallic Al cathode.

Examples 2 to 7 and Comparative Examples 1 to 2

Each organic EL device was produced in the same manner as in Example 1 except for forming the second hole transporting layer by using each compound shown in Table 1 in place of the compound H1.

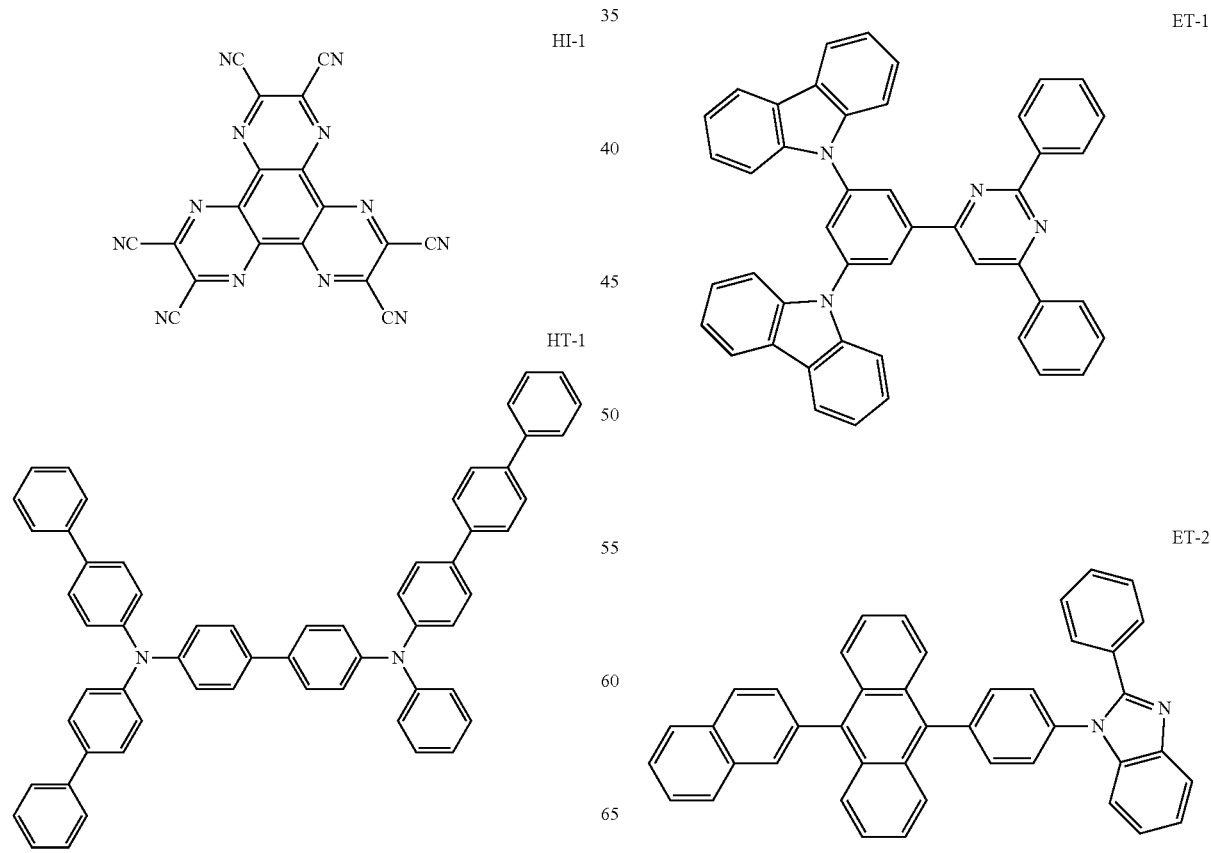

-continued

Comparative compound 1

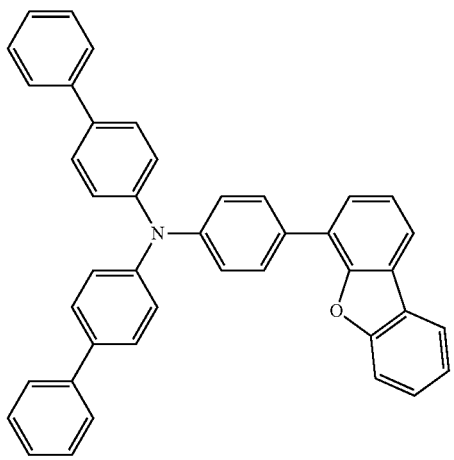

Comparative compound 2

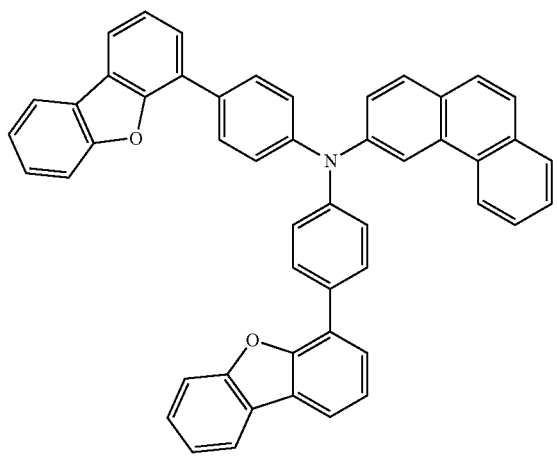

Evaluation of Organic EL Device

Each of the organic EL devices produced in the examples and the comparative examples was measured for the driving voltage by applying the voltage so as to give a current density of 10 mA/cm². In addition, the time taken until the luminance was reduced to 90% of the initial luminance (90% luminance lifetime) was measured by driving the device at a current density of 50 mA/cm². The results are shown in Table 1.

TABLE 1

| | Material of second hole transporting layer | Device performance | |
|---|---|---|---|
| | | Driving voltage (V) | 90% Luminance lifetime (h) |
| Example 1 | H1 | 3.7 | 160 |
| Example 2 | H2 | 3.6 | 120 |
| Example 3 | H3 | 3.7 | 170 |
| Example 4 | H4 | 3.7 | 140 |
| Example 5 | H6 | 3.8 | 130 |
| Example 6 | H7 | 3.7 | 180 |
| Comparative Example 1 | Comparative compound 1 | 3.8 | 100 |
| Comparative Example 2 | Comparative compound 2 | 3.8 | 50 |

It can be found from Table 1 that a long lifetime organic EL device which is operated at a low driving voltage is obtained by using the compounds H1 to H4, H6, and H7.

The compound of the invention may transport holes more easily than known materials because of its structure represented by formula (1). This may make it possible to drive the device at a low voltage and optimize the carrier balance of the device to improve the lifetime.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:
1. A compound represented by formula (1):

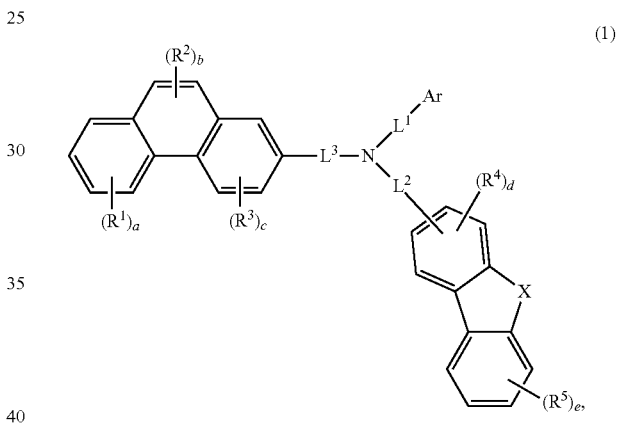

(1)

wherein:
each of $R^1$ to $R^3$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;
each of $R^4$ and $R^5$ is independently one selected from the group consisting of an alkyl group having 1 to 20 carbon atoms, a cycloalkyl group having 3 to 50 ring carbon atoms, a haloalkyl group having 1 to 20 carbon atoms, an alkoxy group having 1 to 20 carbon atoms, a haloalkoxy group having 1 to 20 carbon atoms, an aryl group having 6 to 18 ring carbon atoms, an aryloxy group having 6 to 18 ring carbon atoms, a halogen atom, and a cyano group;
a is an integer of 0 to 4;
b is an integer of 0 to 2;
c is an integer of 0 to 3;
d is an integer of 0 to 3;
e is an integer of 0 to 4;
each of $(R^1)_0$, $(R^2)_0$, $(R^3)_0$, $(R^4)_0$, and $(R^5)_0$ respectively mean that $R^1$, $R^2$, $R^3$, $R^4$ or $R^5$ is not present;

when a, b, c, d, or e is an integer of 2 or more, two to four R¹'s, two R²'s, two or three R³'s, two or three R⁴'s, and two to four R⁵'s may be the same or different, respectively; and adjacent two selected from R¹ to R⁵ are not bonded to each other, thereby failing to form a ring structure;

L1 is a single bond or an arylene group represented by formula (ii) or (iii):

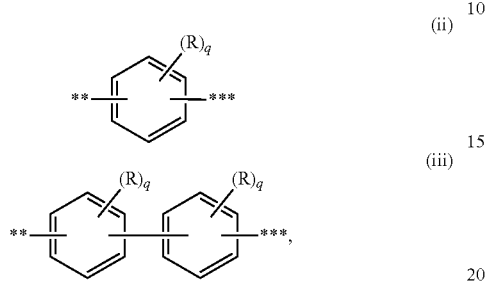

wherein in formulae (ii) and (iii):
each R is independently one selected from the group consisting of an alkyl group having 1 to 20 carbon atoms, an aryl group having 6 to 18 ring carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group;

each q is independently an integer of 0 to 4;
(R)₀ means that R is not present;
when q is an integer of 2 or more, two to four Rs, two to three Rs, or two Rs may be the same or different; and one of  and * is a bond to Ar in formula (1), and the other is a bond to the nitrogen atom in formula (1), L² is a single bond or a substituted or unsubstituted arylene group having 6 to 30 ring carbon atoms;

L³ is a substituted or unsubstituted arylene group having 6 to 30 ring carbon atoms;

Ar is represented by one selected from the group consisting of formulae (a), (b), (d), (e), (f), (g), (h), (i), (j), (k), and (m):

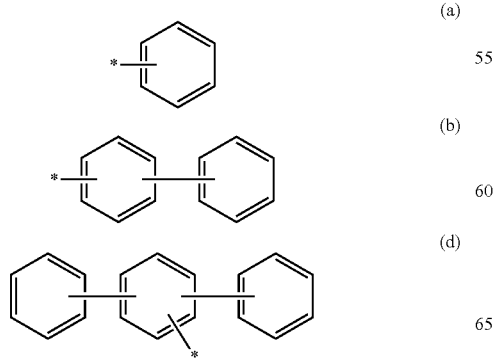

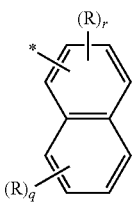

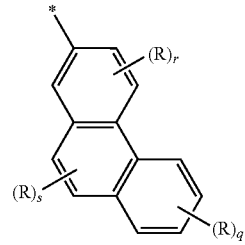

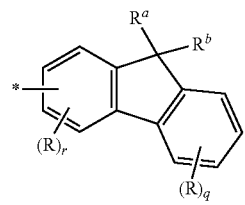

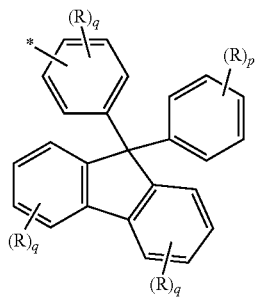

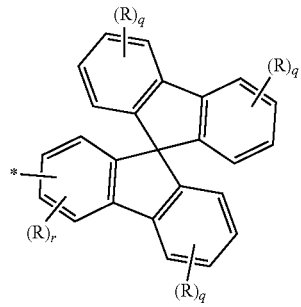

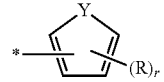

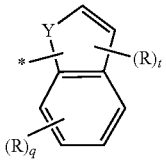

-continued

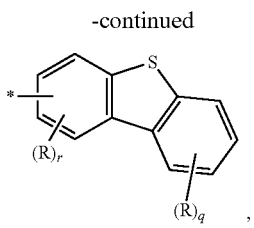

(m)

wherein in formulae (a), (b), (d), (e), (f), (g), (h), (i), (j), (k), and (m):

is a bond to $L^1$ in formulae (1),

R and q are the same as defined with respect to formulae (ii) and (iii);

each p is independently an integer of 0 to 5;

each r is independently an integer of 0 to 3;

s is independently an integer of 0 to 2;

t is independently 0 or 1;

$(R)_0$ means that R is not present;

when p, q, r or s is an integer of 2 or more, two to five Rs, two to four Rs, two to three Rs, or two Rs may be the same or different;

each of $R^a$ and $R^b$ of formula (g) is independently one selected from the group consisting of an alkyl group having 1 to 20 carbon atoms, an aryl group having 6 to 18 ring carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group;

Y of formulae (j) and (k) is a nitrogen atom, an oxygen atom, or a sulfur atom; and adjacent two Rs in formulae (a), (b), (d), (e), and (h) to (j) may be bonded to each other to form a ring structure, two selected from R, $R^a$, and $R^b$ of formula (g) may be bonded to each other to form a ring structure, and adjacent two Rs in formulae (f), (k), and (m) are not bonded to each other, thereby failing to form a ring structure, provided that when Ar is represented by formula (a) or (b), $L^1$ is a single bond;

X is an oxygen atom or a sulfur atom; and an optional substituent referred to by "substituted or unsubstituted" is one selected from the group consisting of an alkyl group having 1 to 20 carbon atoms, an aryl group having 6 to 18 ring carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group, and two or more optional groups, if present, may be the same or different.

2. The compound according to claim 1, wherein the compound is represented by formula (2):

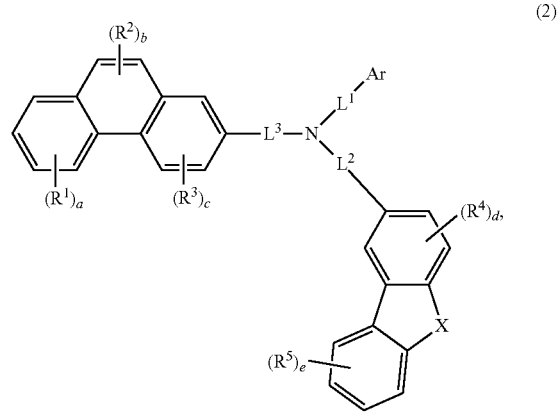

(2)

wherein $R^1$ to $R^5$, a to e, $L^1$ to $L^3$, Ar, and X are as defined in formula (1).

3. The compound according to claim 1, wherein the compound is represented by formula (3):

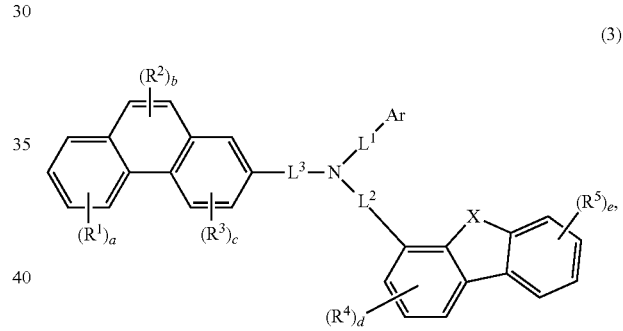

(3)

wherein $R^1$ to $R^5$, a to e, $L^1$ to $L^3$, Ar, and X are as defined in formula (1).

4. The compound according to claim 1, wherein the compound is represented by formula (4):

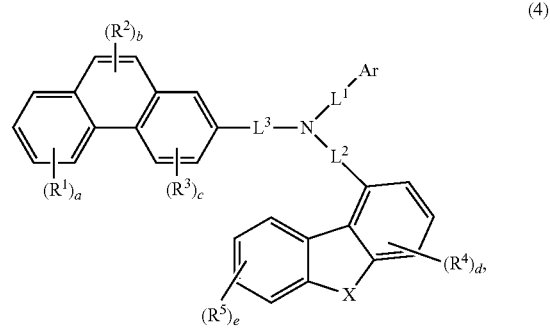

(4)

wherein $R^1$ to $R^5$, a to e, $L^1$ to $L^3$, Ar, and X are as defined in formula (1).

5. The compound according to claim 1, wherein the compound is represented by formula (5):

(5)

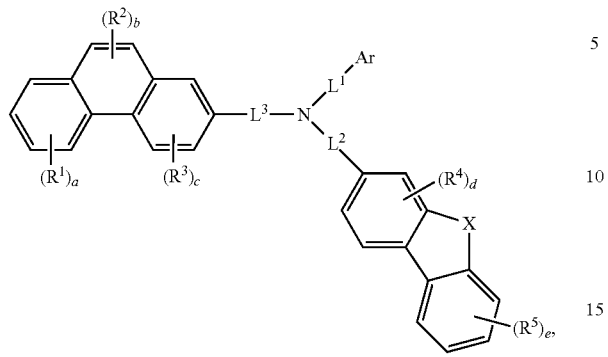

wherein R¹ to R⁵, a to e, L¹ to L³, Ar, and X are as defined in formula (1).

6. The compound according to claim 1, wherein:

when Ar is represented by formula (a), (b) or (d), L¹ is a single bond.

7. The compound according to claim 1, wherein:

Ar is represented by one selected from the group consisting of formulae (a), (b), (e), (f), (g), (h), (i), (j), (k), and (m).

8. The compound according to claim 1, wherein:

Ar is represented by one selected from the group consisting of formulae (a), (b), (e), (f), (g), (h), and (i).

9. The compound according to claim 1, wherein Ar is represented by any of formulae (b-1), (b-2), (b-3), (d-1), (d-2), (d-3), (e-1), (f), (g-1), (i-1), (i-2), (m-1), and (m-2):

(b-1)
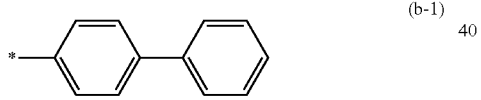

(b-2)

(b-3)

(d-1)
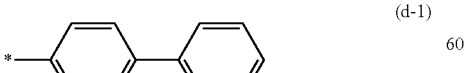

(d-2)
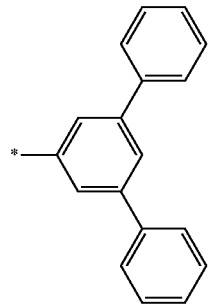

(d-3)
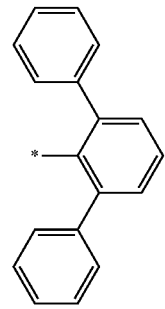

(e-1)
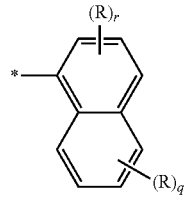

(f)
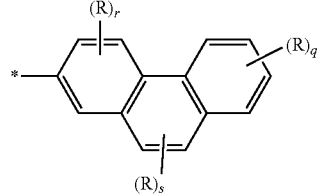

(g-1)
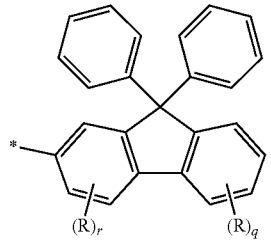

(i-1)
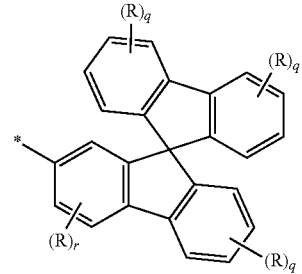

-continued

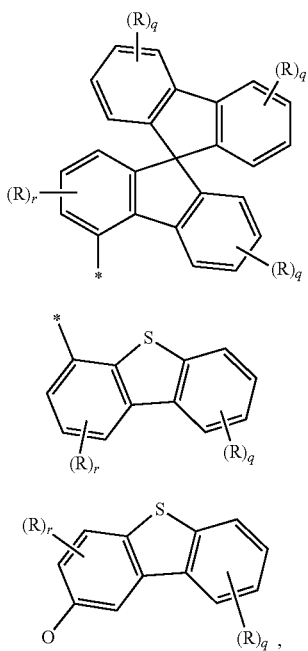

(i-2)

(m-1)

(m-2)

wherein:

R, q, r, s, and * of formulae (b-1), (b-2), (b-3), (d-1), (d-2), (d-3), (e-1), (f), (g-1), (i-1), (i-2), (m-1), and (m-2) are the same as defined with respect to formulae (a), (b), (d), (e), (f), (g), (h), (i), (j), (k), and (m);

(R)$_0$ means that R is not present;

when q, r or s is an integer of 2 or more, two to five Rs, two to four Rs, two to three Rs, or two Rs may be the same or different; and provided that adjacent two Rs in each of the above formulae are not bonded to each other, thereby failing to form a ring structure.

10. The compound according to claim 1, wherein the arylene group having 6 to 30 ring carbon atoms for $L^2$ and $L^3$ is one selected from the group consisting of divalent groups obtained by removing one hydrogen atom from a phenyl group, a biphenylyl group, a terphenylyl group, a biphenylenyl group, a naphthyl group, an acenaphthylenyl group, an anthryl group, a benzanthryl group, an aceanthryl group, a 2-phenanthryl group, a benzophenanthryl group, a triphenylenyl group, a phenalenyl group, a fluorenyl group, a benzofluorenyl group, a 9,9'-spirobifluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group.

11. The compound according to claim 1, wherein $L^2$ is a single bond or an arylene group represented by formula (ii) or (iii):

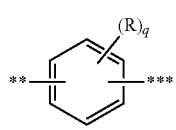

(ii)

-continued

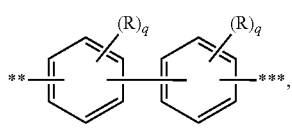

(iii)

wherein:

R and q are the same as defined with respect to formulae (ii) and (iii) for $L^1$; and one of  and * is a bond to the dibenzofuran ring or the dibenzothiophene ring in formula (1), and the other is a bond to the nitrogen atom in formula (1).

12. The compound according to claim 1, wherein $L^3$ is an arylene group represented by formula (ii) or (iii):

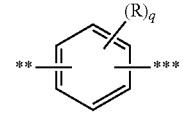

(ii)

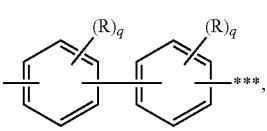

(iii)

wherein:

R and q are the same as defined with respect to formulae (ii) and (iii) for $L^1$, (R)$_0$ means that R is not present;

when q is an integer of 2 or more, two to four Rs, two to three Rs, or two Rs may be the same or different; and one of  and * is a bond to the 2-phenanthryl group in formula (1), and the other is a bond to the nitrogen atom in formula (1).

13. The compound according to claim 3, wherein:

Ar is a group represented by formula (b-1), (b-2), (b-3), (c 1), (c 2), (c 3), (d-1), (d-3), (f), (g-1), (i-1), or (i-2);

$L^1$ is a single bond;

$L^2$ is a group represented by formula (ii); and $L^3$ is a group represented by formula (ii) or (iii).

14. The compound according to claim 3, wherein:

Ar is a group represented by formula (b-1), (b-2), or (g-1);

$L^1$ is a single bond; and each of $L^2$ and $L^3$ is a group represented by formula (ii).

15. The compound according to claim 3, wherein:

Ar is a group represented by formula (d-2), (e-1), (f), (m-1), or (m-2);

each of $L^1$ and $L^2$ is a group represented by formula (ii); and $L^3$ is a single bond group represented by formula (ii) or (iii).

16. The compound according to claim 3, wherein:

Ar is a group represented by formula (b-1) or (f);

each of $L^2$ and $L^3$ is a group represented by formula (ii); and $L^1$ is a single bond.

17. The compound according to claim 11, wherein the group represented by formula (ii) is a p-phenylene group.

18. The compound according to claim 1, wherein:

each of $R^4$ and $R^5$ is independently an aryl group having 6 to 18 ring carbon atoms; and the aryl group in the substituted or unsubstituted aryl group having 6 to 18 ring carbon atoms for $R^4$ and $R^5$ is a phenyl group or a biphenylyl group.

19. A material for organic electroluminescence devices, the material comprising the compound according to claim 1.

20. An organic electroluminescence device, comprising:
a cathode;
an anode; and
an organic thin film layer disposed between the cathode and the anode,
wherein:
the organic thin film layer comprises one or more layers;
the organic thin film layer comprises a light emitting layer; and
at least one layer of the organic thin film layer comprises the compound according to claim 1.

21. The organic electroluminescence device according to claim 20, wherein:
the organic electroluminescence device comprises a hole transporting layer between the anode and the light emitting layer; and
the hole transporting layer comprises the compound.

22. The organic electroluminescence device according to claim 20, wherein:
the organic electroluminescence device comprises an electron blocking layer between the anode and the light emitting layer; and
the electron blocking layer comprises the compound.

23. The organic electroluminescence device according to claim 20, wherein:
the organic electroluminescence device comprises an exciton blocking layer between the anode and the light emitting layer; and
the exciton blocking layer comprises the compound.

24. The organic electroluminescence device according to claim 20, wherein:
the organic electroluminescence device comprises an anode-side organic thin film layer between the anode and the light emitting layer;
the anode-side organic thin film layer comprises one or more layers; and
at least one layer of the anode-side organic thin film layer comprises the compound.

25. The organic electroluminescence device according to claim 24, wherein:
two or more layers of the anode-side organic thin film layer are hole transporting layers; and
a hole transporting layer closest to the light emitting layer comprises the compound.

26. An electronic device, comprising the organic electroluminescence device according to claim 20.

27. The compound according to claim 1, wherein each q in formulae (ii) and (iii) for $L^1$ is independently an integer of 0 or 1.

28. The compound according to claim 1, wherein R in formulae (ii) and (iii) for $L^1$ is independently one selected from the group consisting of an alkyl group having 1 to 20 carbon atoms, a cycloalkyl group having 3 to 50 ring carbon atoms, an aralkyl group having 7 to 30 carbon atom which includes an aryl group having 6 to 18 ring carbon atoms, an alkoxy group having 1 to 20 carbon atoms, an aryloxy group having 6 to 18 ring carbon atoms, a mono-, di-, or tri-substituted silyl group including a substituent selected from an alkyl group having 1 to 20 carbon atoms and an aryl group having 6 to 18 ring carbon atoms, a haloalkyl group having 1 to 20 carbon atoms, a haloalkoxy group having 1 to 20 carbon atoms, a halogen atom, a cyano group, and a nitro group.

29. The compound according to claim 1, wherein
$L^1$ is a single bond or an arylene group represented by formula (ii) or (iii):

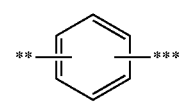

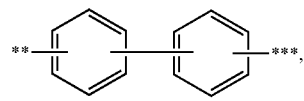

wherein in formulae (ii) and (iii):
one of  and * is a bond to Ar in formula (1), and the other is a bond to the nitrogen atom in formula (1),
provided that when Ar is represented by formula (a), (b), or (d), $L^1$ is a single bond.

* * * * *